United States Patent [19]
Fujio et al.

[11] Patent Number: 5,471,988
[45] Date of Patent: Dec. 5, 1995

[54] ULTRASONIC DIAGNOSIS AND THERAPY SYSTEM IN WHICH FOCUSING POINT OF THERAPEUTIC ULTRASONIC WAVE IS LOCKED AT PREDETERMINED POSITION WITHIN OBSERVATION ULTRASONIC SCANNING RANGE

[75] Inventors: Kouji Fujio, Hachioji; Isami Hirao, Hino; Sakae Takehana, Machida; Yasuhiro Ueda, Kokubunji; Takashi Tsukaya, Hachioji; Yoshinao Oaki, Hino, all of Japan; Seiji Kuramoto, Woodbury, N.Y.

[73] Assignee: Olympus Optical Co., Ltd., Tokyo, Japan

[21] Appl. No.: 363,621

[22] Filed: Dec. 23, 1994

[30] Foreign Application Priority Data

| Dec. 24, 1993 | [JP] | Japan | 5-345934 |
| Feb. 21, 1994 | [JP] | Japan | 6-022580 |
| Feb. 22, 1994 | [JP] | Japan | 6-024516 |
| Oct. 21, 1994 | [JP] | Japan | 6-257158 |

[51] Int. Cl.$^6$ ............................................. A61B 8/12
[52] U.S. Cl. ........................ 128/660.03; 128/662.06; 607/97
[58] Field of Search .................... 128/660.03, 660.08, 128/660.09, 660.10, 661.01, 662.03, 662.06, 663.01, 665, 4, 6; 607/88, 92, 96, 97

[56] References Cited

U.S. PATENT DOCUMENTS

| 4,932,414 | 6/1990 | Coleman et al. | 128/660.03 |
| 5,036,855 | 8/1991 | Fry et al. | 128/662.03 |
| 5,158,085 | 10/1992 | Belikan et al. | 128/660.03 |

Primary Examiner—George Manuel
Attorney, Agent, or Firm—Armstrong, Westerman, Hattori, McLeland & Naughton

[57] ABSTRACT

Provided on the side of a distal end of an insertion part are an observation ultrasonic transducer for acquiring an ultrasonic image and a therapeutic ultrasonic transducer for outputting a therapeutic ultrasonic wave so as to be focused. Positioning or the like between the observation ultrasonic transducer and the therapeutic ultrasonic transducer is so conducted that a focusing point at which the therapeutic ultrasonic wave is focused is locked to a predetermined position within a scanning range of the observation ultrasonic wave. If the position of the focusing point is locked whereby a lesion part to be treated is set to a predetermined position on an ultrasonic image, it is necessarily possible to conduct the position setting to the focusing point. It is also made possible to confirm the position of the lesion part and to acoustically observe a state of the lesion part during irradiation of the therapeutic ultrasonic wave.

66 Claims, 58 Drawing Sheets

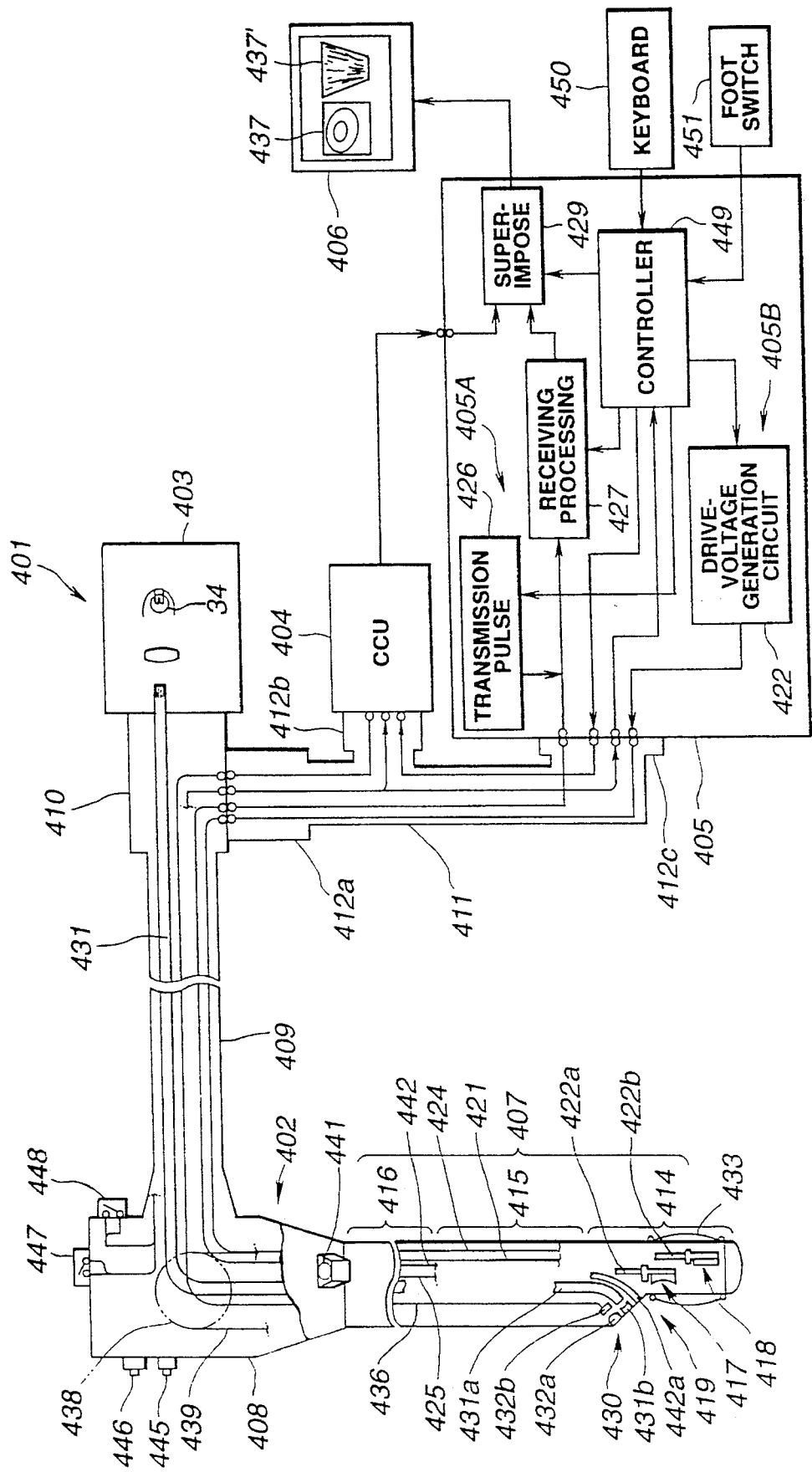

ULTRASONIC DIAGNOSIS AND THERAPY SYSTEM IN WHICH FOCUSING POINT OF THERAPEUTIC ULTRASONIC WAVE IS LOCKED AT PREDETERMINED POSITION WITHIN OBSERVATION ULTRASONIC SCANNING RANGE

BACKGROUND OF THE INVENTION

FIELD OF THE INVENTION AND RELATED ART AND PRIOR ART STATEMENT

The present invention relates to an ultrasonic diagnosis and therapy (treatment) system having an ultrasonic probe which is inserted into a body cavity or coelom to emit an observation ultrasonic wave and a therapeutic ultrasonic wave.

Generally, various kinds of ultrasonic therapy apparatuses have conventionally been proposed in which ultrasonic pulses are repeatedly sent or transmitted into organism tissues from ultrasonic transducers, echoes of the ultrasonic pulses which are reflected from the organism tissues are received by the ultrasonic transducers which are provided integrally with each other or separately from each other, and a direction in which the ultrasonic pulses are transmitted and received is gradually shifted, whereby information which is collected from a plurality of directions within the organism is displayed as visible ultrasonic tomographic or ultrasonogram images.

It is general that such ultrasonic diagnosis apparatuses are due to external ultrasonic probes.

However, probes which are combined with endoscopes, and internal ultrasonic probes such as ultrasonic probes having thin diameters, coelom ultrasonic proves inserted into the coelom, or the like, are also used widely.

Meanwhile, various kinds of ultrasonic therapy apparatuses have also been proposed such as calculus crushing apparatuses, ultrasonic thermotherapy apparatuses or the like in which various kinds of therapies are conducted by focusing the ultrasonic wave. Of these therapy apparatuses due to the ultrasonic wave, there have been ultrasonic high-temperature therapy apparatuses in which organism tissues such as cancer or carcinoma tissues or the like are instantaneously cauterized in high temperature and are treated by the focused ultrasonic wave of high strength or intensity.

As the ultrasonic high-temperature therapy apparatuses, an arrangement has been known which is provided with an internal probe building therein an ultrasonic transducer of relatively small size, and which is inserted into a rectum to treat a hypertrophied prostate, in addition to an arrangement in which ultrasonic wave is focused onto an object part from an external applicator which has an ultrasonic transducer wide in opening, in order to acquire a focused ultrasonic wave having high intensity.

For example, disclosed in PCT WO93/16641 is an arrangement in which an ultrasonic transducer which is capable of conducting linear and sector scanning is arranged at a distal end of a probe, and an ultrasonic wave having weak energy is scanned to acquire an observation image, to thereby detect a position of an object part to be treated and, thereafter, the position of the ultrasonic transducer is so set as to be capable of irradiating the ultrasonic wave to the object part to be treated, and the ultrasonic wave having strong or high energy is irradiated to conduct therapy.

This first prior-art example has the possibility that function thereof is dropped or reduced less than case where exclusive ultrasonic transducers are provided, because the ultrasonic transducers are used for observation and for therapy, respectively.

For example, in case where observation is conducted the energy strength may be weak and, accordingly, the size of the ultrasonic transducer may be small or low.

Meanwhile, in case where therapy is conducted, a high ultrasonic wave becomes necessary or is required and, accordingly, it is better that the size of the ultrasonic transducer is large as far as possible. Further, it is necessary to scan the ultrasonic wave in order to conduct the observation.

Accordingly, in order to cause the ultrasonic transducer to have both functions like the prior art example, it will be required to or be necessary to make the relatively large ultrasonic transducer to an Moreover, in order to position an irradiation part of the ultrasonic transducer so as to be capable of irradiating the therapeutic ultrasonic wave toward the object part to be treated, it is required that scanning is first made by the ultrasonic wave having weak or low energy and, thereafter, an irradiation direction is locked to the object part.

There is the possibility that, if there is relative movement between the probe and the coelop wall or the like with which the probe is in acoustic contact, or the like within the time until the locking is conducted, the therapeutic ultrasonic wave is irradiated to parts which are different from the object part.

Specifically, in the prior-art example, operation or work is required or necessary that the ultrasonic wave is scanned under the observation state, a position of the object part is detected from an observation image thereof, the ultrasonic transducer is set to a scanning position where the ultrasonic wave can be outputted with respect to the aforesaid position, and setting is made to a stage capable of outputting the therapeutic ultrasonic wave so as to be focused. In addition, since the scanning position is locked under the set state, the state becomes a state where the observation image cannot be acquired. For this reason, even if there is a change in state after having been set, it is impossible to confirm the change in state.

It is desirable in order to secure the safety as the therapy apparatus that, in case where the therapeutic ultrasonic wave is outputted, it is possible to confirm, from the ultrasonic observation image, or the like, that a focusing point of the therapeutic ultrasonic wave is set to the object part to be treated, or it is desirable to have equivalent function.

In the prior-art example, it is necessary to scan the ultrasonic wave in order to conduct the confirmation. The lock must be released in order for the scanning.

Further, in order to confirm the treated or cured state of the object part in case where the therapeutic ultrasonic wave is irradiated to conduct the high-temperature therapy, it becomes necessary to scan the ultrasonic wave to acquire the image.

In case where the therapeutic ultrasonic wave is irradiated to conduct the high-temperature therapy, it is necessary that an amount of irradiation is an adequate amount. If excessive irradiation is conducted, peripheral parts will also be treated in high temperature. For this reason, it is desirably confirm, by the ultrasonic observation image, whether or not, after the object part has been irradiated by an adequate amount of irradiation, the object part is treated in high temperature by the amount of irradiation.

In the prior-art example, also in case where the confirmation is conducted, it is necessary to change over to an observation state to conduct the scanning of the ultrasonic wave. Moreover, in case where irradiation is necessary, re-setting must be conducted to a positioning position.

Furthermore, there are many cases where, in the prior-art example, since the probe is rigid, it becomes difficult that the irradiation part which irradiates the ultrasonic wave, on the distal side of the probe is focused to the object part so as to be made to a state capable of irradiating. That is, since the ultrasonic wave is outputted to the side of the probe, in order to set the object part at least to the side of the probe, the insertion direction of the probe is restrained to a narrow range or scope. On the contrary, if the construction is a construction which has a curvature part at the insertion part, this restriction can remarkably be solved.

Meanwhile, Japanese Patent Unexamined Publication No. SHO 62-127050 (127050/1987) discloses an ultrasonic endoscope which is provided with an ultrasonic probe of structure in which an observation ultrasonic transducer and a therapeutic ultrasonic transducer are arranged at a distal part of an endoscope insertion part such that their back-face sides are joined to each other, and both the ultrasonic transducers are mounted on a distal end of a shaft which is rotated.

The second prior-art example has the observation transducer and the therapeutic transducer. However, since the second prior-art example is of structure which is rotated about a common shaft, the therapeutic transducer is also rotated in case where the observation is conducted. Further, in order to conduct the therapy, it is necessary to stop scanning of the observation transducer. Accordingly, the second prior-art example has problems similar to those of the first prior-art example, except for a merit having the curvature part.

OBJECTS AND SUMMARY OF THE INVENTION

An object of the invention is to provide an ultrasonic diagnosis and therapy (treatment) system which conducts operation of ultrasonic therapy by a therapeutic ultrasonic transducer under a state inserted into a coelom, and also which can conduct also ultrasonic observation by an observation ultrasonic transducer in parallel therewith.

Another object of the invention is to provide an ultrasonic diagnosis and therapy system which can acoustically observe a state of an irradiation part to which a therapeutic ultrasonic wave is irradiated, under a state inserted into a coelom.

According to the invention, there is provided an ultrasonic diagnosis and therapy system comprising:

ultrasonic observation therapy means in which an observation ultrasonic transducer for sending and receiving observation ultrasonic wave in order to acquire ultrasonic images and a therapeutic ultrasonic transducer for outputting a therapeutic ultrasonic wave for conducting therapy with respect to an object part so as to be focused are provided on the side of a distal end of an elongated insertion part which is insertable into a coelom;

signal processing means for conducting signal processing which generates a signal driving said observation ultrasonic transducer and which generates an image signal from an ultrasonic signal which is received by said observation ultrasonic transducer;

drive means for driving said therapeutic ultrasonic transducer to generate a drive signal for generating a therapeutic ultrasonic wave;

display means for displaying said ultrasonic image corresponding to said image signal, by the fact that said image signal is inputted; and scanning means for scanning said observation ultrasonic wave under a state in which a focusing point of said therapeutic ultrasonic wave is locked to a predetermined position within a scanning range of said observation ultrasonic wave, wherein the object part is set to a predetermined position within the scanning range of said observation ultrasonic wave, whereby it is possible to set the focusing point of said therapeutic ultrasonic wave to the position of the object part; and, under the state, the therapeutic ultrasonic wave is irradiated whereby it is possible to secure that the therapeutic ultrasonic wave is focused to the object part to conduct the therapy. Further, it is possible that, during time in which said therapeutic ultrasonic wave is irradiated in focusing to the object part, a state of the object part is acoustically observed by said observation ultrasonic wave.

BRIEF DESCRIPTION OF THE DRAWINGS

FIG. 1 to FIG. 7F relate to a first embodiment of the invention, FIG. 1 being a whole arrangement view of an ultrasonic diagnosis and therapy (treatment) system according to the first embodiment of the invention;

FIG. 3 is a cross-sectional view showing an arrangement of a distal-end part in FIG. 2B;

FIG. 4 is a view showing a using mode or state of the ultrasonic probe;

FIG. 5 is a view showing an ultrasonic-wave sending state from the distal-end part of the ultrasonic probe;

FIG. 6 is a flow chart showing an example of a therapy method which uses the first embodiment;

FIG. 7A to FIG. 7F are operation explanatory views in FIG. 6;

FIG. 12 is a view showing a specific one example on the side of a distal end of an ultrasonic probe according to the fifth embodiment;

FIG. 13 is a whole arrangement view of an ultrasonic diagnosis and therapy system according to the fifth embodiment;

FIG. 14 is a view showing an another arrangement example in the fifth embodiment;

FIG. 15 is a view showing an another arrangement example in the fifth embodiment;

FIG. 16 is a view showing the other arrangement example in the fifth embodiment;

FIG. 17 to FIG. 21 relate to a sixth embodiment of the invention, FIG. 17 being a view showing an arrangement on a distal-end side of an ultrasonic probe in the sixth embodiment;

FIG. 18 is a view showing an outer appearance of an observation & therapeutic ultrasonic transducer in FIG. 17;

FIG. 19 is a longitudinal cross-sectional view of the observation & therapeutic ultrasonic transducer in FIG. 18;

FIG. 21 is a view showing an arrangement on the side of a distal end of an ultrasonic probe which is different from that shown in FIG. 17;

FIG. 22A to FIG. 23B relate to a modification of the sixth embodiment, FIG. 22A being a view showing an observation & therapeutic ultrasonic transducer;

FIG. 23B is a cross-sectional view of FIG. 23A;

FIG. 24 to FIG. 31 relate to a seventh embodiment of the invention, FIG. 24 being an arrangement view showing an arrangement of an ultrasonic diagnosis and therapy system according to the seventh embodiment;

FIG. 25 is a perspective view showing an outer appearance of an ultrasonic probe in the seventh embodiment;

FIG. 26 is a perspective view showing an outer appearance of an ultrasonic probe according to a modification of FIG. 25;

FIG. 27 is a perspective view showing a distal-end side of the ultrasonic probe;

FIG. 29 is a perspective view showing a distal-end side of an ultrasonic probe according to a second modification;

FIG. 30 is a perspective view showing a distal-end side of an ultrasonic probe according to a third modification;

FIG. 31 is an explanatory view showing a use example, of operation description of the seventh embodiment;

FIG. 33 is a perspective view showing a distal-end side of an ultrasonic probe according to a first modification;

FIG. 34 is a perspective view showing a distal-end side of an ultrasonic probe according to a second modification;

FIG. 36 is a perspective view showing a distal-end side of an ultrasonic probe according to a first modification;

FIG. 37 is a perspective view showing a distal-end side of an ultrasonic probe according to a second modification;

FIG. 38 is an explanatory view showing a using example, of operation description of the ninth embodiment;

FIG. 40 is an explanatory view showing a using example, of operation description of the tenth embodiment;

FIG. 42 is a perspective view showing a distal-end side of an ultrasonic probe according to a first modification;

FIG. 43 is a top plan view showing a distal-end side of an ultrasonic probe according to a second modification;

FIG. 48 is a side elevational view showing an arrangement of an ultrasonic probe in a first modification;

FIG. 49 is a perspective view showing an arrangement on the side of a distal end of an ultrasonic probe in a second modification;

FIG. 50 is a perspective view showing an arrangement on the side of a distal end of an ultrasonic probe in a third modification;

FIG. 54 is a cross-sectional view showing an arrangement of a distal-end part of an ultrasonic probe in a modification;

FIG. 55A to FIG. 57B relate to a nineteenth embodiment of the invention, FIG. 55A being a perspective view showing an arrangement on the side of a distal end of an ultrasonic probe in the nineteenth embodiment, with an ultrasonic therapy means demounted;

FIG. 57B is a perspective view showing an arrangement on the side of a distal end of the ultrasonic probe under a state in which the ultrasonic therapy means is mounted;

FIG. 58 to FIG. 61 relate to a twentieth embodiment of the invention, FIG. 58 being a general or whole view showing a schematic arrangement of an ultrasonic diagnosis and therapy system according to the twentieth embodiment;

FIG. 59 is a perspective view showing an ultrasonic probe having optical observation means like an electronic endoscope;

FIG. 60 is a cross-sectional view showing a schematic arrangement of a distal-end part of the ultrasonic probe;

FIG. 61 is an explanatory view showing function of the ultrasonic probe;

FIG. 64 is a cross-sectional view showing a schematic arrangement of a distal-end part of the ultrasonic probe for the interior of the peritoneal cavity;

FIG. 65 is an enlarged view of an ultrasonic transducer at the distal-end part of the probe;

FIG. 66 is a view showing a state in which the ultrasonic probe for the interior of the peritoneal cavity is inserted into the peritoneal cavity;

FIG. 67 is an explanatory view showing function of the ultrasonic probe for the interior of the peritoneal cavity;

FIG. 68 is an explanatory view showing an example in which an ultrasonic transducer different in structure or construction is mounted on the distal-end part of the ultrasonic probe for the interior of the peritoneal cavity;

FIG. 69 is an explanatory view showing function of the ultrasonic probe in which an ultrasonic transducer different in structure is mounted on the distal-end part of the ultrasonic probe for the interior of the peritoneal cavity;

FIG. 70 is an explanatory view showing scanning of the ultrasonic transducer;

FIG. 75 is an enlarged view showing an arrangement of a rotary detection part;

FIG. 76 is a circuit view showing the rotary detection part;

FIG. 78 is a view showing the relationship between an electrostatic motor and the therapeutic ultrasonic transducer which is fixedly mounted on a drum;

FIG. 79 is a view showing a state in which the therapeutic ultrasonic transducer is scanned in sector;

FIG. 81 is a view showing an another arrangement example of the therapeutic ultrasonic transducer;

FIG. 82 to FIG. 85 relate to a twenty-ninth embodiment of the invention, FIG. 82 being a view showing a schematic arrangement of a distal-end part of an ultrasonic probe in the twenty-ninth embodiment;

FIG. 83 is a view showing a state in which a focusing point of a therapeutic ultrasonic transducer is adjusted;

FIG. 85 is a view showing a summary of a whole arrangement of the ultrasonic probe;

FIG. 86 to FIG. 88 relate to a thirty embodiment of the invention, FIG. 86 being a view showing focusing-point adjusting means of a therapeutic ultrasonic transducer;

FIG. 90 is a view showing another arrangement of the distal-end part of the ultrasonic probe;

FIG. 91 is view showing the other arrangement of the distal-end part of the ultrasonic probe;

FIG. 92 is a view showing a state at the time changed over to a therapeutic ultrasonic transducer different in focusing point, which is arrangeed at the distal-end part of the ultrasonic probe;

FIG. 93A to FIG. 94 relate to a thirty-second embodiment of the invention, FIG. 93A being a view showing a schematic arrangement of a distal-end part of an ultrasonic probe in the thirty-second embodiment;

FIG. 94 is a cross-sectional view showing a transducer unit of an another arrangement example;

FIG. 95B is a view showing a state in which a thickness of an acoustic lens is increased to change a focal point; and FIG. 95C is a view showing a state in which a thickness of an acoustic lens is decreased to change a focal point.

DETAILED DESCRIPTION OF THE PREFERRED EMBODIMENTS

Figure 1:
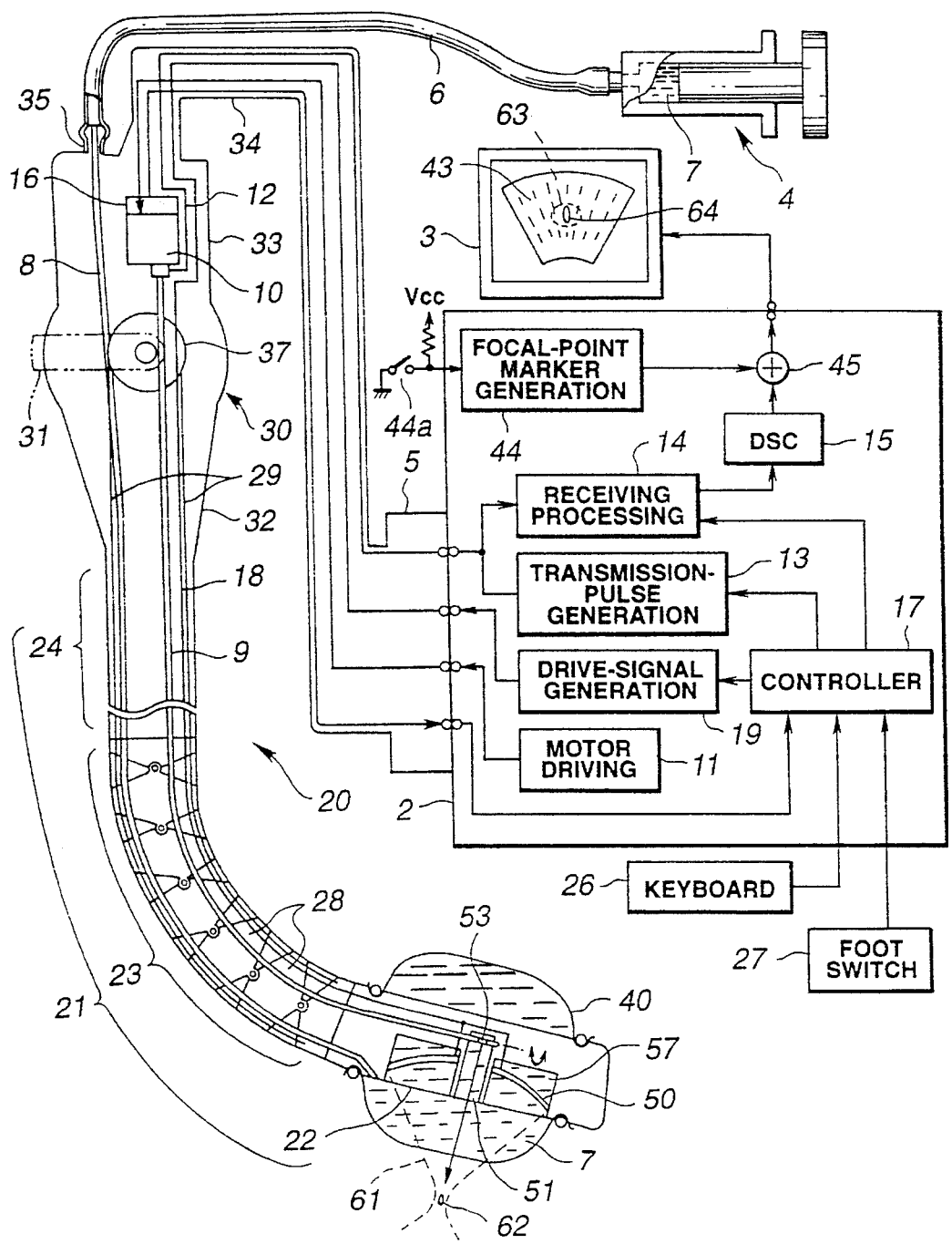

As shown in FIG. 1, an ultrasonic diagnosis and therapy system 1 according to a first embodiment of the invention comprises an ultrasonic probe 20 which is provided with ultrasonic observation and treatment or therapy means (having an observation ultrasonic vibrator or transducer 53 and a therapeutic ultrasonic transducer 50) for conducting observation and therapy due to an ultrasonic wave, an ultrasonic diagnosis and therapy (treatment) device 2 having built therein signal processing means for conducting signal processing with respect to the observation ultrasonic transducer 53 which is built in the ultrasonic probe 20 and drive means for driving the therapeutic ultrasonic transducer 50, a color monitor 3 serving as display means for displaying an ultrasonic image signal which is generated by signal processing with respect to the observation ultrasonic transducer 53, and a transfer-medium injector 4 for supplying an ultrasonic transfer medium to a balloon 40 which is detachable with respect to a distal-end part 22 of the ultrasonic probe 20.

Figure 2A:
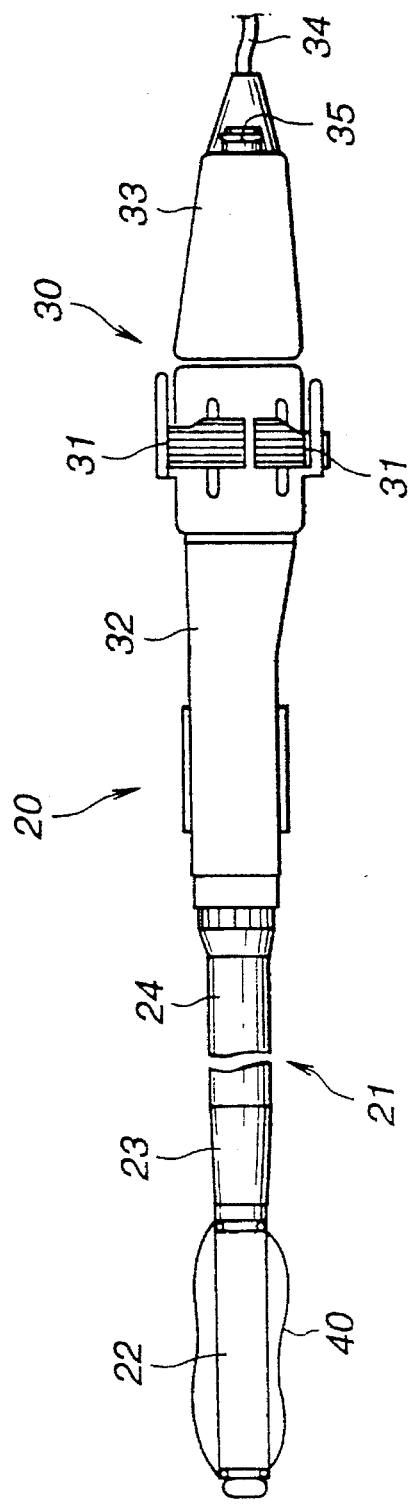
FIG. 2A and FIG. 2B are a top plan view and a side elevational view, respectively, showing an outer appearance of an ultrasonic probe in the first embodiment.
Figure 2B:
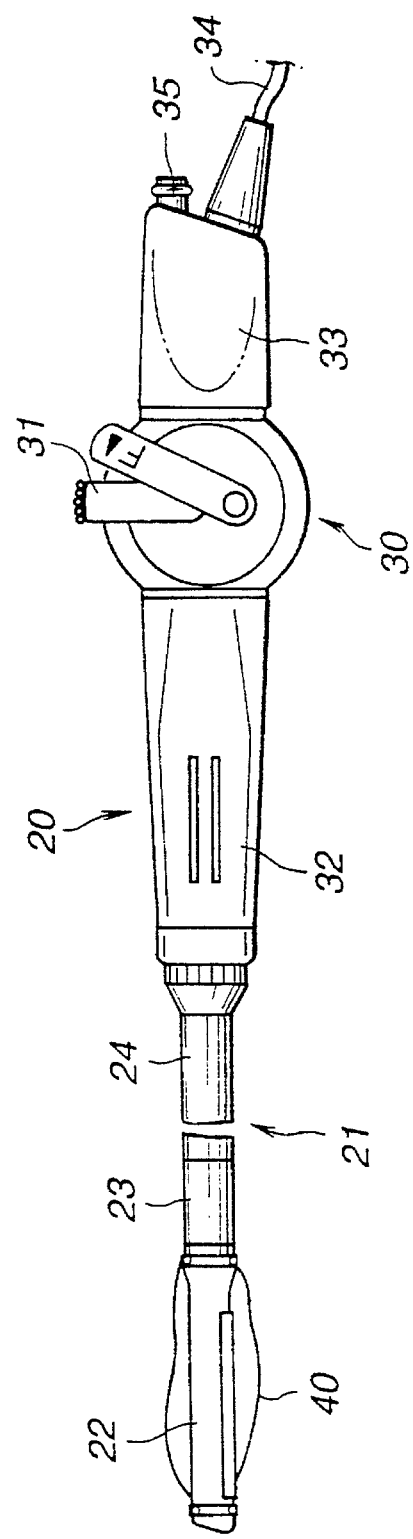

As shown in FIG. 2A and FIG. 2B, the ultrasonic probe 20 comprises a thin tubular insertion part 21 so as to be capable of being inserted into an internal coelom, a first grip part 32 which is formed adjacent at a rear part of the insertion part 21 and which is gripped by an operator, an operation part 30 wide in width, which is formed adjacent in rear of the grip part 32 and which conducts curvature operation, a second grip part 33 formed adjacent in rear of the operation part 30, and a code 34 which extends from the grip part 33. As shown in FIG. 1, the arrangement can be such that a connector 5 which is provided at an end of the code 34 is detachably connected to the ultrasonic diagnosis and therapy device 2.

The insertion part 21 in the present embodiment is formed by the distal-end part 22 having built therein an observation ultrasonic transducer and a therapeutic ultrasonic transducer of concave focusing type, a bendable curvature part 23 formed adjacent to a rear end of the distal-end part 22, and an elongated rigid insertion tube 24 extending from a rear end of the curvature part 23 to a front end of the first grip part 32.

A curvature operation knob 31 which is provided at the operation part 30 is so operated as to be moved angularly, whereby the curvature part 23 can be curved in any of upper- and lower-hand and left- and right-hand optional directions.

Further, the balloon 40 which encloses therein an ultrasonic transfer medium 7 performing an acoustic coupling is capable of being mounted to the distal-end part 22. The ultrasonic transfer medium 7 is capable of being injected from the injector 4 through a tube 6 which is connected to an injection port 35 provided at the second grip part 33. The arrangement is such that the transfer medium 7 which is injected into the injection port 35 is supplied into the balloon 40 through a line 8 within the ultrasonic probe 20.

A signal line 12 which is connected to the observation ultrasonic transducer 53 is inserted into the insertion part 21, for example, into a shaft 9. The signal line 12 extends to the outside of the shaft 9 at a rotational support part at a rear end of the shaft 9. The signal line 12 is connected to a transmission-pulse generator circuit 13 and a signal-receiving processing circuit 14 within the ultrasonic diagnosis and therapy device 2, through the interior of the code 34. The transmission-pulse generator circuit 13 generates transmission pulses for outputting (wave-sending) an observation ultrasonic wave, and applies the same to the observation ultrasonic transducer 53 through the signal line 12, to thereby excite the observation ultrasonic transducer 53 to output the observation ultrasonic wave radially.

The ultrasonic wave which is reflected by a part different in acoustic impedance and which is received by the observation ultrasonic transducer 53 is converted to an electric signal by the observation ultrasonic transducer 53. The ultrasonic wave is processed in signal by the signal-receiving processing circuit 14 through the signal line 12 so as to be converted to an image signal. The image signal is converted to a standard image signal by a digital scanning converter (hereinafter, referred simply to as "DSC") 15, and is inputted to the color monitor 3. Thus, an ultrasonic tomography or ultrasonogram image 43 is displayed on a display plane of the color monitor 3.

Further, a focal-point marker generator circuit 44 for displaying a focal-point marker 64 to an image position which corresponds to a focusing position (or a focusing point) 62 of the therapeutic ultrasonic transducer 50 is provided within the ultrasonic diagnosis and therapy device 2. The marker signal is superimposed, by a mixer 45, onto an image signal outputted from the DSC 15 and is displayed on the display plane of the color monitor 3, together with the ultrasonic tomography image 43.

A rotary encoder 16 is mounted on a rotary shaft of a motor 10. The rotary encoder 16 detects an amount of rotation of the rotary shaft, that is, an angle of the observation ultrasonic transducer 53 in a scanning direction. An angle signal corresponding to the amount of rotation (rotational angle) which is detected by the rotary encoder 16 is inputted to a controller 17 within the ultrasonic diagnosis and therapy device 2, through a signal line within the code 34.

The controller 17 outputs a timing signal controlling timing of the transmission pulse outputted from the transmission-pulse generator circuit 13 and timing of signal processing of a signal-receiving processing circuit 14, in accordance with the angle signal.

The therapeutic ultrasonic transducer 50 of concave focusing type, which is built in the distal-end part 22 is also connected to a signal line 18 which is inserted through the insertion part 21 or the like. The signal line 18 is connected to a drive-signal generator circuit 19 within the ultrasonic diagnosis and therapy device 2.

The drive-signal generator circuit 19 generates a drive signal for driving the therapeutic ultrasonic transducer 50.

The drive signal is of a signal level larger than a signal level of the transmission pulse which drives the observation ultrasonic transducer 53. The therapeutic ultrasonic transducer 50 is made to a concave shape or form which is considerably larger than an area size of the observation ultrasonic transducer 53, and is formed such that each part of the concave shape resides on a spherical face whose radius curvature is, as a center thereof, the set focusing point.

Setting is made as follows: That is, a therapeutic ultrasonic beam which is outputted from the therapeutic ultrasonic transducer 50 having the concave shape forms a concave wave front or face and makes progress into a direction which is opposed against a concave center. With the progress, the ultrasonic beam is gradually focused. Energy of the ultrasonic beam becomes the highest at the focusing point. Accordingly, the drive signal is applied to the therapeutic ultrasonic transducer 50 under a state in which the focusing point is set to a lesion tissue, whereby it is possible to conduct the therapy treatment which cauterizes the lesion tissue by the focused ultrasonic beam to cause the same to die.

Moreover, connected to the controller 17 are a keyboard 26 and a foot switch 27, for example. Key input of level setting from the keyboard 26 is conducted whereby the level of the drive signal which is outputted from the drive-signal generator circuit 19 can be set variably.

Furthermore, the foot switch 27 is depressed so that the switch is turned ON or OFF, whereby the controller 17 can conduct outputting or outputting stop of the drive signal from the drive-signal generator circuit 19.

As shown in FIG. 1, the curvature part 23 is such that substantially ring-shaped pieces 28, 28, . . . are connected to each other for angular movement in a longitudinal direction of the insertion part 21. Wires 29 and 29 for curvature operation are fixedly mounted on the pieces 28 at the distal end by welding or the like. The wires 29 and 29 which are inserted into the insertion part 21 in rear of the curvature part 23 have their respective rearward or proximal ends thereof which are fixedly mounted on a rotary element 37 on which a proximal end of the curvature operation knob 31 is mounted.

Thus, a curvature mechanism is arranged. Operation in which the curvature operation knob 31 is moved angularly is conducted whereby the rotary element 37 is rotated. Accompanied with this rotation, one of the pair of wires 29 and 29 is pulled (or is drawn), and the other is relaxed (or is fed), so that the pair of wires 29 and 29 are moved in a retracting manner (or before and behind).

Thus, it is possible to curve the pieces 28 of the curvature part 23 toward the pulled side.

Figure 3:
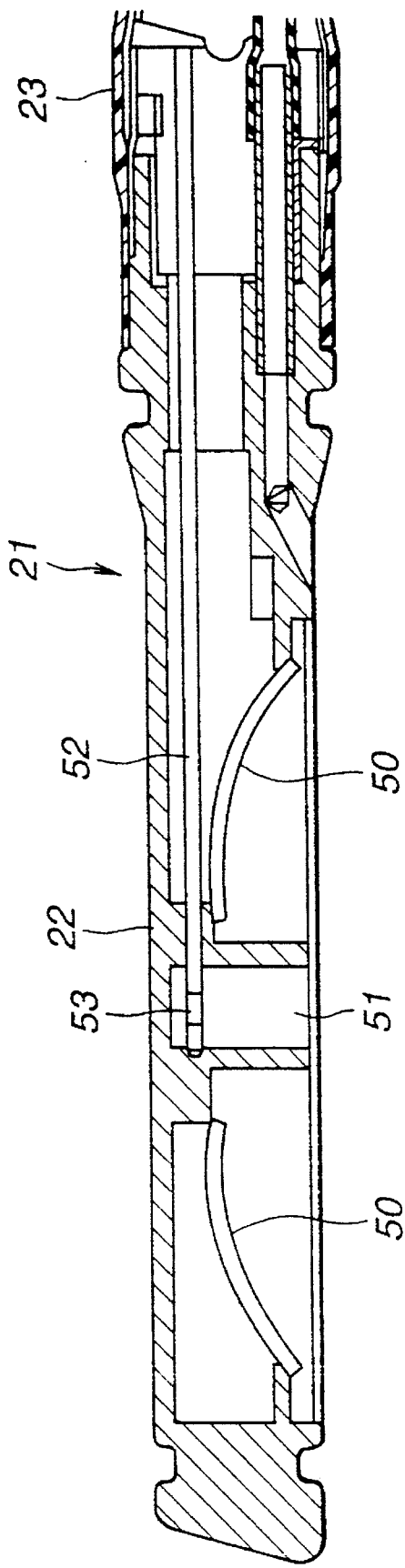

As shown in FIG. 3, in this embodiment, a general observation diameter-reduced ultrasonic probe 52 has an ultrasonic transducer portion 53' which is built in an ultrasonic-observation-means building-in part 51' which is formed substantially at a center part of the distal part 22 (in FIG. 1, it is shown by an internal structure or construction of the observation diameter-reduced ultrasonic probe 52, the observation ultrasonic transducer 53 being built in an observation-ultrasonic-transducer receiving part 51.). The therapeutic ultrasonic transducer 50 is built in each of therapeutic ultrasonic transducer receiving parts 57 on both sides of the observation ultrasonic receiving part 51.

The ultrasonic transducer portion 53 of the general observation diameter-reduced ultrasonic probe 52 is built in the ultrasonic-observation-means built-in part 51'. The observation diameter-reduced ultrasonic probe 52 is an observation probe of a mechanical sector scanning type or a mechanical radial scanning type. Furthermore, the arrangement is such that an ultrasonic transfer medium 7 is enclosed within an internal space in the distal-end part 22 against which a radiation plane of the concave focusing-type transducer 50 faces, and within the ultrasonic-observation-means built-in part 51' so that the ultrasonic wave can be sent through an ultrasonic sending window.

Further, in this embodiment, a positioning mechanism is formed so as to lock the focusing point 62 (refer to FIG. 5) such that the focusing point 62 due to the therapeutic ultrasonic transducer 50 is positioned at a predetermined position within an ultrasonic scanning range or an ultrasonic observation region range 60 (refer to FIG. 5) due to the observation ultrasonic transducer 53.

This condition or state is shown also in FIG. 1. A therapeutic ultrasonic beam 61 due to the therapeutic ultrasonic transducer 50 is focused at the focusing point 62. The observation ultrasonic wave is outputted radially from the observation ultrasonic transducer 53 as indicated by an arrow such that the focusing point 62 is included at a center of the scanning range.

Specifically, as shown in FIG. 1 or FIG. 3, the concave-type therapeutic ultrasonic transducer 50 is equally divided into two in a longitudinal direction. Divided two parts are arranged symmetrically (to the left and right in the longitudinal direction) such that a slight space is formed therebetween in the longitudinal direction, and the observation ultrasonic transducer 51 is arranged at the space portion therebetween. Mechanical positioning (or locking) of the therapeutic ultrasonic transducer 50 and the observation ultrasonic transducer 53 is previously conducted such that the focusing point 62 is positioned on a radiated line along which the ultrasonic wave is radiated at a center angle of the ultrasonic scanning range 60 due to the observation ultrasonic transducer 51, for example.

Accordingly, the focusing-point marker 64 (on the image corresponding to the focusing point 62) is displayed such that the position of the focusing point 62 can be confirmed on the ultrasonic tomographic image 43 corresponding to the ultrasonic scanning range 60, correspondingly to the relative positioning state of the observation ultrasonic transducer 53 and the therapeutic ultrasonic transducer 50 which are set mechanically.

Display/display-stop of the focusing-point marker 64 can be selected by ON/OFF of a switch 44a.

For example, in case where the display of the focusing-point marker 64 is in the way of observation of, such as, a lesion part or the like, the switch 44a is made to an OFF condition, whereby the focusing-point marker 64 is not displayed.

In connection with the above, the observation ultrasonic transducer 53 and the therapy combined ultrasonic transducer 50 can be formed by structures substantially the same as cross-sectional structures of the reference numerals 97 and 95 in FIG. 23B to be described subsequently.

Since the present embodiment is of structure that the observation ultrasonic transducer 53 and the therapy combined ultrasonic transducer 50 can simultaneously be operated, it is desirable that frequencies of signals which drive respective transducers are set to different frequencies. Normally, the frequency of a signal which drives the observation ultrasonic transducer 53 is set higher than the frequency of a signal which drives the therapeutic ultrasonic transducer 50, in order to acquire an image which is high in resolution, by the observation ultrasonic transducer 53.

A drive frequency of the observation ultrasonic transducer 53 is 12 MHz, for example, and a drive frequency of the therapeutic ultrasonic transducer 50 is set less than 2 !A12 Mz, for example.

Figure 4:
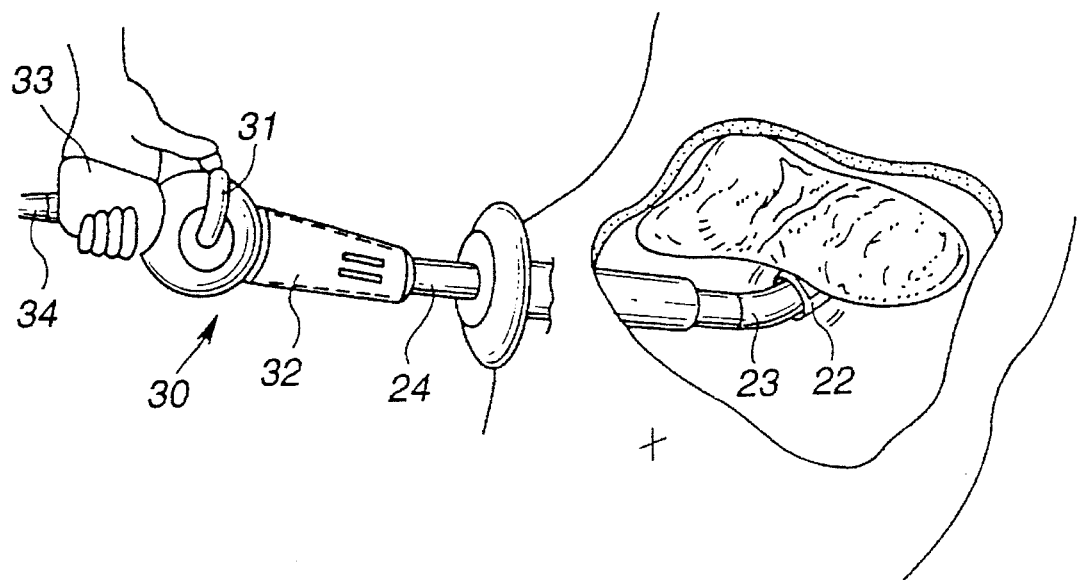

As shown in FIG. 4, the ultrasonic probe 20 arranged as described above is inserted into a peritonealized peritoneal cavity through a trocar, and the distal-end part 22 is in contact with a face of an internal organ to be treated while conducting the curvature operation. Subsequently, the transmission pulse from a transmission-pulse generator circuit 13 of the ultrasonic diagnosis and therapy device 2 is applied to the observation ultrasonic transducer 53 of the observation diameter-reduced ultrasonic probe 52 to output the observation ultrasonic wave toward the internal organ.

Figure 5:
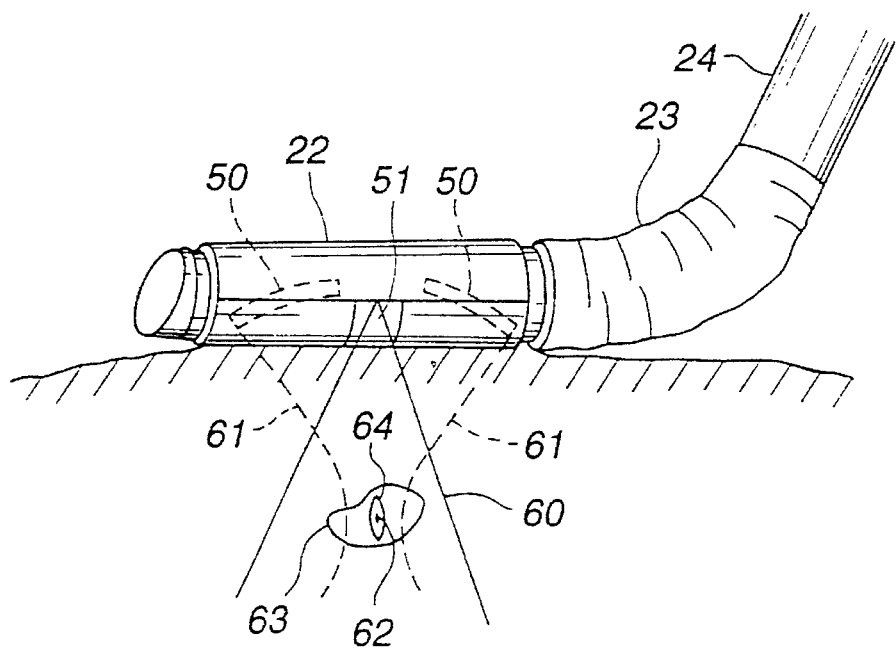

In this case, the observation ultrasonic transducer 53 is reciprocally rotated within the angle which is, for example, set by the motor 10, whereby the ultrasonic wave is intermittently radiated within an ultrasonic observation region range, indicated by the reference numeral 60 in FIG. 5. Reflected ultrasonic wave is received by the observation ultrasonic transducer 53, so as to be converted to an electric signal. A signal which is transmitted and received within the ultrasonic observation region range 60 is processed in signal by the signal-receiving processing circuit 14. As shown in FIG. 1, the signal passes through the DSC 15 and is depicted on the display plane of the color monitor 3, as a tomographic image of the interior of the internal organ due to the ultrasonic wave, that is, as an ultrasonic tomographic image 43.

The distal-end part 22 is moved, the curvature part 23 is curved, or the like, such that the lesion part 63 is depicted on the ultrasonic diagnosis image 43. If the condition becomes a condition under which the lesion part 63 is depicted on the ultrasonic diagnosis image 43, curvature of the curvature part 23, positional adjustment of the distal-end part 22 or the like is so conducted that the focusing-point marker 64 which is displayed in superimposition on the diagnosis image 43 so as to be in agreement with the position of the lesion part or to overlapped thereagainst to conduct positional setting.

After the positional setting, a therapeutic focusing ultrasonic wave having a required strength is irradiated from the therapeutic ultrasonic transducer 50, by the drive-signal generator circuit 19. The focusing-point marker 64 is so set as to be displayed on a predetermined position (that is, the focusing point of the therapeutic ultrasonic wave) within the scanning range. Since the predetermined position is locked mechanically to the focusing point of the therapeutic ultrasonic wave, the ultrasonic wave is focused at a position of the lesion part which corresponds to the focusing-point marker 64 in case where the therapeutic focusing ultrasonic wave is outputted.

The lesion part 63 of the focusing point abruptly rises in temperature by the therapeutic ultrasonic wave having high strength or intensity so that the lesion tissues can be cauterized.

The therapeutic ultrasonic wave having high strength is irradiated until denaturation of protein proceeds which is required only to cause doubtful or uncertain death of the lesion tissues proceeds, while observing a condition of the denaturation of protein of the tissues due to this cauterization on the ultrasonic diagnosis image 43.

Subsequently, the irradiation of the therapeutic ultrasonic wave having high intensity stops, or the degree of achievement of therapy is confirmed on the ultrasonic diagnose image 43 during irradiation. In case of insufficiency, additional irradiation continues. In case where irradiation is necessary to another portions, therapy continues in a manner similar to that described above. Thus, all therapy is completed.

In this manner, according to the first embodiment of the invention, it is possible to acquire also the observation image by scanning of the observation ultrasonic wave under a condition in which the focusing point of the therapeutic ultrasonic wave is locked to a predetermined position within the scanning range of the observation ultrasonic wave. Accordingly, it is possible to easily conduct the therapeutic operation.

It is also possible to acoustically observe the condition in the course of therapy. Thus, it is possible to realize a system which is easy to conduct therapy by an adequate amount of irradiation.

Moreover, it is naturally possible to acoustically confirm whether or not the ultrasonic wave which is outputted from the therapeutic ultrasonic wave is focused at the object part to be treated.

Accordingly, it is easy also to prevent the ultrasonic wave from being erroneously focused to peripheral parts. Thus, it is possible to secure safeness.

Although the description has been made with reference principally to FIG. 1, this condition or aspect is also shown in FIG. 5 in a trial manner. As shown in FIG. 5, after a lesion part 63 has been caught into an ultrasonic observation range 69, the position of the ultrasonic prove 20 is set by curvature operation or the like, with reference to a focusing-point marker 64 which is displayed on the ultrasonic diagnosis image 43 and the ultrasonic image of the lesion part 63, such that the focusing point 62 within the therapeutic ultrasonic beam 61 due to the therapeutic ultrasonic transducer 50 is positioned at the lesion part 63.

After the positioning of the focal point has been completed, the therapeutic focusing ultrasonic wave having the required strength is irradiated from the concave focusing-type transducer 50 by the drive-signal generator circuit 19. The tissues of the lesion part 63 is cauterized by the therapeutic ultrasonic wave having the high strength.

According to the first embodiment, it is possible to conduct the ultrasonic high-temperature therapy by the ultrasonic probe having the ultrasonic observation function and the ultrasonic high-temperature therapy function, and the insertion and curvature functions, under a condition in which the ultrasonic probe is inserted into the peritoneal cavity so that the ultrasonic therapy image of the deep internal organ is procured.

More specifically, since the ultrasonic probe is provided with the bendable curvature part, the observation ultrasonic transducer and the therapeutic ultrasonic transducer, on the distal-end side of the elongated insertion part, the curvature part is curved whereby it is possible to easily conduct setting to a state capable of irradiating the observation ultrasonic wave and the therapeutic ultrasonic wave to the side of the cauterization object part.

Furthermore, the arrangement is such that locking is made such that the focusing point of the therapeutic ultrasonic wave is positioned at the predetermined position within the ultrasonic scanning range due to the observation ultrasonic wave, and the observation ultrasonic wave is scanned under this locked condition so that the observation ultrasonic image can be acquired. Accordingly, if the cauterization object part such as the lesion part or the like is set to the predetermined position within the scanning range, a condition can be maintained in which the focused ultrasonic wave can be so secured as to be irradiated to the object part in case where the therapeutic ultrasonic wave is irradiated.

Moreover, in order to facilitate to confirm this condition or aspect, the focal-point marker can be displayed on the predetermined position within the scanning range at which the focusing point is positioned. Accordingly, the cauterization object part such as the lesion part or the like is set to the position of the focal-point marker so that the part can be cauterized by irradiation of the therapeutic ultrasonic wave, and the condition of the part can easily be observed on the ultrasonic diagnosis image. Thus, it is easily possible to conduct therapy and disposition or treatment by the adequate cauterization amount.

Moreover, the focal-point marker can be displayed such that the focusing point of the therapeutic ultrasonic wave is displayed on the predetermined position on the ultrasonic therapy image due to the observation ultrasonic wave. Accordingly, it is possible to set the cauterization object part such as the lesion part or the like to the position of the focal-point marker to cauterize the part by irradiation of the therapeutic ultrasonic wave, and it is possible to observe the condition of the part on the ultrasonic diagnosis image.

Accordingly, it is easily possible to conduct the therapy and treatment by the adequate cauterization amount.

Figure 6:
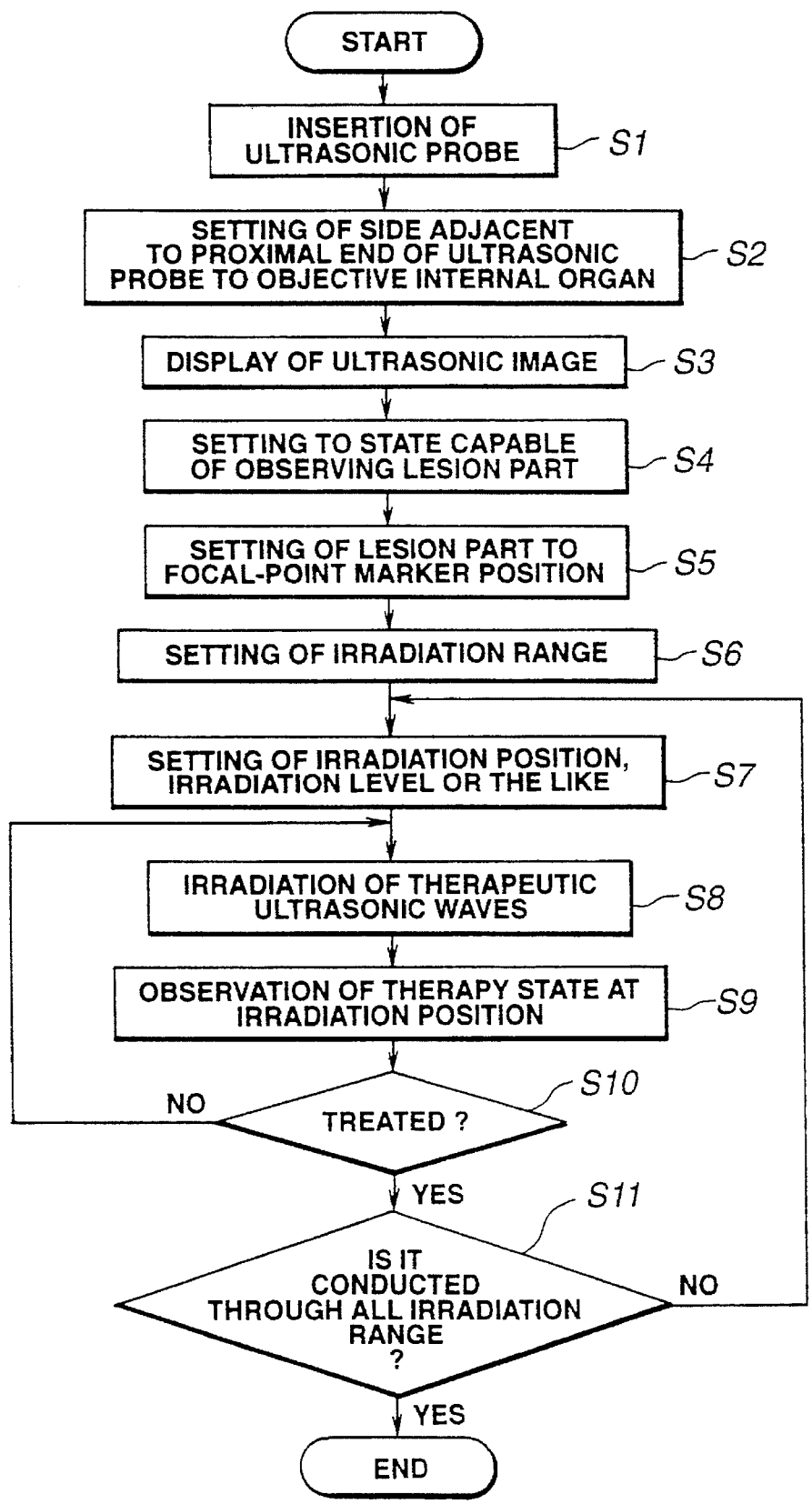

An example of the therapy method due to the system 1 according to the first embodiment is shown in FIG. 6. In this case, it is assumed that the lesion part which is formed on an object internal organ, for example, is treated by irradiation of the therapeutic ultrasonic wave.

First, as shown in Step S1, the ultrasonic probe 20 is inserted into the coelom. For example, in case where the ultrasonic therapy with respect to the internal organ within the peritoneal cavity is conducted, the trocar is pierced into or inserted into the abdomen, and the ultrasonic probe 20 is inserted from the side of the distal end thereof with the trocar serving as a guide. In this case, an endoscope (not shown) is also pierced with the pierced bore due to the trocar serving as a guide, in order to introduce or lead the distal-end side of the pierced ultrasonic probe 20 into the object internal organ.

Subsequently, as shown in Step S2, the distal-end side of the ultrasonic probe 20 is led to a location in the vicinity of the object internal organ.

Under the observation of the endoscope, the distal-end side of the ultrasonic probe 20 which is inserted into the peritoneal cavity is led to the location in the vicinity of the object internal organ, and is further in intimate contact with the location in the vicinity of the object internal organ.

In this case, there are many cases where it is difficult to cause the balloon 40 portion on the side of the ultrasonic transmission and receiving window of the distal-end part 22 of the ultrasonic probe 20 under the condition merely inserted straight into intimate contact with the position in the vicinity of the object internal organ, because other internal organs, ossa or the like interfere with or obstruct.

For this reason, operation in which the curvature operation knob 31 on the side of a grip for an operator of the ultrasonic probe 20 is moved angularly is conducted whereby the curvature part 23 on the distal-end side is curved. Thus, there are many cases where it is made possible to be into intimate contact with the object internal organ or the position in the vicinity thereof.

Subsequently, as shown in Step S3, the ultrasonic therapy image is displayed on the monitor 3, by scanning of the observation ultrasonic transducer 53.

Figure 7:
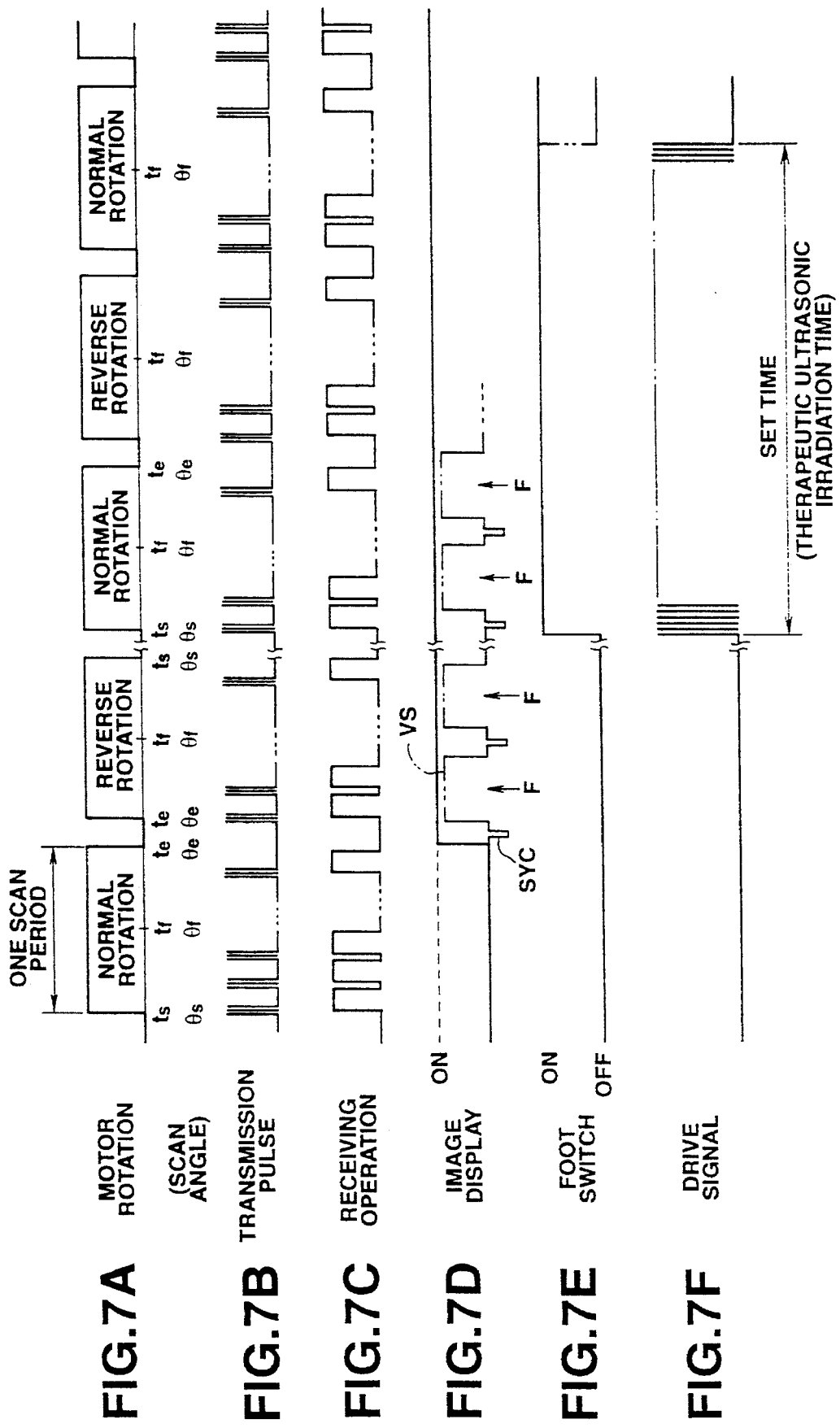

As shown in FIG. 7A, the motor 10 is rotated to scan the observation ultrasonic transducer 53. A duration of an H-level in FIG. 7A shows a state in which the motor 10 is rotated. During the duration, the observation ultrasonic transducer 53 is rotated through an angle corresponding to the predetermined scanning range (a single or one scanning duration is shown in FIG. 7A). Moreover, the present embodiment adopts a scanning mechanism in which, after the motor 10 has been rotated (been normally rotated) only through an angle corresponding to the scanning range, in the clockwise direction, for example, the motor 10 stops, and the motor 10 is this time rotated in a reverse direction.

In each of the scanning angles which are rotated through minute angles, the transmission pulses as shown in FIG. 7B are applied to the ultrasonic transducer 53 to output the ultrasonic wave in the form of pulses.

After each of the transmission pulses has been outputted, as shown in FIG. 7C, the receiving processing circuit t4 is set to a receiving operation state (time at receiving operation is shown by the H-level), and processing is conducted which receives the reflected ultrasonic wave to generate the image signal with respect to the object internal organ. In this case, a signal corresponding to the reflected ultrasonic wave is stored in a frame memory (not shown), and is converted to an image signal after the operation in which the signals in the whole scanning range have been stored, to display an ultrasonic diagnostic image on the monitor 3. As shown in FIG. 7D, after initial scanning, it is possible to always conduct image display. Time through which the scanning range is once scanned is longer than a normal one frame period (1/30 S) or one field period (1/60) and, accordingly, the same image which is stored in a frame memory (not shown) is displayed till display of an image due to the subsequent scanning.

FIG. 7A shows the following condition or state. That is, the below in FIG. 7A shows an end time te of the scanning from a start time ts of the scanning, and a scanning angle θs and θe corresponding thereto, and also shows a scanning angle θf corresponding to a scanning time tf at which the ultrasonic wave is scanned in a scanning direction in which the focusing point of the therapeutic ultrasonic wave exists. The scanning angle θf is always locked to a position of a constant angle from the angle θs of the scanning start.

Specifically, the scanning angle θf shows a scanning direction in which the focusing point exists. The focusing point exists at a predetermined position on the scanning direction.

Subsequently, as shown in Step S4, the state is made to a state capable of observing the lesion part (a state in which the lesion part enters the scanning range). Further, the distal-end side of the ultrasonic probe 20 is moved, the curvature part 23 is curved, or the like, to modify the outputting direction of the observation ultrasonic wave, or the like, toward the side of the object internal organ, to successively conduct scanning in a manner of three-dimension. Thus, the state is made to a state under which the lesion part in the object internal organ can be observed on the ultrasonic diagnosis image.

After having become the state under which the lesion part can be observed within the scanning range, as shown in Step S5, the lesion part is subsequently set to the focal-point marker position. Since the focusing point of the therapeutic ultrasonic wave is set to the position where the focal-point marker within the scanning range is displayed, positioning adjustment is conducted by movement of the probe, curvature of the curvature part 23, or the like, in such a manner that the state becomes a positioning state under which the position where the lesion part is observed is in agreement with the focusing point.

Subsequently, setting of the irradiation range in Step S6, and setting of the irradiation position, the irradiation level (irradiation strength) and the amount of irradiation (irradiation time) in Step S7 are conducted. If the region of the lesion part to be conducted in therapy is substantially the same in size as the focusing point, the state should be set to a state under which a center of the region of the lesion part is in agreement with the focusing point, even if the setting of the irradiation range is not conducted. However, in case where the region of the lesion part is larger than the focusing point, setting of the irradiation range which covers this region is conducted. Irradiation of the therapeutic ultrasonic wave is conducted while the irradiation position is shifted a little by a little.

For this reason, if the irradiation range is set, the irradiating irradiation position is first set. Specifically, setting is made such a position that the irradiation position is overlapped with the position of the focal-point marker.

Furthermore, the level, or the strength, or the amplitude of the therapeutic ultrasonic wave is set, and the irradiation amount or the irradiation time is set.

After having conducted these settings, as shown in Step S8, irradiation of the therapeutic ultrasonic wave is subsequently conducted. Even in case where the set time has elapsed, it is possible to acquire the ultrasonic image substantially at a real time by the observation ultrasonic wave. Accordingly, it is possible to confirm whether or not the focusing point is in agreement with the irradiation position.

If it is confirmed as being in agreement with each other, the foot switch 27 is depressed to conduct irradiation of the therapeutic ultrasonic wave. As shown in FIG. 7D, when the foot switch 27 is turned ON, the drive signal from the drive-signal generator circuit 19 (refer to FIG. 7F) is applied to the therapeutic ultrasonic transducer 50, and the therapeutic ultrasonic wave is outputted.

In case where the irradiation amount or the irradiation time is set, the controller 17 does not output the drive signal from the drive-signal generator circuit 19 if the set irradiation amount or the set irradiation time is reached.

Subsequently, as shown in Step S9, the therapy state or condition at the irradiation position is observed by the ultrasonic image. As shown in Step S10, judgment as to whether or not sufficient therapy is done is conducted. In case where irradiation of the ultrasonic wave is insufficient, the program is returned to Step S8, and irradiation of the therapeutic ultrasonic wave is again conducted. In this case, this may be done after the level of the therapeutic ultrasonic wave and the level of the irradiation amount thereof have been set, or irradiation of the therapeutic ultrasonic wave may be conducted only through time through which the foot switch 27 is depressed while maintaining the previous level.

Meanwhile, in case of having become a sufficiently treated state, the program is returned to Step S7 by judgment as to whether the ultrasonic irradiation is conducted with respect to all the therapy range shown in Step S11. In Step S11, the irradiation position is shifted to similarly conduct the therapy treatment by irradiation of the therapeutic ultrasonic wave.

In this case, the foot switch 27 may be depressed after having again set the level and the irradiation amount of the therapeutic ultrasonic wave, to conduct irradiation of the therapeutic ultrasonic wave, or it may conduct irradiation of the therapeutic ultrasonic wave under a state of the previous level and the previous irradiation amount. The therapy state of the irradiation position is observed by the ultrasonic image, and the therapy and treatment are conducted.

In this manner, it is possible to complete the therapy and treatment due to irradiation of the ultrasonic wave with respect to all the therapy range.

In the present embodiment, the focusing point of the therapeutic ultrasonic wave is set or is locked to the predetermined position within the scanning range of the observation ultrasonic wave, and this state is always maintained. Further, as will be seen from comparison between FIG. 7A to FIG. 7C and FIG. 7F, it is possible to simultaneously conduct operation due to the scanning of the observation ultrasonic wave and operation of outputting of the therapeutic ultrasonic wave. Moreover, the position F of the focusing point in the image signal VS which is diagrammatically shown by two-dot-and-chain lines in FIG. 7D is locked to a constant position with respect to a synchronous signal SNC. Accordingly, such lock means or a lock mechanism is formed that the focusing point F is locked to the constant position even on the ultrasonic image.

Moreover, in the above-described flow chart, it has been described that it is possible to observe the state of the irradiation position by the ultrasonic image after having irradiated the therapeutic ultrasonic wave. Since, however, the ultrasonic image can always be acquired, it is also possible to observe the state during irradiation of the therapeutic ultrasonic wave.

Figure 8:
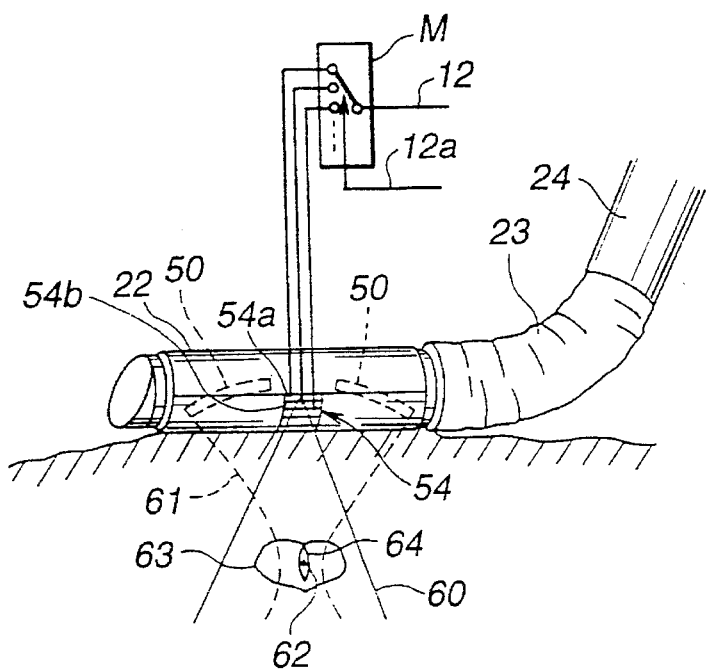
FIG. 8 is a view showing a distal-end part of an ultrasonic probe in a second embodiment of the invention.

A second embodiment of the invention will subsequently be described. FIG. 8 is a view showing a principal portion of the second embodiment, and the same or identical reference numerals are shown as being applied to constitutional elements the same as or corresponding to those of the first embodiment shown in FIG. 5. The embodiment is arranged such that ultrasonic observation means which is mounted on the distal-end part 22 of the ultrasonic probe 20 is an electronic radial-array-type ultrasonic transducer 54.

The electronic radial-array-type ultrasonic transducer 54 is formed by an ultrasonic transducer array in which a plurality of transducer elements 54a, 54b, . . . are arranged in the form of a belt along a cylindrical face. The transducer elements 54a, 54b, . . . are connected to the transmission-pulse generator circuit 13 and the receiving processing circuit 14 through a multiplexer M and the signal line 12.

Furthermore, a control-signal line 12a which conducts change-over of a contact of the multiplexer M is connected to the controller 17 in FIG. 1, and various contacts are successively changed over at constant time intervals.

Drive signals each in the form of pulse from the transmission-pulse generator circuit are successively applied to the transducer elements 54a, 54b, . . . through the multiplexer M, whereby the observation ultrasonic wave is outputted in directions within the scanning range in the form of a sector in a plane which extends perpendicularly to a shaft having the cylindrical face.

Ultrasonic reflected signals outputted in the form of pulse are received respectively by the transducer elements 54a, 54b, . . . The ultrasonic reflected signals conduct processing similarly to case of mechanical sector scanning with respect to ultrasonic signals which are converted to electric signals, and the ultrasonic image is displayed on the monitor.

The second embodiment can acquire functional advantages similar to those of the first embodiment.

Further, since no shift in the image position which is peculiar to the mechanical scanning does not occur, the second embodiment has advantages that positioning of the focal point to the lesion part on the ultrasonic diagnosis image becomes extremely accurate. That is, without the fact that the transducer is mechanically rotated, the fixed transducer elements are merely electrically driven successively, whereby the ultrasonic wave is scanned.

Accordingly, it is possible to eliminate or solve such a phenomenon that scannings which should originally be the same in scanning direction in case of the mechanical scanning are slightly shifted from each other and, therefore, shift of the image occurs.

Figure 9:
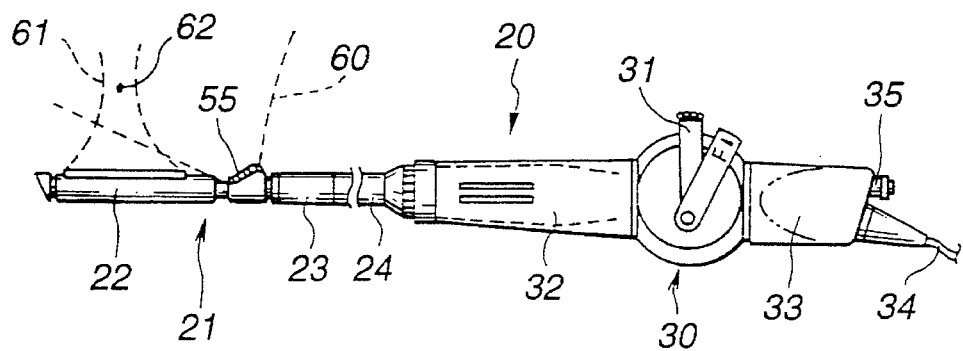
FIG. 9 is a side elevational view showing a third embodiment of the invention.

A third embodiment will subsequently be described. FIG. 9 shows the third embodiment.

The same or identical reference numerals are applied to constitutional elements the same as or corresponding to those of the first embodiment shown in FIG. 2A and the like, and the same constitutional elements are shown.

In the present embodiment, a therapeutic concave focusing-type transducer (omitted from being shown) is built in the distal-end part 22 of the ultrasonic probe 20, similarly to the previous first and second embodiments. A convex-type ultrasonic transducer array 55 serving as the observation ultrasonic transducer is provided between the distal-end part 22 and the curvature part 23.

The convex-type ultrasonic transducer array 55 is formed by a transducer array in which a plurality of ultrasonic transducer elements are arranged in the form of a belt, along a convex face. In FIG. 9, the transducer array is arranged in a plane which includes an axis of the distal-end part 22 or a longitudinal direction, for example. The arrangement is such that the plurality of elements are driven through a delay circuit element or the like, whereby the ultrasonic wave is outputted to a scanning range shown in FIG. 9.

An ultrasonic observation region 60 of the ultrasonic transducer array 55 is offset toward a direction of the distal-end part 22, that is, in the form of a forward strabismus type. Accordingly, it is possible to catch a focusing point 62 of a focusing ultrasonic beam 61 due to a therapeutic focusing-type transducer of the distal-end part 22, into the ultrasonic diagnosis image, to display a mark thereof on the diagnosis image.

Thus, according to the present embodiment, it is possible to provide means for conducting the ultrasonic therapy and means for conducting the ultrasonic observation, in separation, on the distal-end part. Accordingly, in addition to advantages that the arrangement of the distal-end part of the ultrasonic probe is simplified, it is possible to acquire also advantages that an opening diameter of the therapeutic concave focusing-type transducer is increased to further increase or strength the ultrasonic strength for the ultrasonic high-temperature therapy, to further improve the therapy efficiency.

Figure 10:
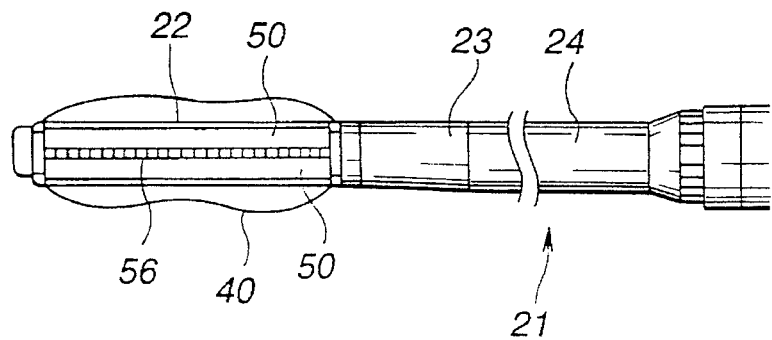
FIG. 10 is a view showing a distal-end part in a fourth embodiment of the invention.

A fourth embodiment will subsequently be described. FIG. 10 is a view showing a principal portion of the fourth embodiment. The same or identical reference numerals are applied to constitutional elements the same as or corresponding to those of the first embodiment shown in FIG. 2A and the like, and the constitutional elements are shown. In the present embodiment, an electronic linear scanning ultrasonic transducer array 56 is provided which is formed such that a plurality of transducer elements are arranged in the form of a belt, on the center axis of the distal-end part 22 of the ultrasonic probe 20 or on a plane which is in parallel to the central axis. Therapeutic concave focusing-type transducers 50 are provided on both sides thereof.

This electronic linear scanning ultrasonic transducer array 56 is driven by a method similar to that which has been described with reference to FIG. 8, for example, whereby the electronic linear scanning ultrasonic transducer array 56 can linearly be scanned in a direction perpendicularly to the sheet of paper of FIG. 10.

Also by the arrangement illustrated in FIG. 10, fundamental functional advantages are the same as those of the first embodiment. Moreover, similarly to case where, in the second embodiment, the ultrasonic observation means is made to the electronic radial scanning type transducer, the present embodiment has merits similarly to those of case where the therapeutic and diagnostic transducers are combined with each other at the distal-end part.

Figure 11:
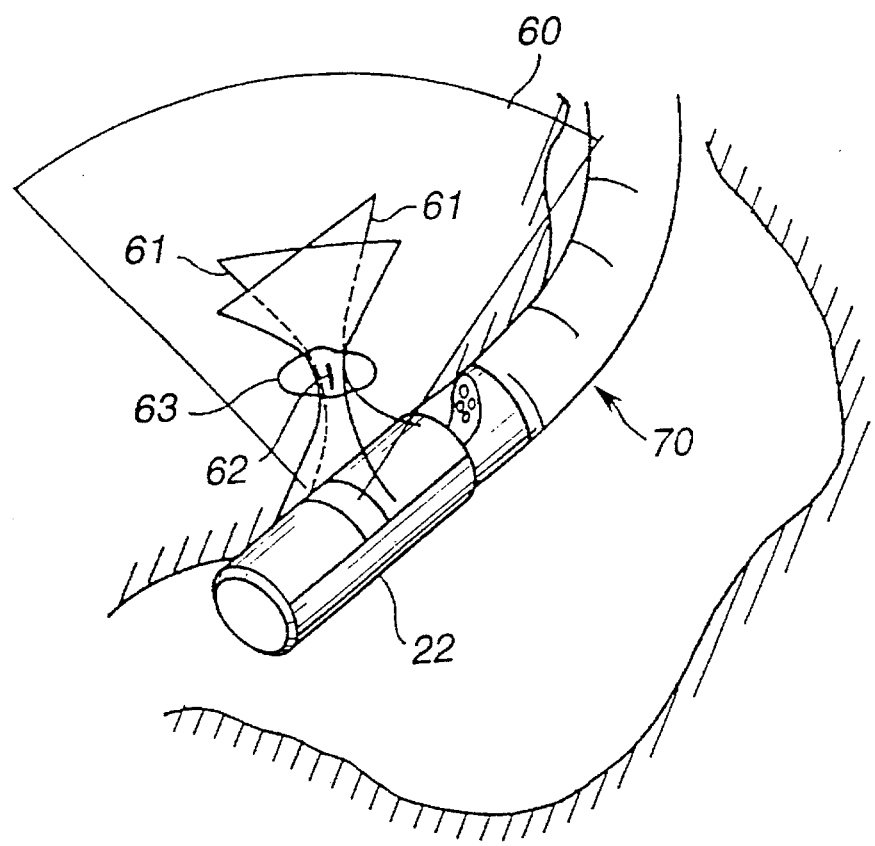
FIG. 11 to FIG. 16 relate to a fifth embodiment of the invention, FIG. 11 being a diagrammatic view showing a using state of the fifth embodiment.

A fifth embodiment will subsequently be described. FIG. 11 is a diagrammatic view showing a using state of the fifth embodiment. The embodiment is directed to an ultrasonic endoscope 71 which is formed such that the distal-end part 22 of the ultrasonic probe 20 illustrated in the first–fourth embodiments is combined with the distal end of a flexible or soft endoscope 70 which has a forward strabismus optical system.

Figure 12:
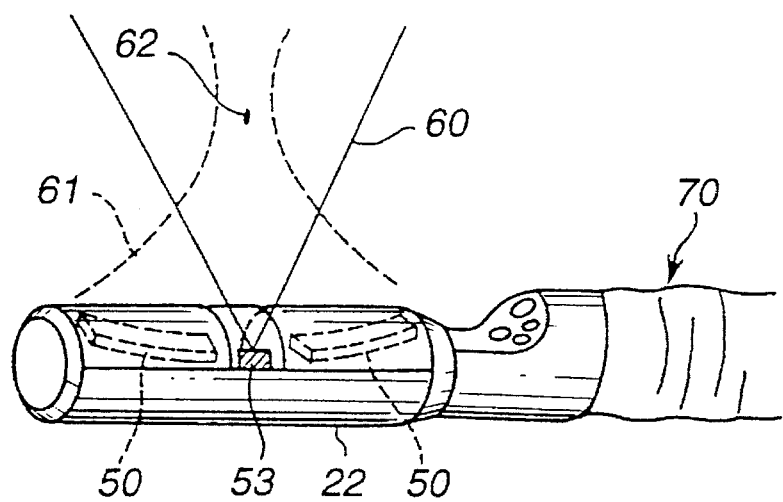
Figure 13:
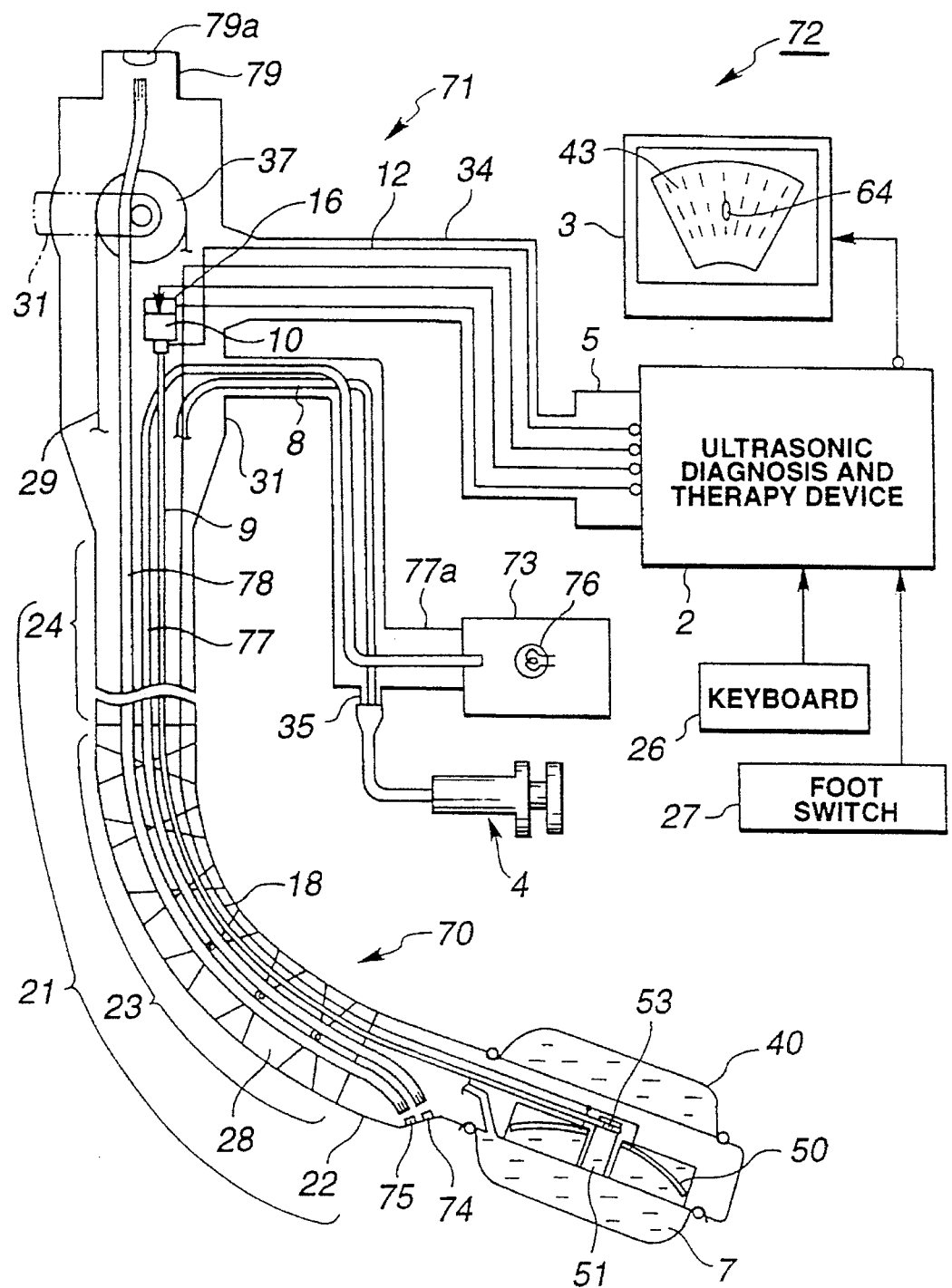

For example, FIG. 12 shows an arrangement on the side of a distal end of an ultrasonic endoscope 71 which is of structure in which the distal-end part 22 of the ultrasonic probe 20 illustrated in the first embodiment is provided on the side of a distal end of a flexible endoscope 70 having a forward strabismus optical system. FIG. 13 shows an ultrasonic diagnosis and therapy (treatment) system 72 which uses the ultrasonic endoscope 71.

The ultrasonic diagnosis and therapy system 72 in FIG. 13 is arranged such that, in the ultrasonic diagnosis and therapy system 1 in FIG. 1, the ultrasonic endoscope 71 is used in place of the ultrasonic probe 20, and a light source device 73 for supplying illumination light to a light guide of the ultrasonic endoscope 71 is provided.

The ultrasonic endoscope 71 is provided further with an illumination optical system 74 and an observation optical system 75, which serve as optical observation means, on the distal-end part of the ultrasonic probe 20.

Specifically, illumination light of a lamp 76 within the light source device 73 is transmitted by a light guide 77. The illumination light is outputted obliquely or slant forwardly from the distal-end face which is fixedly mounted on the distal-end part 22, further through the illumination optical system 74 which is mounted on an observation window opposed against the distal-end face. The illumination light illuminates the side of a slant forward object.

The illuminated object is image-formed onto a focal-point face by the observation optical system 75 which is mounted on an observation window provided adjacent to the observation window. A distal-end face of an image guide 78 which is formed by a flexible fiber bundle is arranged on the focal-point face. The image guide 78 is inserted into the insertion part 21 and into the operation part 30, and has a distal end thereof which is arranged adjacent to an ocular part 79 mounted at a distal end of the operation part 30, so that an image on the distal-end face is transmitted to a proximate-end face. It is possible to observe the image transmitted to the proximate-end face, through an ocular optical system 79A which is mounted on an ocular window of the ocular part 79.

In connection with the above, in the present embodiment, the injection port 35 is provided on a light guide connector 77a. The other arrangement is similar to that of the first embodiment. The same or identical reference numerals are applied to the same or identical constitutional elements, and the description thereof will be omitted.

According to the embodiment, since there is the optically observing means, in case where observation or therapy is conducted by the ultrasonic wave with respect to parts such as an object internal organ, the affected or diseased part, or the like, it is made easy to set the distal-end part 22 under a state where the ultrasonic wave is outputted to the object part to set the proximal-end part 22 under a state capable of conducting observation and therapy.

Moreover, even in case where insertion is made into the peritoneal cavity, for example, to treat the same, it is not required or unnecessary to provide a bore through which the endoscope for optical observation is inserted, in addition to a bore for therapy due to the ultrasonic wave. Thus, it is possible to reduce pain for a patient.

Furthermore, in the first embodiment, the frequency (hereinafter referred to as "Fa") of the signal which drives the observation ultrasonic transducer is set higher than the frequency of the signal which drives the therapeutic ultrasonic transducer (hereinafter referred to as "Fb"). In the present embodiment, however, the frequency is used in selection from the following combination. That is, Fa is 3.5 MHz, and Fb is 2 !A12 MHz (however, except for 3.5 MHz)

Fa is 4.0 MHz, and Fb is 2 !A12 MHz (however, except for 4.0 MHz)

Fa is 5.0 MHz, and Fb is 2 !A12 MHz (however, except for 5.0 MHz)

Fa is 7.5 MHz, and Fb is 2 !A12 MHz (however, except for 7.5 MHz)

In FIG. 11 and FIG. 12, case of the elastic endoscope 70 is shown which has the forward strabismus optical system with which the distal-end part 22 of the ultrasonic probe 20 shown in the first embodiment is combined. However, it is possible to form the flexible endoscope in combination of the other embodiments.

Figure 14:
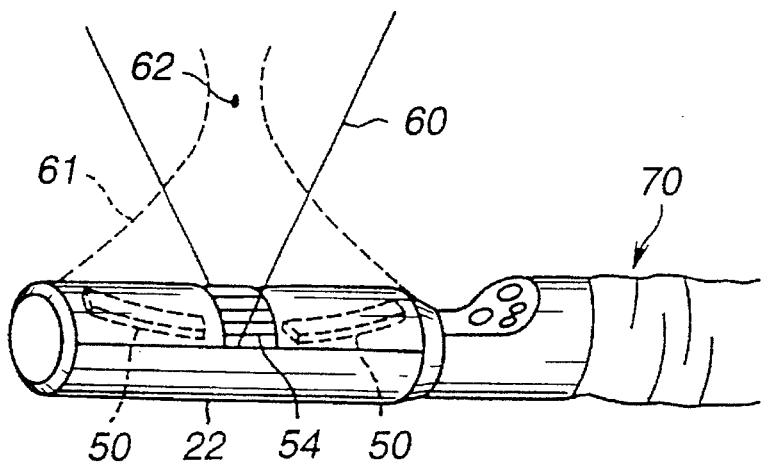
Figure 15:
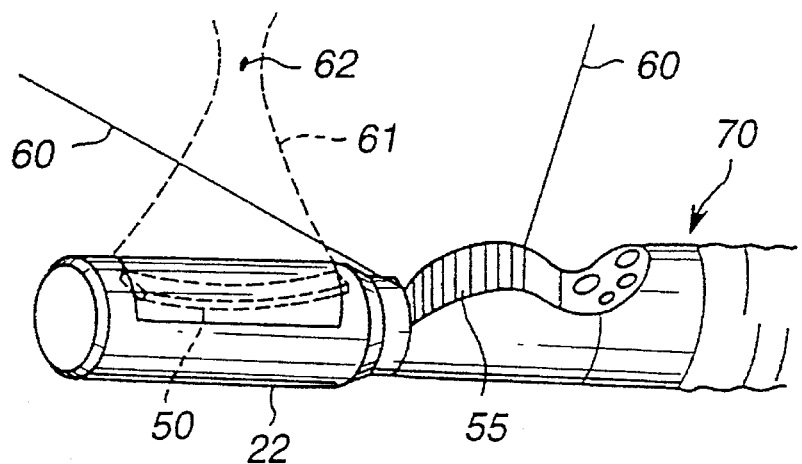
Figure 16:
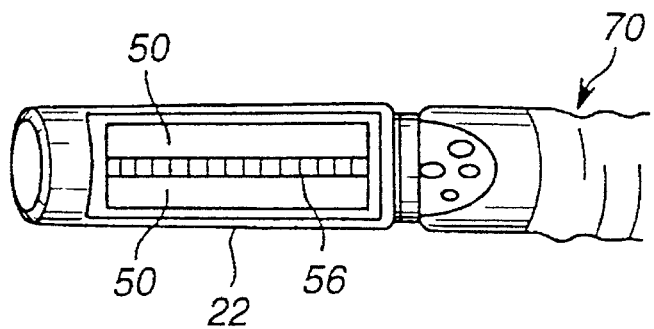

Specifically, combination of the distal-end part of the second, third or fourth embodiment illustrated in FIG. 8, FIG. 9 or FIG. 10, with the distal end of the endoscope 70 is shown in FIG. 14, FIG. 15 and FIG. 16.

According to the ultrasonic diagnosis and therapy system 72 having such arrangement, it is made possible to insert the distal-end part into the upper or lower digestive organ under the guide of the optical image, to conduct the ultrasonic high-temperature therapy of the deep internal organ in the interior of the digestive organ under the guide of the ultrasonic diagnosis image. Accordingly, it is possible to enlarge or magnify application of the ultrasonic diagnosis and therapy system 72 according to the embodiment in a manner of activeness.

A sixth embodiment of the invention will subsequently be described. In the embodiment shown previously, the observation ultrasonic probe, the ultrasonic transducer for acquiring the ultrasonic therapy image due to the convex-type array, the electronic radial array, the linear array or the like and the focusing-type ultrasonic transducer for the ultrasonic therapy have been separated from each other, and these have been used in combination with each other.

As an arrangement which achieves the object of the invention and which can produce functional advantages the same as those of the previous embodiments, it may be an observation & therapeutic ultrasonic transducer in which an ultrasonic transducer for acquiring an ultrasonic diagnosis image and a focusing-type ultrasonic transducer for ultrasonic therapy are integrated with each other.

Figure 17:
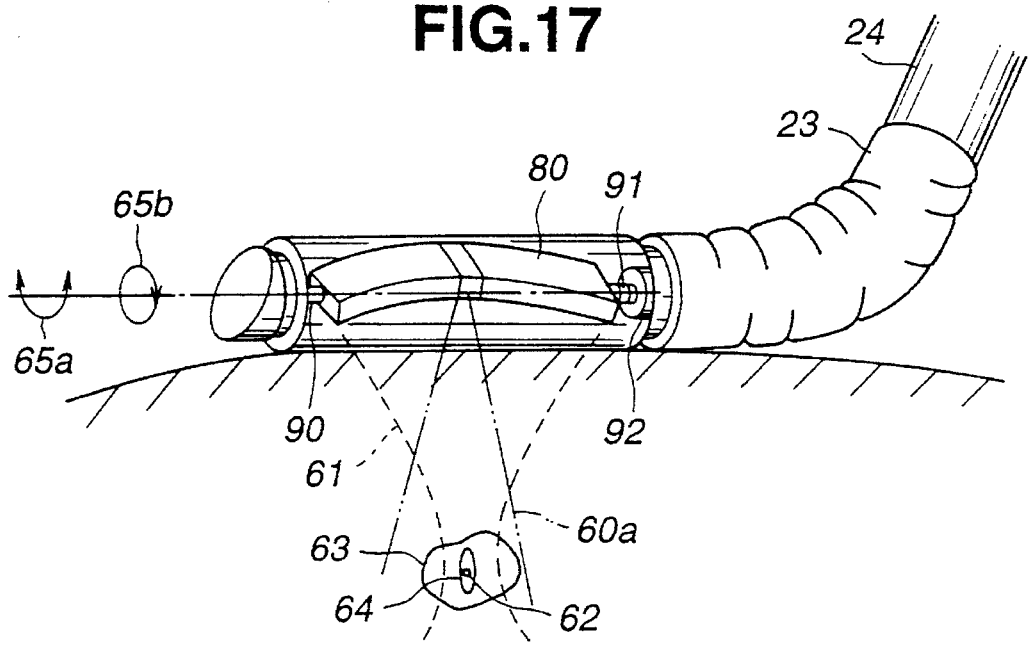

FIG. 17 shows an arrangement of the ultrasonic probe 20 in which an observation & therapeutic ultrasonic transducer 80 is incorporated into the distal-end part 22.

The observation & therapeutic ultrasonic transducer 80 is provided in the distal-end part which is provided with an acoustic window high in acoustic transmittivity. The observation & therapeutic ultrasonic transducer 80 is mounted, by a pin 90, on the distal-end inner wall face of the distal-end part 22 such that an end of the transducer 80 on the distal-end side thereof is made rotatable. The transducer 80 has a proximal-end part thereof which is arranged such that a flexible shaft 91 which is inserted into the ultrasonic probe 20 has a distal end which is mounted on the distal-end part 22 through a bearing 92 having backings which maintain a water-tight state within the distal-end part 22.

Further, the flexible shaft 91 is connected to a motor which serves as rotational drive means (not shown), and is reciprocally rotated (or is rotationally vibrated) in the form of a sector as indicated by the reference numeral 65a in FIG. 17, or is rotationally driven as indicated by the reference numeral 65b, around the pin 90 and an axis of the flexible shaft 91 by rotation of the motor.

Figure 18:
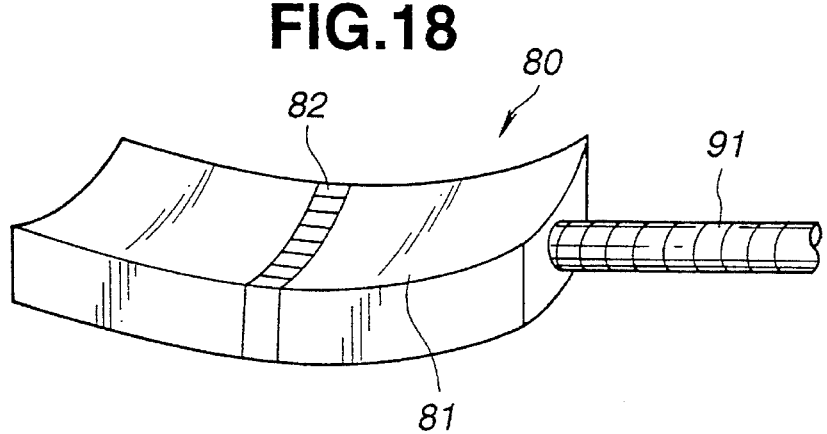

FIG. 18 shows an outer appearance of the observation & therapeutic ultrasonic transducer 80. A therapeutic transducer 81 which is formed into a concave shape is equally divided into two, and an ultrasonic transducer array 82 which is in the form of a belt shape and which forms the observation ultrasonic transducer is integrally provided at a center thereof by junction or the like due to adhesives. An area size of the ultrasonic transducer array 82 is sufficiently smaller than an area size which radiates the therapeutic ultrasonic wave.

The ultrasonic transducer array 82 is formed by a plurality of transducers. A transmission pulse is applied to a plurality of transducers through a phase shifter which shifts the phase (or through a delaying delay element), and the plurality of transducers are successively changed over, whereby the ultrasonic transducer array 82 scans the observation ultrasonic wave in the form of a sector, for example.

In FIG. 17, a sector image which is acquired at a certain rotational position is indicated by the reference numeral 60a. In case of one revolution or once rotation, it is possible also to acquire sector images in the respective directions in the whole periphery.

Figure 19:
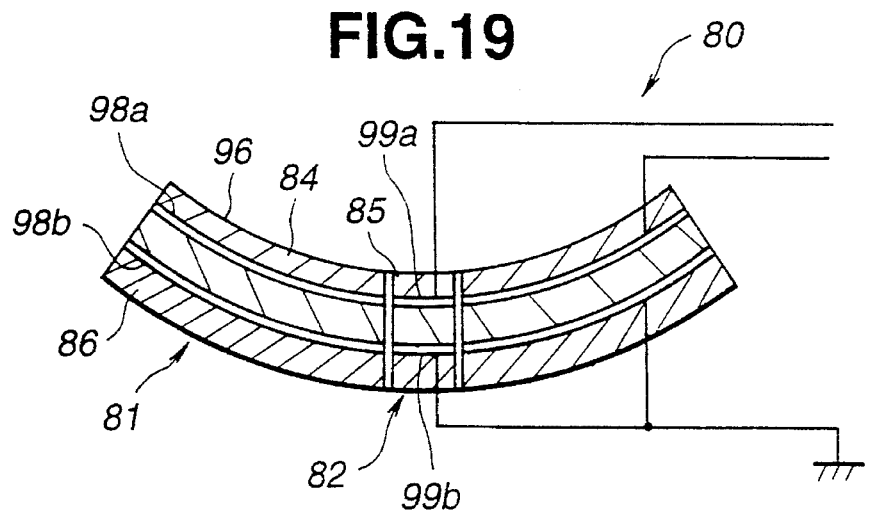

FIG. 19 shows, in a longitudinal cross-section, structure of the ultrasonic transducer or the piezoelectric element which forms the observation & therapeutic ultrasonic transducer 80.

Electrodes 98a and 98b to which the drive signal is applied are fixedly mounted, by evaporation or deposition or the like, respectively on both faces of a piezoelectric element 83a which forms the therapeutic ultrasonic transducer 81. A matching layer 84 which is suitable for radiating a therapeutic ultrasonic wave at high efficiency is provided on the side of a concave face of the piezoelectric element 83a, that is, on the side of a radiating face thereof.

A backing layer 86 is provided on the side of a rear face of the piezoelectric element 83a.

Moreover, electrodes 99a and 99b to which the drive pulse is applied are fixedly mounted, by evaporation or deposition or the like, also on both faces of a piezoelectric element 83b which forms the observation ultrasonic transducer array 82. A matching layer 85 which is suitable for radiating the observation ultrasonic wave at high efficiency is provided on the side of a concave face of the piezoelectric element 83b, that is, on the side of a radiation face thereof. The backing layer 86 is provided on the side of a rear face of the piezoelectric element 83b.

For example, the arrangement is as follows. That is, the electrodes 98b and 99b on the opposite side of the radiation face are connected to a GND, and electrodes 98a and 99a on the side of the radiation face are connected respectively to signal lines to which the drive signal or the transmission pulse is applied.

The sixth embodiment has advantages that (it is possible to conduct scanning of the observation ultrasonic wave and) the focusing point of the therapeutic ultrasonic wave can also be moved under a state that the focusing point of the therapeutic ultrasonic wave is locked to a predetermined position within a scanning range.

Figure 20A:
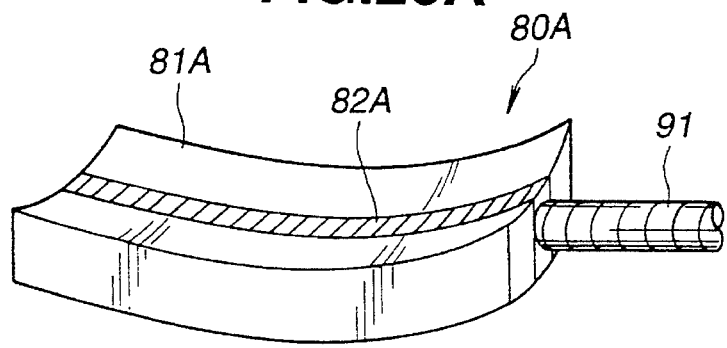
FIG. 20A is a perspective view showing an observation & therapeutic ultrasonic transducer which is different from that shown in FIG. 18.

FIG. 20A shows an observation & therapeutic ultrasonic transducer 80A which is slightly different in arrangement from that in FIG. 18. The transducer 80 in FIG. 18 is equally divided into two with respect to a longitudinal direction, and the observation ultrasonic transducer array 82 is provided at the two equally divided positions. On the contrary, a transducer 80' two-equally divides a therapeutic ultrasonic transducer 81A, in a widthwise direction, which is concave in face and which is in the form of a rectangle, and is provided with an observation ultrasonic transducer array 82A in the form of a belt, along the two equally divided position.

The observation ultrasonic transducer array 82A is of an electric scanning type in which a plurality of transducers are arranged along a curved face, and applies the drive signal to the plurality of transducers by the use of change-over means such as a phase shifter, a multiplexer or the like, to thereby scan the scanning range in the form of a sector, for example, in a plane which includes the transducer array 82A and a shaft 91. Furthermore, setting is made such that the focusing point of the therapeutic ultrasonic wave exists on a center axis within the scanning range, for example. In other words, setting is made such that the focusing point of the therapeutic ultrasonic wave exists on a normal line of the transmitting and receiving plane of the transducer at a center position, in a longitudinal direction, in the plurality of transducers which form the transducer array 82A.

Accordingly, it is possible that the shaft 91 is rotated whereby the scanning face due to the transducer array 82A is rotated to conduct three-dimensional scanning. Further, it is possible to scan both the observation and therapeutic ultrasonic waves under a state in which the focusing point of the therapeutic ultrasonic wave is locked to a predetermined position within the scanning range of the observation ultrasonic wave.

Figure 20B:
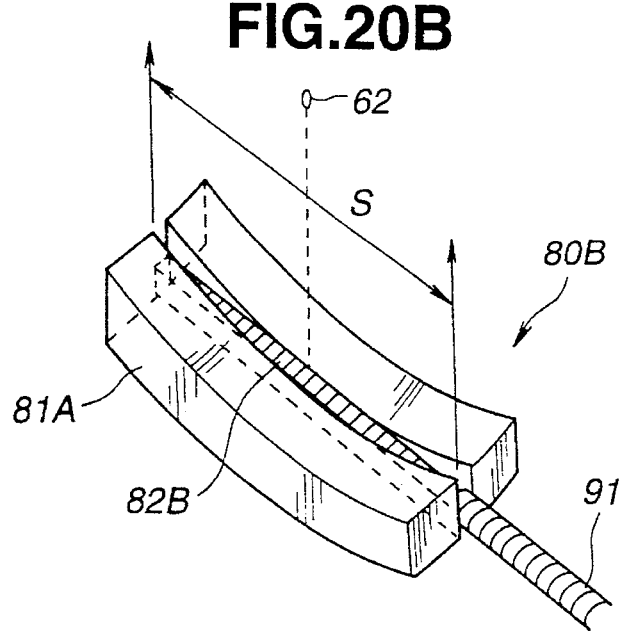
FIG. 20B is a perspective view showing an another observation & therapeutic ultrasonic transducer which is different from that shown in FIG. 18.
Figure 22A:
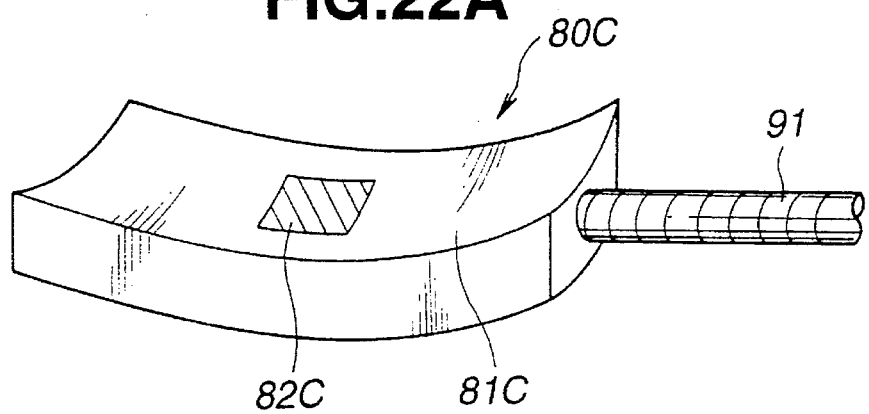

FIG. 20B shows an observation & therapeutic ultrasonic transducer 80B having an arrangement thereof which is slightly different from that shown in FIG. 22A. In the transducer 80A shown in FIG. 22A, the transducer array 82A has been formed along the curved face of the concave. In the transducer 80B shown in FIG. 22B, however, a transducer array 82B is arranged in the form of a belt along a plane thereof.

The plane is in parallel to an axial direction of the shaft 91.

Moreover, the observation ultrasonic transducer array 82B is of an electronic linear scanning type in which a plurality of transducers are arranged along the plane. Change-over means such as a multiplexer or the like is used to successively apply the drive signal to the transducer, whereby it is possible to scan a scanning range S which is shown diagrammatically in FIG. 20B.

Setting is made such that the focusing point 62 of the therapeutic ultrasonic wave exists on a center line of the scanning range S, for example. In other words, setting is made such that the focusing point of the therapeutic ultrasonic wave exists on a normal line of the transmitting and receiving face of the transducer at the center position in the longitudinal direction, in the plurality of transducers which form the transducer array 82B.

In the present embodiment, the change-over means such as a multiplexer or the like is used whereby it is possible to easily form scanning means or a scanning mechanism which conducts electronic linear scanning. Moreover, the flexible shaft 91 is rotated whereby it is possible to rotate the linear scanning face to conduct three-dimensional scanning. Furthermore, it is possible to scan both the observation and therapeutic ultrasonic waves under a state in which the focusing point 62 of the therapeutic ultrasonic wave is locked at a predetermined position within the scanning range S of the observation ultrasonic wave.

In connection with the above, also in case of the transducer 80 in FIG. 18, the arrangement may be such that the transducer array 82 is formed along the plane, and the electronic linear scanning is conducted by the transducer array 82.

Figure 21:
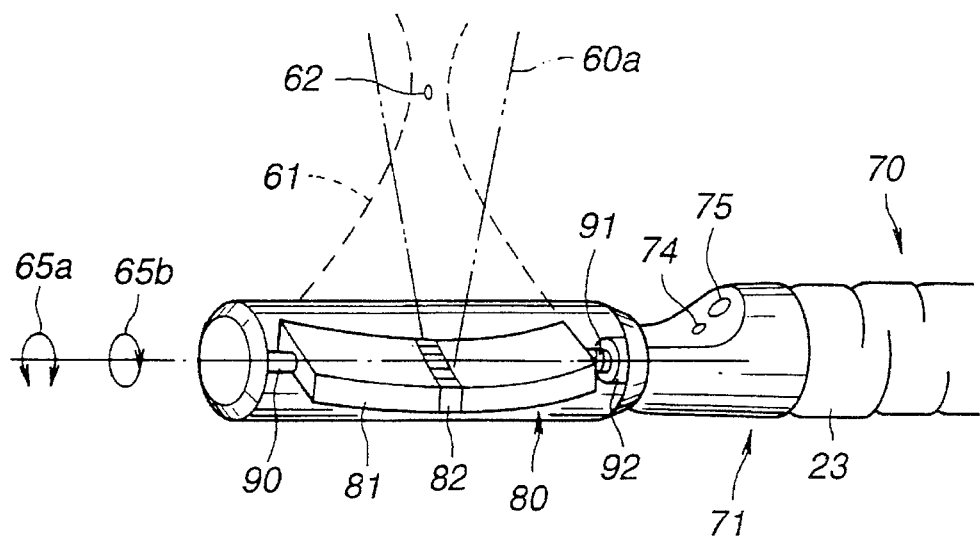

Further, FIG. 21 shows structure of the ultrasonic endoscope 71 into which the observation & therapeutic ultrasonic transducer is incorporated at the distal-end part 22 of the elastic endoscope 70.

The ultrasonic endoscope 71 is driven similarly to case of FIG. 17.

In this case, it is possible to simultaneously conduct also optical observation. The others have function and operation or manipulation similar to those shown in FIG. 17, and have similar advantages (merits).

In the sixth embodiment described above, the observation ultrasonic transducer has been described as being formed by the transducer array to conduct the electronic scanning. However, the observation ultrasonic transducer may be one which conducts mechanical scanning to be described later and which forms the observation ultrasonic transducer. However, this modification has no function in which the focusing point of the therapeutic ultrasonic wave is locked to the predetermined position within the scanning range of the observation ultrasonic wave.

FIG. 22A shows an outer appearance of an observation & therapeutic ultrasonic transducer 80C according to a modification of the sixth embodiment.

A transducer radiation plane 81C which is formed into a concave shape radiates the therapeutic ultrasonic wave and the observation ultrasonic wave.

In the radiation face 81C, a square (or circular) region of a small size indicated by the reference numeral 82C at a center part, for example, is an observation ultrasonic radiation region which radiates the observation ultrasonic wave, and a wide range other than this range in the transducer radiation face 81C is a therapeutic ultrasonic radiation region which radiates the therapeutic ultrasonic wave.

Figure 22B:
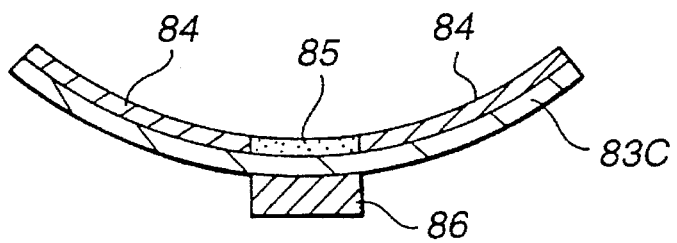
FIG. 22B is a cross-sectional view of FIG. 22A.

FIG. 22B shows structure of the ultrasonic transducer or the piezoelectric element which forms the observation & therapeutic ultrasonic transducer 80C. The matching layer 85 and the backing layer 86 are so provided on a region of a center part of a concave-type piezoelectric element 83C that the region becomes a state suitable for radiating the observation ultrasonic wave. Further, regions other than the central region is provided with the matching layer 84 suitable for radiating the therapeutic ultrasonic wave at high efficiency.

Figure 22C:
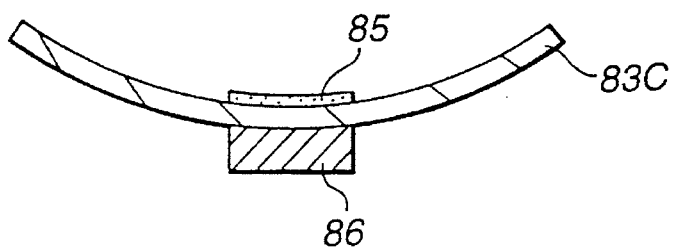
FIG. 22C is a cross-sectional view showing an arrangement example which is different from that shown in FIG. 22B.

Structure may be made to structure shown in FIG. 22C in place of structure shown in FIG. 22B. In FIG. 22C, structure is adopted in which the matching layer 85 and the backing layer 86 are provided only on a region at a center part at which the observation ultrasonic wave is radiated, of a concave-type piezoelectric element 83C.

Figure 22D:
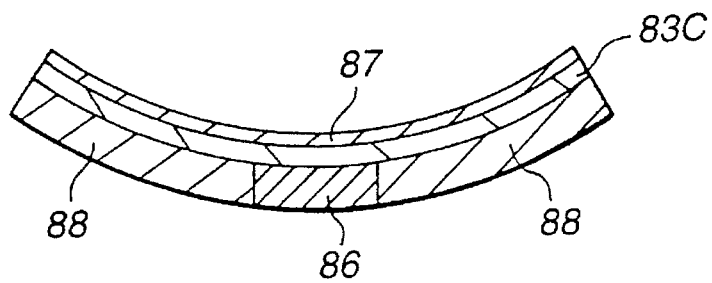
FIG. 22D is a cross-sectional view showing an another arrangement example which is different from that shown in FIG. 22B.

Moreover, the structure may be made to an arrangement in which a matching layer 87 which is suitable for radiating the observation and therapeutic ultrasonic wave to the whole face of the radiation face of the concave-type piezoelectric element 83C as shown in FIG. 22D is provided in place of that in FIG. 22B or FIG. 22C, a backing layer 86 which is suitable for radiating the observation ultrasonic wave is provided in a region at a center of a rear face of the piezoelectric element 83C, and a backing 88 which is suitable for radiating the therapeutic ultrasonic wave is provided in a region other than the aforesaid region.

Figure 23A:
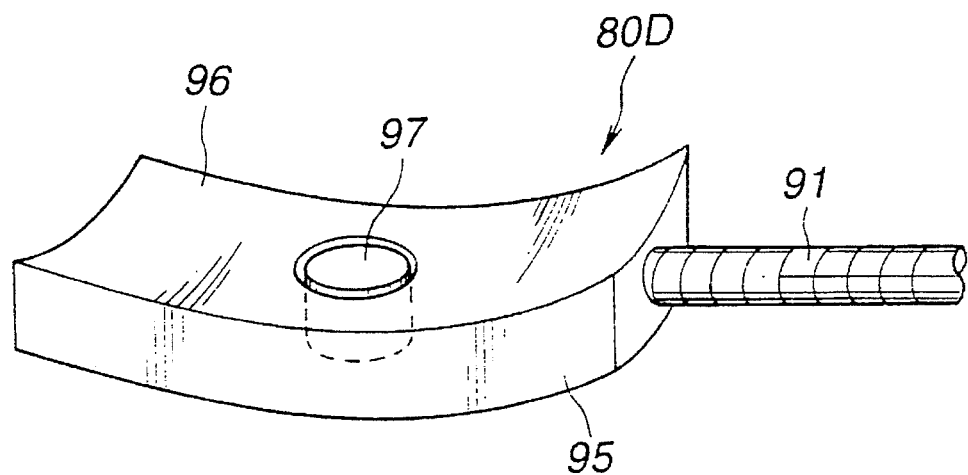
FIG. 23A is a view showing an another arrangement example which is different from that shown in FIG. 22A.

Furthermore, the structure may be an arrangement in which an observation ultrasonic transducer 97 is incorporated into a center part of a radiation face 96 of a therapeutic ultrasonic transducer 95 like an observation & therapeutic ultrasonic transducer 80D shown in FIG. 23A.

Figure 23B:
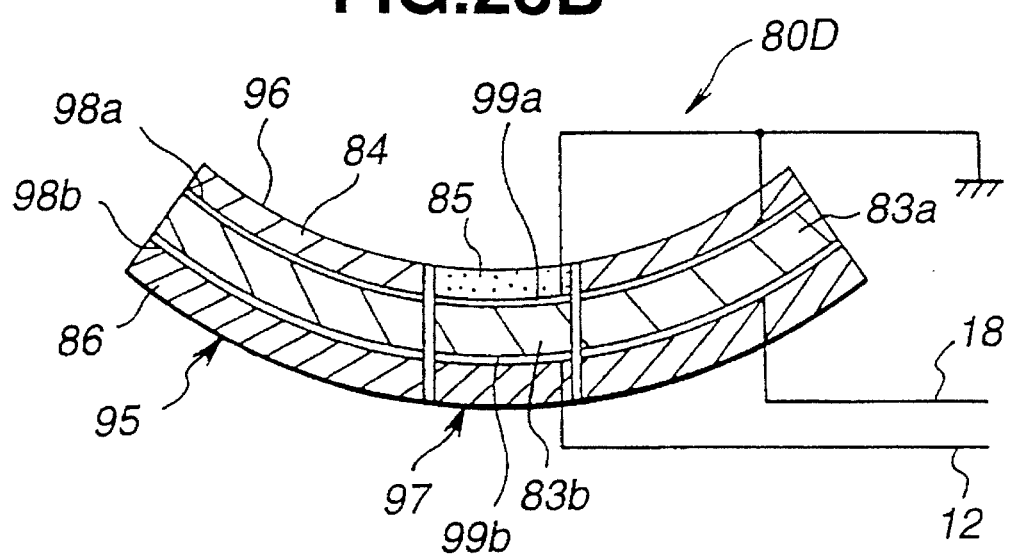

Cross-sectional structure of FIG. 23A is shown in FIG. 23B. A disk-shaped observation ultrasonic transducer 97 is inserted into a circular bore which is provided at a center part of the concave-type therapeutic ultrasonic transducer 95, so as to be fitted thereto and whose outer diameter is an inner diameter of the bore, and is fixedly mounted thereon by adhesives or the like.

The electrodes 98a and 98b to which a drive signal is applied are fixedly mounted, by evaporation or deposition or the like, respectively on both faces of a piezoelectric element 83a which forms the therapeutic ultrasonic transducer 95. The alignment or matching layer 84 which is suitable for radiating, at high efficiency, the therapeutic ultrasonic wave is provided on the concave side, that is, the side of a radiation face of the piezoelectric element 83a. The backing layer 86 is provided on the side of a rear face of the piezoelectric element 83b.

Further, the electrodes 99a and 99b to which a drive pulse is applied are fixedly mounted, by evaporation or deposition or the like, respectively on both faces of the piezoelectric element 83b which forms the observation ultrasonic transducer 97. The alignment or matching layer 85 which is suitable for radiating, at high efficiency, the observation ultrasonic wave is provided on the concave side, that is, the side of a radiation face of the piezoelectric element 83b. The backing layer 86 is provided on the side of a rear face of the piezoelectric element 83b.

The arrangement is such that, for example, the electrodes 98a and 99a on the side of the radiation face are connected to a GND, while the face are 98b and 99b on the side of the rear face are connected respectively to signal lines 18 and 12 to which the drive signal or the transmission pulse is applied.

The observation & therapeutic ultrasonic transducer may be one in which the observation ultrasonic transducer 97 is incorporated into a center part of a rear face of the therapeutic ultrasonic transducer 95, or may be combination in which the observation ultrasonic vibrator 97 is mounted on the center part of the rear face of the therapeutic ultrasonic transducer 95, or the like.

Operation of the modification will subsequently be described. The observation & therapeutic ultrasonic transducer 80C (or 80D) is reciprocally rotated as indicated by the reference numeral 65a in FIG. 17 or FIG. 21 to conduct mechanical sector scanning, or is rotated as indicated by the reference numeral 65b to conduct mechanical radial scanning, and the observation ultrasonic wave is radiated to acquire an ultrasonic diagnostic sector image or an ultrasonic diagnostic radial image which becomes the ultrasonic diagnostic image.

At this time, the matching layer 85 or the like and the packing layer 86 which are provided at the center portion of the piezoelectric element 83a of the observation & therapeutic ultrasonic transducer 80C intermittently radiates the ultrasonic pulse of a wide band. Reflected reflecting ultrasonic wave is received, which is utilized as generation of the ultrasonic diagnosis image.

Depiction of a lesion part is conducted by the ultrasonic diagnosis image, the focus-point marker which is displayed on the diagnostic image is according to the lesion part, or the like, to conduct positioning setting. Thereafter, the observation & therapy ultrasonic transducer 80C is set such that a focal point thereof is directed to a set position (angle), and the reciprocal rotation or the rotation of the transducer 80C stops.

Thereafter, portions other than an observation function part at the center-part region of the observation & therapeutic ultrasonic transducer 80C is driven by a continuous wave or by an intermittent wave, to radiate the therapeutic ultrasonic wave. At this time, the periphery of the piezoelectric-element center part of the observation & therapeutic ultrasonic transducer 80C is made to an arrangement which is suitable for radiating the ultrasonic wave of a narrow band, as described previously. Accordingly, the ultrasonic wave having high efficiency and high strength is radiated.

After the therapeutic focusing ultrasonic wave has been irradiated to the lesion part, scanning is conducted, and the ultrasonic observation is again conducted, to confirm the degree or extent of high-temperature cauterization on the ultrasonic diagnosis image.

According to the present modification, since the observation & therapeutic ultrasonic transducer 80C is used which uses both an observation one and a therapeutic one, it is possible to incorporate the transducer into the distal-end part easily more than case where separate transducers are incorporated.

Subsequently, a seventh embodiment of the invention will be described.

Figure 24:
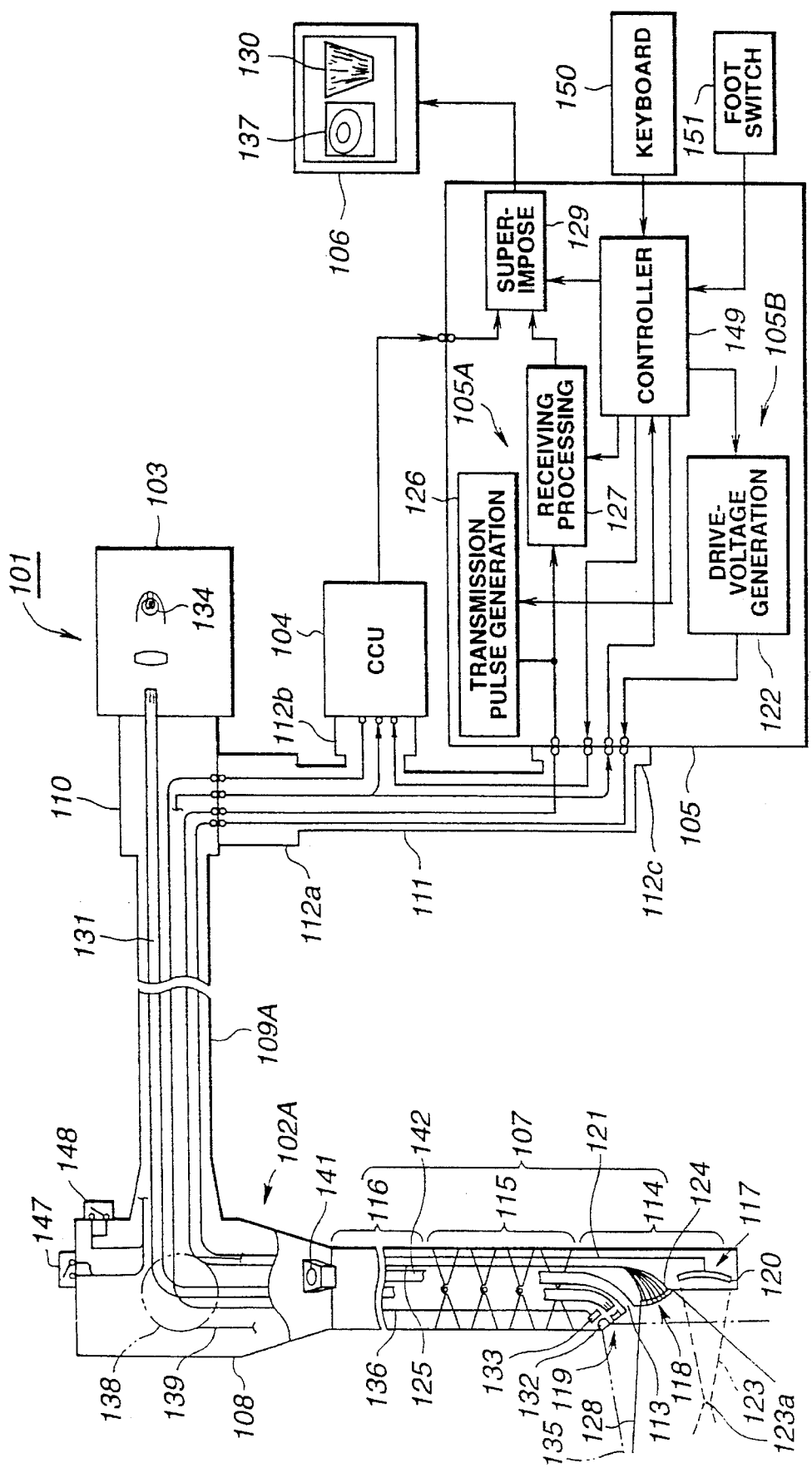

As shown in FIG. 24, the seventh embodiment of the ultrasonic diagnosis and treatment system 101, for example, comprises a ultrasonic probe 102A having an electronic-endoscope-like structure, a light source device 103 for providing illumination to light transmission means of the ultrasonic probe 102A, a camera controlunit (referred to as CCU, hereinafter) 104 for signalprocessing for image pickup means built in the ultrasonic probe 102A, an ultrasonic diagnosis and treatment apparatus 105 housing a signal processing system 105A for producing ultrasonogram and a treatment signal generator system 105B for producing treatment driving signal, and a color monitor 106 for presenting both an endoscopic image and an ultrasonogram based on the video signal from CCU 104 and the video signal derived from the ultrasonic signal processing system.

The ultrasonic probe 102A is constructed of a small tube (capillary) insert portion 107, a wide operation portion 108 which is formed on the proximal of the insert portion 107 and which is gripped by an operator for insertion and bending operations, and a universal cable 109A extended from the operation portion 108, wherein the light source connector 110 at one end of the universal cable 109A is detachably connected to the light source device 103.

Connected to the light source connector 110 is a signal connector 112a at one end of a signal cable 111. The other ends of the signal cable 111 have a CCU connector 112b to be connected to the CCU 104 and an ultrasonic connector 112c to be connected to the ultrasonic diagnosis and treatment apparatus 105.

Figure 27:
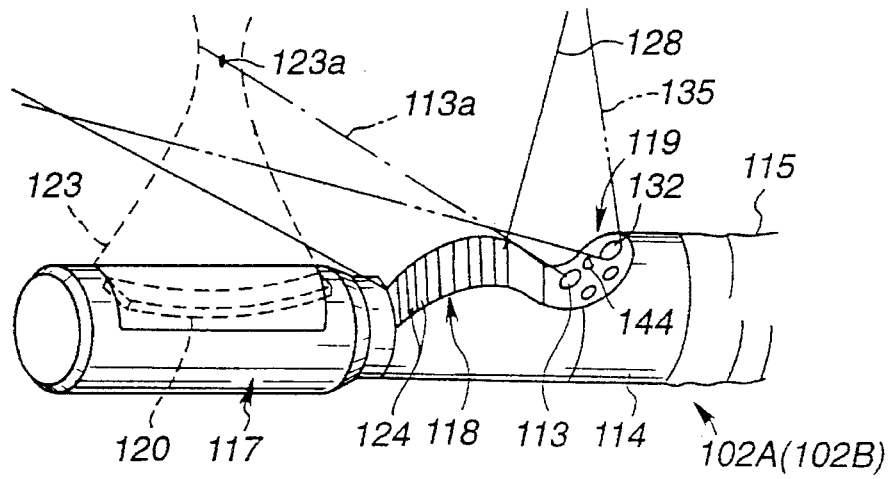

The insert portion 107 is constructed of a rigid distal-end portion(or end portion) 114, a bendable portion 115, and a flexible portion along the axis of the insert portion 107 way back from its end. As shown in FIG. 27, the end portion 114 is constructed of ultrasonic treatment means 117, ultrasonic monitoring means 118, an forceps outlet port 113 as a treatment function guide portion, and optical monitoring means 119 along the axis of the insert portion 107 way back from its end.

The ultrasonic treatment means 117 is made of a ultrasonic treatment transducer 120 having a concave face. By applying a driving signal to the transducer 120 from a driving voltage generator 122 in the ultrasonic diagnosis and treatment apparatus 105, via a signal line 121 that is routed through the insert portion 107, the ultrasonic wave emitted from the concave face of the therapeutic ultrasonic transducer travels keeping its wave front concave, converges in a beam coverage 123 shown by the dotted line in FIG. 24, and still travels as a directional therapeutic ultrasonic beam that focuses at a focus 123a.

The ultrasonic beam is very intensive at the focus 123a, and thus gives a high acoustic energy density. When with a lesion such as tumor set in the vicinity of the focus 123a, a large amplitude driving signal is applied to the concave therapeutic ultrasonic transducer 120, a high acoustic energy derived from generated ultrasonic wave burns the lesion for cauterization treatment.

The ultrasonic monitoring means 118 is made of a convex-array ultrasonic transducer 124, which is connected via a signal line 125 to a transmission pulse generator circuit 126 and a receiver signal processing circuit 127, both of which form a signal processing system 105A.

A transmission pulse from the transmission pulse generator circuit 126 is sequentially applied to each transducer element of the convex-array ultrasonic transducer 124, which scans sequentially a radially extending ultrasonic monitoring coverage 128 in a plane in which the axis of the insert portion 107 lies, in order to irradiate a target lesion. The ultrasonic wave reflected back from the lesion is then received by each transducer element of the convex-array ultrasonic transducer 124 that is already used for transmission, and there converted into an electrical signal. The electrical signal is subjected to the receiver signal processing circuit 127 for signal processing, including amplifying, then converted via DSC into a standard video signal corresponding to ultrasonogram, and fed to a color monitor 106 via a superimposing circuit 129 so that ultrasonogram 130 as an ultrasonic image is presented thereon.

The driving frequency of the transmission pulse from the transmission pulse generator circuit 126 is set such that it does not agree with the frequency (or frequency band) of the driving signal from the driving voltage generator circuit 122.

Ultrasonogram image is not interfered with by any noise due to treatment ultrasonic wave even if the treatment ultrasonic wave is emitted while ultrasonogram monitoring is made using the ultrasonic monitoring means 118. In this case, a filter such as a trap circuit for filtering out noise may be included in the receiver signal processing circuit 127. A filter such as a trap circuit may be included to the driving voltage generator circuit 122 to filter out the driving frequency component from the ultrasonic monitoring means 118.

As shown in FIG. 24, the optical monitoring means 120 is constructed of illumination light projection means (or simply illumination light system) for projecting illumination light through a light guide 131, a lens and an illumination window, and image pickup means having an objective lens 132 for picking up an image of the tissue of interest lighted by the illumination, and CCD 133 disposed in a plane of the focus of the objective lens 132.

The light guide 131 is routed through the insert portion 107, and its light source connector 110 is connected to the light source 103. The light guide 131 transmits illumination light, generated by a lamp 134 and converged by the lens, and projects in a slantly forward direction the illumination light through the end face of the end portion 114 and the lens of the illumination window.

The coverage of the illumination light looking in a slantly forward direction almost agrees with the viewing coverage 135 of the objective lens 132.

The optical monitoring means 120 is thus constructed of slantly forward looking illumination and monitoring means. The objective lens 132 allows an optical image of the tissue of interest to take place on the pickup surface of CCD 133. The CCD 133 is connected to an unshown video signal processing system in CCU 104 via a signal line 136. The signal from CCD 133 is converted by the video signal processing system into a video signal, which is then fed via the superimposing circuit 129 to the color monitor 6 where both ultrasonogram 130 and endoscopic image 137 are simultaneously displayed.

The bendable portion 115 connected to the end portion 114 is constructed a number of segments which are mutually connected in a flexible manner to allow a bending. Angle wires 129 are connected at their one ends to the end portion 114, and connected at the other ends to a pulley 38 in the operation portion 108. Rotation of an angle knob 140 (FIG. 25) turns the pulley 138 which in turn pulls one of the angle wires 129 and loosens the other of the angle wires 129 so that a bend is formed in a manner that the bendable portion 115 is bent inwardly on the pulled wire 129 side.

The manipulation of the angle knob 140 allows bending in four directions, up and down, right and left, or two directions up and down, or right and left.

The bendable portion 115 is freely bent, causing the ultrasonic treatment means 117, the ultrasonic monitoring means 118, the treatment function guide portion, and the optical monitoring means 119 all in front of the bendable portion 115 to look in any direction, and the construction of the bendable portion 115 has a construction similar to the bendable portion of the ordinary endoscope.

The operation portion 108 has on its distal portion an inlet port 141 through which an instrument such as forceps is introduced. The inlet port 141 communicates with an instrument channel 142 disposed in the insert portion 107.

As shown in FIG. 27, the instrument channel 142 communicates with the treatment function guide disposed in the end portion 114, that is, the forceps outlet port 113 which functions as a guide for treatment using an instrument.

The forceps outlet port 113 is disposed in the vicinity of the optical monitoring means 119. When an unshown instrument is projected out of the forceps outlet port 113 for treatment of an organ, the optical monitoring means 119 closely observes the projected instrument and the state of the treatment.

As shown in FIG. 27, a nozzle 144 is disposed facing an observation window in order to clean and dry the outer surface of the observation window. The nozzle 144 communicates with air and water pipings (not shown) routed through the insert portion 107, and their other ends are connected to a fluid control system in the light source device 103. By manipulating air feeding and water feeding buttons 145 (see FIG. 25) on the operation portion 108, air feeding or water feeding is activated. When the outer surface of the observation window is stained, it is cleaned by feeding water.

A subsequent air feeding dries or eliminates water drops from the outer surface of the observation window. Thus, the observation window is kept clean to maintain clear viewing therethrough.

A suction button 146 is provided nest to the air and water buttons 145, and the suction button 146 is manipulated to suck up unwanted humor via the forceps outlet port 113 on the end of instrument channel 142, and to drain the unwanted humor into a disposal container. On its proximal portion, the instrument channel 142 communicates with an unshown suction channel which is connected to a suction pump in the fluid control system. The instrument channel 142 partly functions as a suction channel for sucking up a fluid, and in this case, a suction port is the forceps outlet port 113.

Disposed on the proximal portion of the operation portion 108 are video control boutons (or video control switches) 147, 148 for freezing the endoscopic image or switching the display, and the signals from video control buttons 147, 148 are sent to CCU 104 and a controller 149.

The controller 149 is connected to a keyboard 150 and a foot switch 151. Through the keyboard 150, treatment time may be set for the ultrasonic treatment means 117 or clinical recording of a patient may be input. By manipulating the foot switch 151, the ultrasonic treatment means 117 is activated for treatment and then deactivated.

The controller 149 is also connected to the driving voltage generator 122, the transmission pulse generator circuit 126, the receiver processing circuit 127, and the superimposing circuit 129 all in the ultrasonic diagnosis and treatment apparatus 105. By entering inputs through the keyboard 150, the controller 149 sets parameter settings such as an intensity (or amplitude) of the driving voltage to the driving voltage generator 122 for the ultrasonic treatment means 117 to provide high-power ultrasonic output, modifies ultrasonic transmission settings for ultrasonogram, modifies signal processing settings for received signal, and controls images displayed on the color monitor 106.

The controller 149 is also connected to CCU 104, and thus the keyboard 150 controls CCU 104, for example, to set CCU4 to a mode for a still picture presentation. In FIG. 24, the ultrasonic diagnosis and treatment apparatus 105 comprises the signal processing system 105A for providing ultrasonogram and the treatment signal generator system 105B for producing the treatment signal. Alternatively, however, the signal processing system 105A and the treatment signal generator system 105B may be separately housed. Furthermore, two monitors may be included in the system, one for the endoscopic image presentation and the other for the ultrasonogram presentation.

Figure 25:
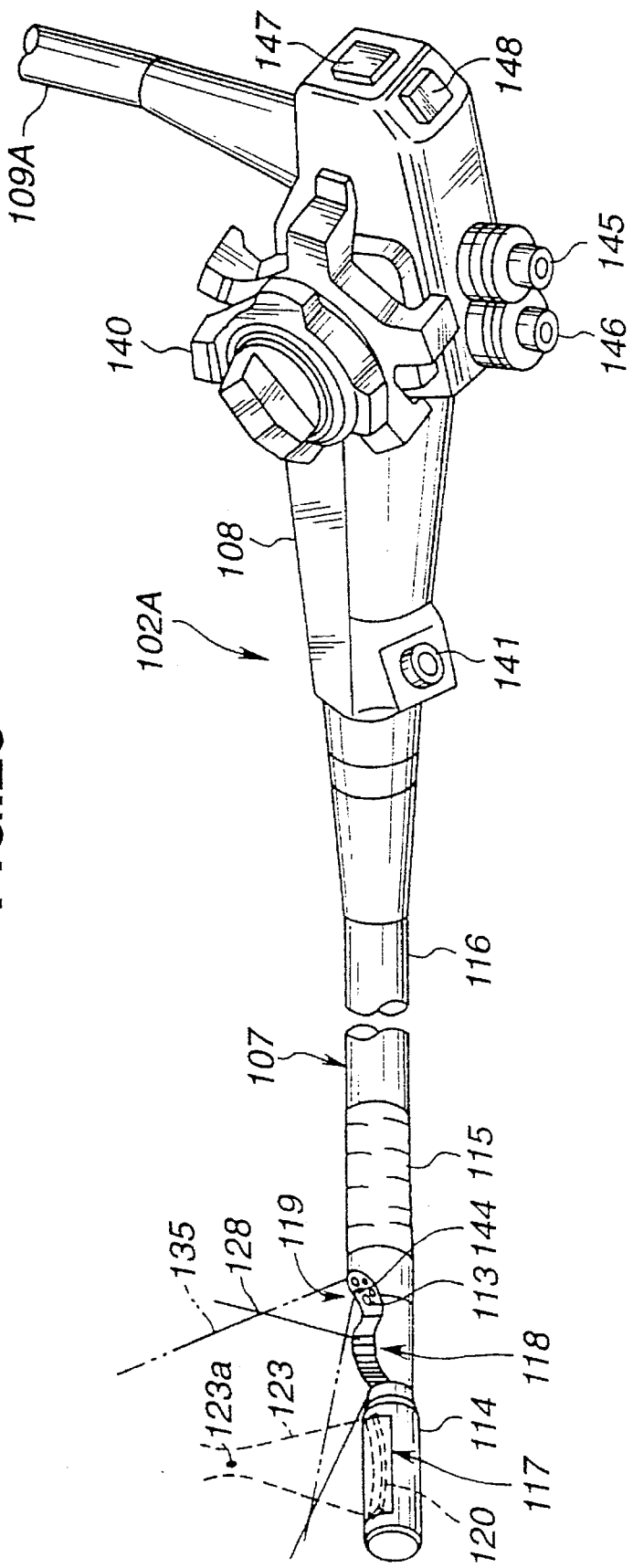

FIG. 25 shows the outline of the ultrasonic probe 102A. The ultrasonic probe 102A employs the configuration of an electronic endoscope in which image pickup means is used as the optical monitoring means 119. Although in the ultrasonic probe in FIG. 24, the configuration of the electronic endoscope is used as the optical monitoring means 119, alternatively, an ultrasonic probe 102B having the configuration of a fiberscope may be used as the optical monitoring means 119.

Figure 26:
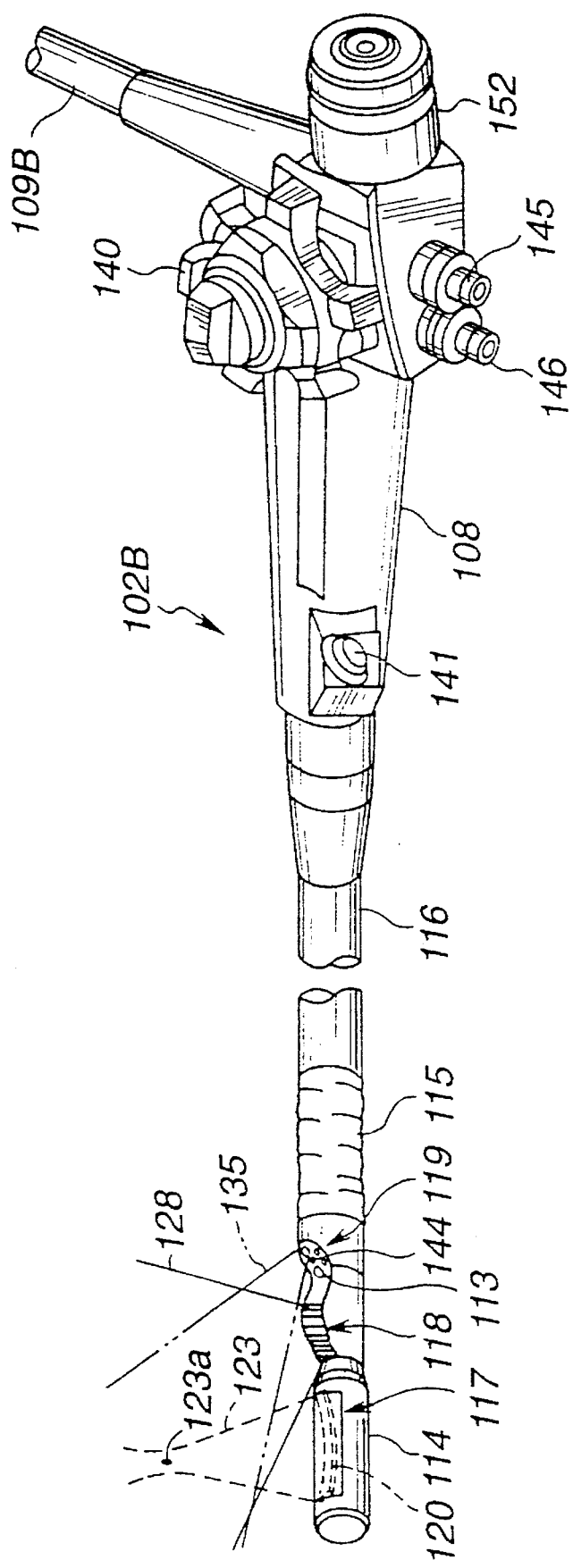

As shown in FIG. 26, the ultrasonic probe 102B is dispensed with the video control buttons 147, 148 on the proximal end of the operation portion 108 in the ultrasonic probe 102A in FIG. 25, and instead, the ultrasonic probe 102B is provided with an eye-piece portion 152. In FIG. 1, instead of CCD 133, an image guide that transmits an optical image is disposed, and the image guide transmits the optical image obtained by the objective lens 132 to the end face of the eye-piece portion 152, and an enlarged optical image is observed through the viewing window on the proximal end of the eye-piece portion 152.

A universal cable 109B having no signal line 136 is extended from the operation portion 108. The rest of the construction of the ultrasonic probe remains unchange from FIG. 25. Reference numerals equivalent to those described with reference to FIG. 25 are designated with the same reference numerals, and their description is omitted. As an ultrasonic probe, an unshown TV camera is mounted on the eye-piece portion 152 of the ultrasonic probe 102B. If, in this case, the signal connector at the signal cable of the TV camera is connected CCU 104 in FIG. 24, an ultrasonic diagnosis and treatment system having almost the same functions described with respect to FIG. 24 is provided.

The alternate embodiment of the ultrasonic diagnosis and treatment system constructed of the ultrasonic probe 102B in FIG. 26 is equivalent to the system without CCU 104 in FIG. 24. In this case, the color monitor 106 presents the ultrasonogram 130 only (namely, the superimposing circuit 129 outputs its video input from the receiver processing circuit 27 as it is without any processing, or the superimposing circuit 129 may be dispensed with).

FIG. 27 is an enlarged view showing the ultrasonic probe 102A or 102B shown in FIG. 25 or FIG. 26.

As shown in FIG. 27, the ultrasonic treatment means 117 is constructed of an concave ultrasonic treatment transducer 120 having a rectangular transducer element which is inwardly curved along its longitudinal direction. Coverage overlapping takes place by three coverage: the beam coverage 123 of the treatment ultrasonic beam emitted by the ultrasonic treatment transducer 120 in the transverse direction (upward direction in FIG. 27) approximately perpendicular to the transducer longitudinal direction, the sectorial ultrasonic monitoring coverage (simply monitoring coverage) 128 looking slantly forwardly, resulted in by, for example, the convex-array ultrasonic transducer 124 as the ultrasonic monitoring means 118, and the conical monitoring coverage 135 by the optical monitoring means 119.

More specifically, as shown in FIG. 27, the optical monitoring means 119 is set up so that the focus 123a is kept within its monitoring coverage 135, and the ultrasonic monitoring means 118 is also set up so that the focus 123a is kept within its ultrasonic monitoring coverage 128. For example, the ultrasonic monitoring coverage 128 is sectorially wide between an angle transverse to the probe axis and an angle slanted forwardly in FIG. 27, and the sector center of the ultrasonic monitoring coverage 128 is slanted forwardly.

Since the optical monitoring coverage and the acoustic monitoring coverage overlap with the focus 123a kept within them, with a lesion set in the vicinity of the focus 123a, the ultrasonogram 130 and the endoscopic image 137 show the state with the lesion in presence (In the endoscopic image 137, however, a lesion cannot be visibly recognized if the lesion exists under a top surface. In this case, the lesion can be recognized in the ultrasonogram 130.)

The above arrangement offers the advantage that positioning the end of an instrument exactly on a lesion is easily performed, and this advantage is particularly useful in such a situation that a lesion needs to be partly removed for biopsy using an instrument before cauterizing the lesion with the ultrasonic treatment means 117 and that biopsy is performed to assure that a lesion has been cauterized sufficiently enough after the lesion has been treated by the ultrasonic treatment means 117.

The ultrasonic treatment transducer 120 constituting the ultrasonic treatment means 117 is used to emit a high-powered, converged beam (namely, focussed ultrasonic beam) for treatment, and may be a single ultrasonic transducer or a plurality of ultrasonic transducers.

The ultrasonic transducer 120 is not limited to a longitudinally concave one, the ultrasonic transducer 120 may be constructed of a single or a plurality of longitudinally concave transducers or transversely concave transducers. If planar transducers are employed, they may be constructed in a phase-array arrangement so that phase is shifted to focus the ultrasonic beam.

A concave lens may be attached to the ultrasonic output face of a planar ultrasonic transducer so that the beam is emitted to be focussed. The construction of the transducer has no particular limitation in its design as long as the transducer has a construction suited for emission to focus the ultrasonic beam and an associated driving means.

The construction of the end portion 114 is not limited to the one show in FIG. 27, it may be constructed as shown in FIG. 28A through FIG. 30.

In FIG. 27, the ultrasonic monitoring means 118 provides the sectorial ultrasonic monitoring coverage 128 ranges from an angle transversely extending to an angle slanted forward. In a first alternate example of the end portion 114A shown in FIG. 28A, the center axis of the monitoring coverage 135, namely, monitoring center axis (or optical axis) of the optical monitoring means 119 is designed to intersect the focus 123a, and the center axis 128a of the ultrasonic monitoring coverage 128 of the ultrasonic monitoring means 118 is designed to intersect the focus 123a.

Figure 28A:
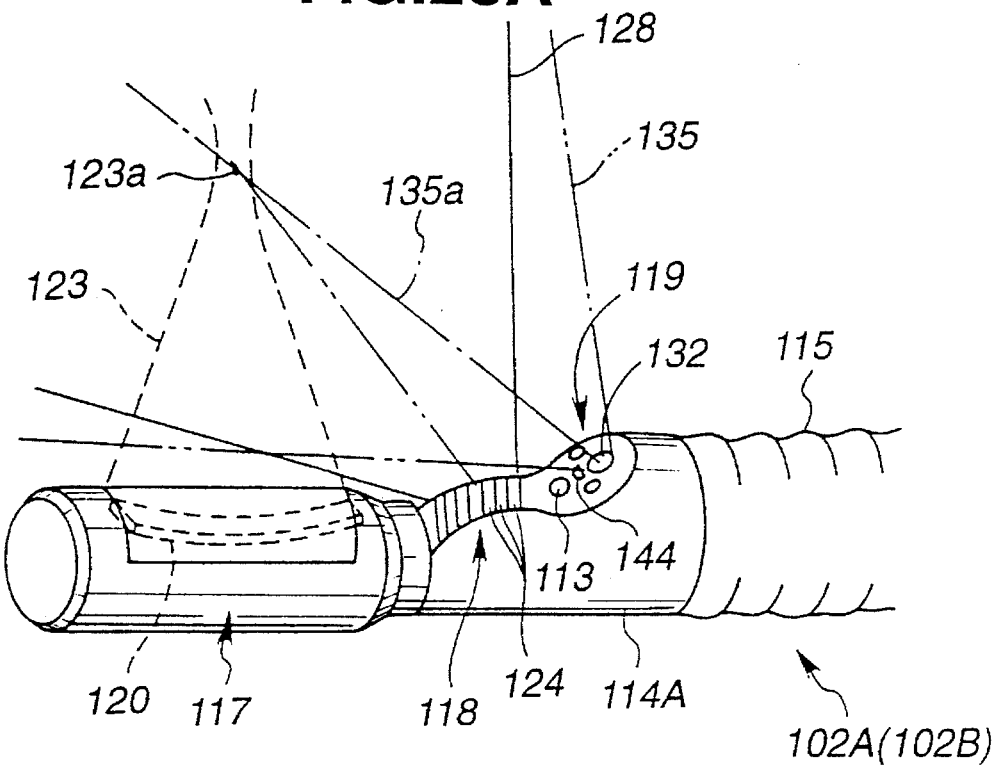
FIG. 28A is a view showing a distal-end side of an ultrasonic probe according to a first modification.
Figure 28B:
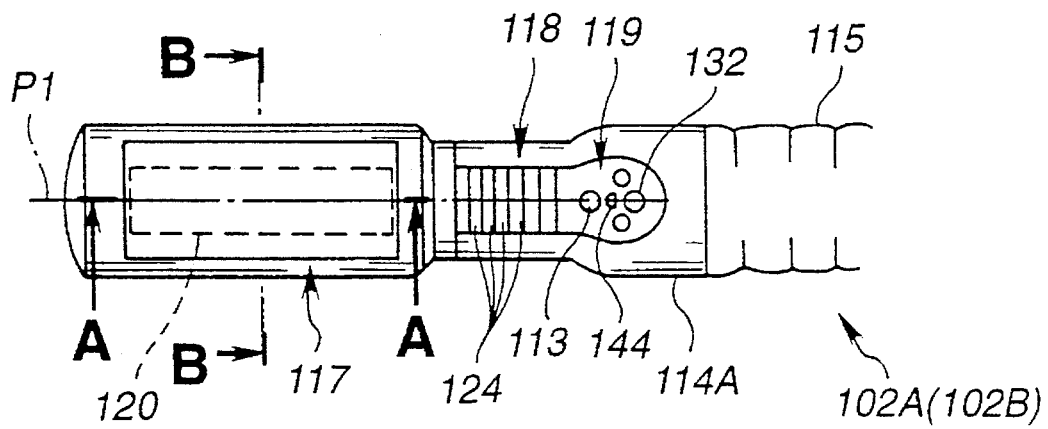
FIG. 28B is a top plan view of FIG. 28A.

As shown in FIG. 28B, the concave faced ultrasonic transducer 120, the convex-array ultrasonic transducer 124, and the objective lens 132 are arranged on the end portion 114 so that the center cross-section line P1 that longitudinally extends along the ultrasonic treatment transducer 120 made of a concave faced rectangular ultrasonic transducer board runs through the center of the convex-array ultrasonic transducer 124 and further runs through the center line (optical axis).

In FIG. 28B, the illumination windows are symmetrically arranged on both sides of the objective lens 132 (in FIG. 27, the two illumination windows are arranged on one side of the objective lens 132, but even in FIG. 27, the two illumination windows may be arranged on both sides of the objective lens 132 as in FIG. 28B). In FIG. 28B, the forceps outlet port 113 and the nozzle 144 are aligned with the center cross-sectional line. Each of the illumination windows is provided with the illumination lens shown in FIG. 24 under an unshown glass cover which functions as a protective member.

The observation window is also closed by an unshown glass cover which functions as a protective member, and the objective lens 132 is disposed in the inner region protected by the glass cover. As shown in FIG. 24, the objective lens 132 may be directly exposed on the observation window.

As seen from the arrangement in FIG. 28B, the ultrasonic monitoring coverage 128 of the convex-array ultrasonic transducer 124 lies in the cross-section P1, and is a sector looking slantly forward. The optical monitoring coverage 135 of the optical monitoring means 119 is a cone centered on the monitoring center axis 135a.

In FIG. 28B, the beam coverage 123 of the treatment ultrasonic beam, the ultrasonic monitoring coverage 128, and the monitoring coverage 135 overlap. As already described, the center axis 128a of the ultrasonic monitoring coverage 128 is designed to intersect the focus 123a, and the center axis 135a of the monitoring coverage 135 of the optical monitoring means 119 is designed to intersect the focus 123a, and position setting (or positioning) is thus easily performed in treatment.

Figures 28C, 28D, 28E:
FIG. 28C to FIG. 28E are views showing shapes or forms of a therapeutic ultrasonic transducer.

The concave faced ultrasonic transducer 120 has an arc like concave shape along its longitudinal direction as shown in FIG. 28C which is the view taken along A—A line in the plan view in FIG. 28B. Electrodes are installed on both surfaces of the concave transducer, and by applying a driving signal to them, ultrasonic wave is emitted upward. A damping material is attached to the back surface of the concave surface.

The transducer may be planar as shown in FIG. 28D which is taken along B—B line in FIG. 28B, or may be transversely concave as shown in FIG. 28E. The radius of curvature in the concave in FIG. 28C is designed to be equal to that in the concave in FIG. 28E, and the emitted ultrasonic wave is focused at the same point.

When the width of the transducer is small, it may be planar as shown in FIG. 28D, and when the width of the transducer is large, it may be curved as shown in FIG. 28E to transversely focus the beam. The rest of the construction remains unchanged from the construction in FIG. 27. The first alternate example has almost the same functions as the end portion 114 in FIG. 27. In addition to the advantages of the seventh embodiment, this alternate example offers an additional advantage in which positioning is more easily performed because the center axis 128a of the ultrasonic monitoring coverage 128 is designed to intersect the focus 123a.

Figure 29:
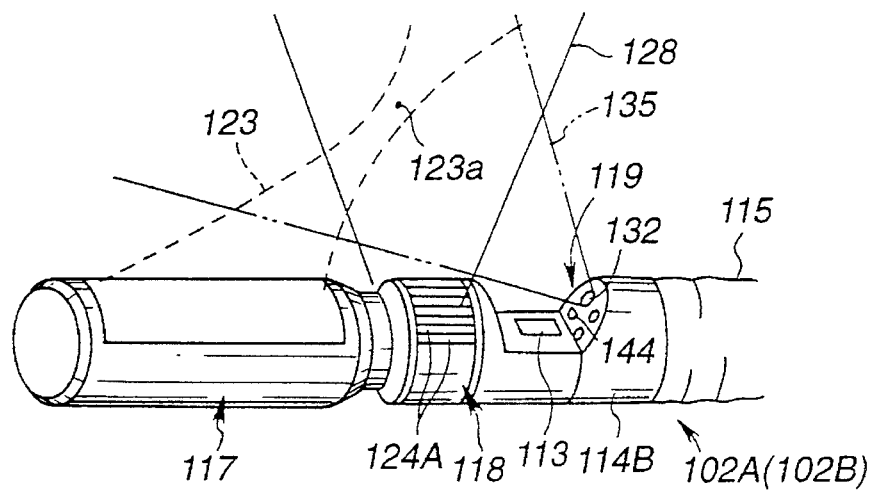

In a second alternate example with the end portion 114B in FIG. 29, the ultrasonic monitoring means 118 is made of an electronic radial-array ultrasonic transducer 124A, rather than the convex-array transducer 124 in FIG. 27 or FIG. 28A. Specifically, a number of rectangular transducers are arranged on the cylindrical surface of the end portion 114B (for example, over a certain sector if viewed from the center line of the cylinder). By allowing each transducer to transmit and then receive, the ultrasonic monitoring coverage 128 is a sector with respect to a plane perpendicular to the axis of the end portion 114B.

Although in FIGS. 27 and 28A, the forceps outlet port 113 is circular, it is now square in FIG. 29. Also in FIG. 29, the ultrasonic treatment means 117 is disposed so that the treatment ultrasonic beam 123 is slanted backward, and the focus 123a of the treatment ultrasonic beam 123 is designed to come to the center of a plane in which the ultrasonic monitoring coverage 128 lies. The advantage of this alternate example is similar to that of the first alternate example.

Figure 30:
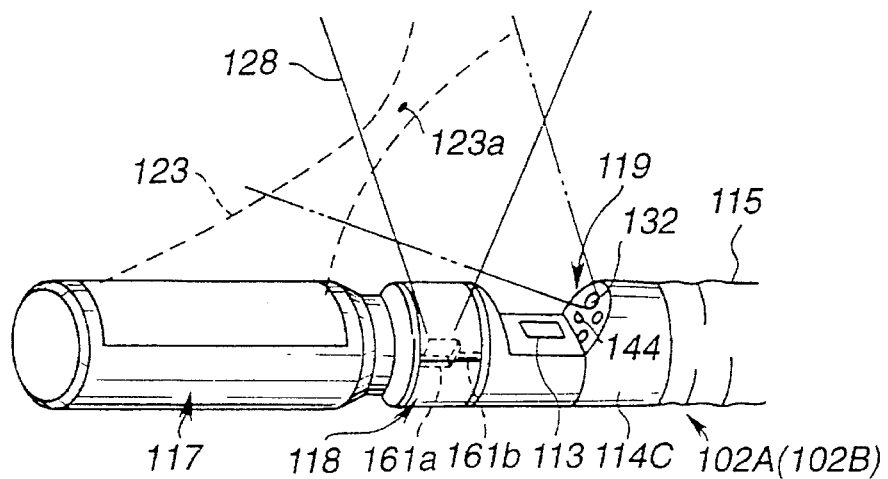

In the end portion 114C in FIG. 30, the ultrasonic monitoring means 118 is made of a mechanical radial scanning ultrasonic transducer 161a rather than the electronic radial array ultrasonic transducer 124A in FIG. 27. The mechanical radial scanning ultrasonic transducer 161a has a planar ultrasonic transducer 161a on the distal end of a flexible shaft 161b, and the proximal end of the flexible shaft 161b is rotated or reciprocated by an unshown motor. Thus, the ultrasonic transducer 161a is rotated together, or reciprocated, and as a result, ultrasonic wave is emitted in a sector with respect to a plane perpendicular to the axis of the insert portion 107.

The ultrasonic monitoring means 118 is not limited to FIGS. 27 through 30, and any other construction will do if it provides ultrasonogram.

The optical monitoring means 119 exemplifies a slantly looking optical system as preferred in the embodiment and alternate examples, but the optical monitoring means 119 is not limited to this. Other optical systems having a different viewing field are equally acceptable.

Figure 31:
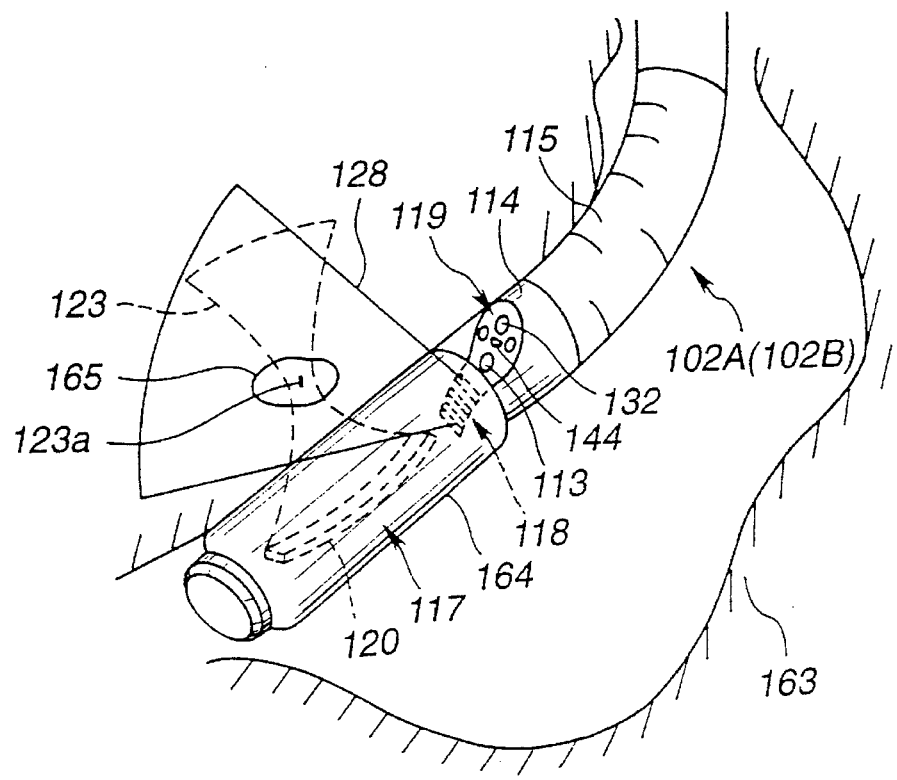

The operation of the seventh embodiment is now discussed referring to FIG. 31.

As shown in FIG. 31, the ultrasonic probe 102A (102B) constructed as above is inserted into a tract organ 163 such as the stomach. The end portion 114 is put into contact with a region of the tract wall where diagnosis and treatment are required, referring to the optical image from the optical monitoring means 119 and the ultrasonogram from the ultrasonic monitoring means 118 while performing bending operation.

As shown in FIG. 31, the ultrasonic treatment means 117 and the ultrasonic monitoring means 118 at the end portion are covered with a balloon 64 which is filled ultrasonic transmittable liquid. The treatment ultrasonic wave and the monitoring ultrasonic wave are transmitted and received via the ultrasonic transmittable liquid within the balloon 164.

When a clear vision is obstructed because the optical monitoring means 119, specifically, the outer surface of the observation window that houses the objective lens 132 is stained with mucus or humor in the course of insertion of the ultrasonic probe 102A (102B) or contacting the end portion 114, water or air is fed through the nozzle 144 to clean or dry the observation window. After a clear vision is assured, insertion operation is assumed.

The forceps outlet port 113 as the treatment function guide and its channel 142 are used to suck up humor or mucus. By operating the suction button 146 on the operation portion 108, mucus or humor is sucked up by an external suction pump. Each function of the ultrasonic probe 102A (102B) can be used in the same way an ordinary endoscope or an ultrasonic endoscope is inserted.

By allowing an unshown instrument to project from the forceps outlet port 113, for example, allowing a biopsy needle to pierce a lesion, a tissue may be sampled for examination and diagnosis.

When a lesion 165 is acquired within the ultrasonic monitoring coverage 128, and imaging is completed, the focus 123a of the treatment ultrasonic beam given by the ultrasonic treatment means 117 is aligned to the lesion 165. This is performed referring to a marker given in the ultrasonogram and the image of the lesion. The position of the end portion 114 of the ultrasonic probe 102A (102B) is set by bending operation of the bendable portion 115. In this manner, the focus is positioned such that the focus 123a is placed at the lesion 165.

After positioning the focus, the foot switch 151 is pressed to allow the driving voltage generator 122 to apply a large driving voltage, and the ultrasonic treatment means 117 outputs treatment ultrasonic wave at a power level required for cauterization. This high-powered treatment ultrasonic wave instantly raises temperature at the lesion 165, and cauterizes the lesion. cauterization through ultrasonogram from the ultrasonic monitoring means 118, high-powered treatment ultrasonic beam is directed at a lesion until denature of protein is sufficient enough to necrotize the lesion.

Then, irradiation with high-powered ultrasonic beam is stopped, treatment rate is confirmed referring the ultrasonogram. If the treatment is not sufficient enough, ultrasonic irradiation is continued further, and if a different part needs ultrasonic irradiation, it is also irradiated until full treatment is complete.

According to the seventh embodiment, the ultrasonic treatment means 117, the ultrasonic monitoring means 118, the treatment function guide, and the optical monitoring means 119 are configured on the distal end of the bendable portion 115 in an advantageous manner that permits optical monitoring, ultrasonic diagnosis and ultrasonic treatment.

The end portion 114 is inserted into the superior digestive tract or the inferior digestive tract observing an optical image, and ultrasonic thermotherapy (cauterization) can be applied to the wall surface of the digestive tract or inner organs beneath the wall surface observing ultrasonogram.

Thus, the use of the ultrasonic diagnosis and treatment system 1 greatly expands the application range of ultrasonic diagnosis and treatment.

The conventional ultrasonic probe with no bendable portion limits the sectorial range in which the ultrasonic treatment means is put into contact with the organ in which a lesion exists. The conventional probe is inserted almost in a linear manner and its end portion touches, on its side, an organ. The conventional probe is effectively used only when the lesion exists in the organ into its deep region that corresponds to the organ surface touched by the probe. Even in this case, an insertion opening is required, and if for example, making an insertion opening to the heart is an extremely risky task. Furthermore, costa presents difficulty inserting the probe. Thus, the range of application, in practice, is even narrower.

In contrast, since the first embodiment is provided with the bendable portion 115, bending the bendable portion 115 allows the side of the end portion 114 to be in contact with the organ in which a lesion exists.

Since the insert portion 107 of the first embodiment is flexible, the probe can be inserted into the body cavity through the oral cavity, the probe is inserted into organs in the body cavity without insertion opening to the abdomen and the like. In this case, insertion and positioning to a target organ is aided by observing the optical monitoring means 119. As in the endoscope, the end portion 114 can be set in the vicinity of the organ of interest, under observation using the optical monitoring means 119, and then the side of the end portion 114 is put into contact with the organ so that setup is completed to obtain ultrasonogram or echo of the lesion. When the focus 123a is aligned with the lesion, cauterization treatment is performed with the ultrasonic treatment means 117.

The seventh embodiment is thus used in a wider region than the ultrasonic probe with no bendable portion. Furthermore, since a predetermined point of the ultrasonic monitoring coverage 128 of the ultrasonic monitoring means 118 comes to the focus 123a of the ultrasonic beam derived from the ultrasonic treatment means 117, positioning for cauterization in ultrasonogram is easy and position determined can be confirmed. A lesion to be cauterized may be accurately set in the vicinity of the focus 23, and reliable cauterization results. Cauterizing normal part erroneously can be avoided.

In positioning operation as above, the ultrasonic monitoring means 118 and the ultrasonic treatment means 117 are provided on the hard end portion 114. If the bendable portion 115 on the proximal side is arbitrarily bent, the position of the focus 123a practically remains anchored to a predetermined position of the ultrasonic monitoring coverage 128 of the ultrasonic monitoring means 118. Therefore, the lesion to be cauterized can be accurately set to the focus 123a, and a reliable cauterization treatment is achieved.

Since the forceps outlet port 113 is disposed on the end portion 114, sampling the tissue of a lesion assures reliable diagnosis and treatment. In this case, if the guiding direction of the forceps outlet port 113 is set to point to the focus 123a, sampling operation is easy.

In the seventh embodiment and its alternate examples, the treatment function guide may be dispensed with, or it may be considered as part of the function of the optical monitoring means 119. In this case, the end portion 114 is constructed by arranging, from the distal side, the ultrasonic treatment means 117, the ultrasonic monitoring means 118, and the optical monitoring means 119. The bendable portion 115 is disposed on the proximal side of the end portion 114.

A eighth embodiment of the present invention is now discussed.

Figure 32:
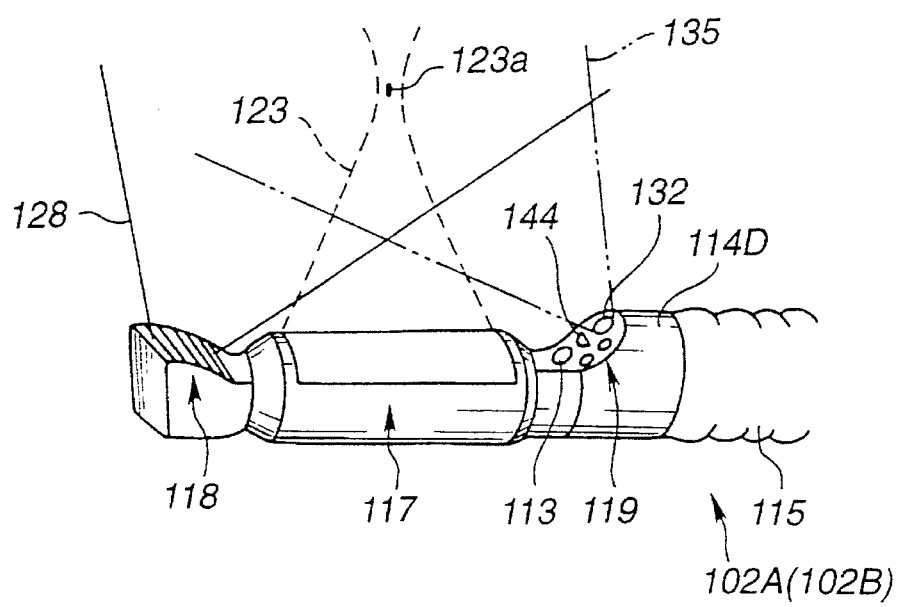
FIG. 32 to FIG. 34 relate to an eighth embodiment of the invention, FIG. 32 being a perspective view showing a distal-end side of an ultrasonic probe in the eighth embodiment.

In the seventh embodiment and its alternate examples, the ultrasonic probe 102A or 102B comprises, on the end portion 114 from its distal end, the ultrasonic treatment means 117, the ultrasonic monitoring means 118, the treatment function guide portion, and the optical monitoring means 119, and the bendable portion 115 on the proximal side of the end portion 114. It may be perfectly acceptable if a probe comprises on the end portion 114D from its distal end the ultrasonic monitoring means 118, the ultrasonic treatment means 117, the forceps outlet port 113 as the treatment function guide, and the optical monitoring means 119, and the bendable portion 115 on the proximal side of the end portion 114D as shown in FIG. 32.

In the eighth embodiment, the ultrasonic monitoring means 118 is made of a convex-array ultrasonic transducer 124. The optical monitoring means 119 has a forward slant view. In this embodiment, the beam coverage 123 of the treatment ultrasonic beam, the ultrasonic monitoring coverage 128, and optical monitoring coverage 135 are designed to overlap.

The treatment function guide may be dispensed with, or it may be considered as part of the function of the optical monitoring means 119. In this case, the end portion 114D is constructed by arranging, from the distal side, the ultrasonic monitoring means 118, the ultrasonic treatment means 117, and the optical monitoring means 119. The bendable portion 115 is disposed on the proximal side of the end portion 114D.

Figure 33:
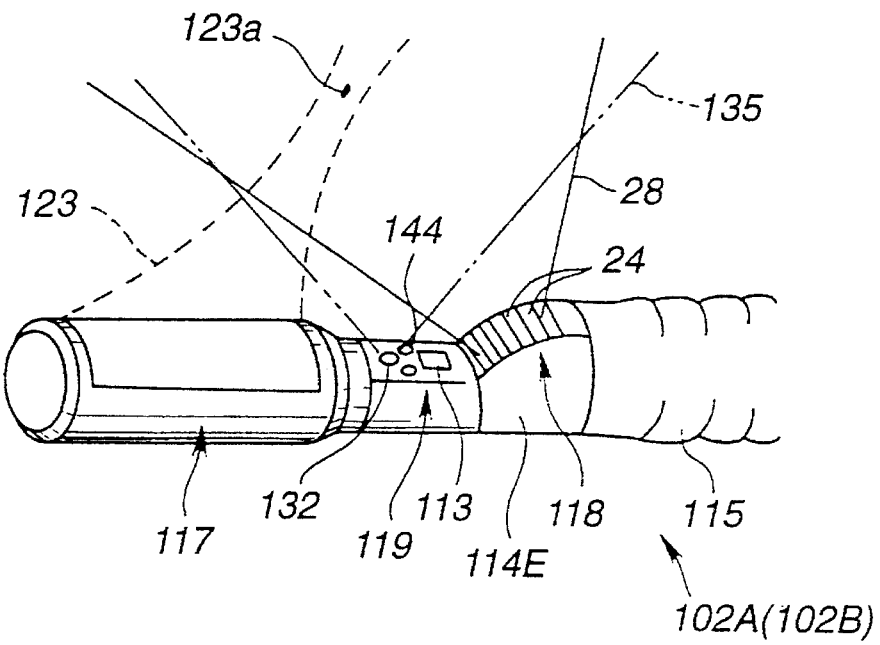

The construction shown in FIG. 33 may be used as an alternate example for the eighth embodiment. In FIG. 33, the end portion 114E is constructed by arranging, from the distal side, the ultrasonic treatment means 17, the optical monitoring means 119, the treatment function guide portion and the ultrasonic monitoring means 118. The bendable portion 115 is disposed on the proximal side of the end portion 114E.

In this alternate example, the ultrasonic monitoring means 118 is made of a convex-array ultrasonic transducer 124. The optical monitoring means 119 has a transverse view. In this alternate example, the beam coverage 123 of the treatment ultrasonic beam, the ultrasonic monitoring coverage 128, and optical monitoring coverage 135 are designed to overlap.

In FIG. 33, the treatment function guide may be dispensed with, or it may be considered as part of the function of the optical monitoring means 119. In this case, the end portion 114E is constructed by arranging, from the distal side, the ultrasonic treatment means 117, the optical monitoring means 119, and the ultrasonic monitoring means 118. The bendable portion 115 is disposed on the proximal side of the end portion 114E.

Figure 34:
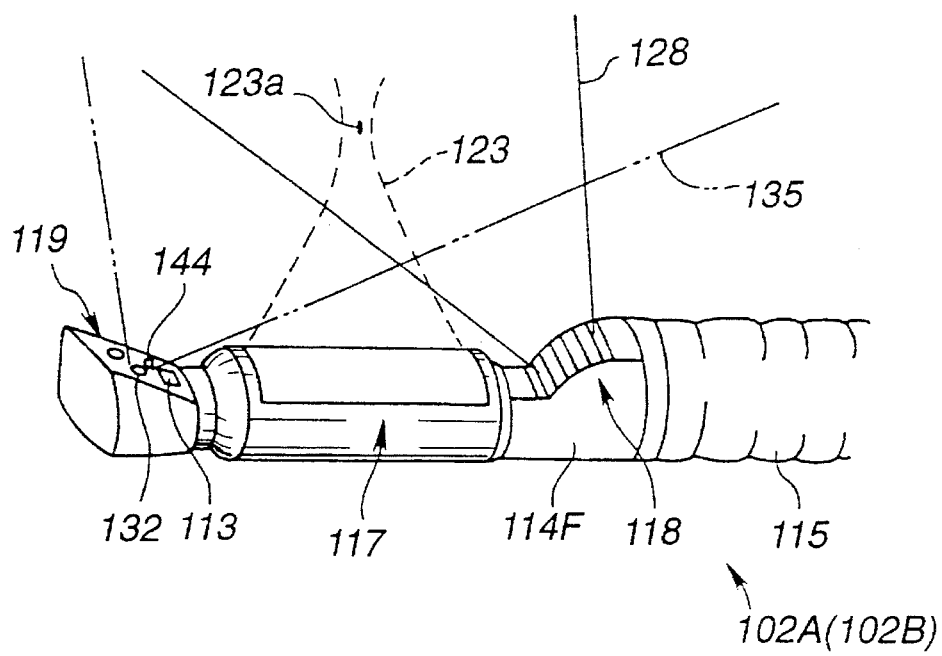

The construction shown in FIG. 34 may be acceptable. In FIG. 34, the end portion 114F is constructed by arranging, from the distal side, the optical monitoring means 119, the treatment function guide portion, the ultrasonic treatment means 117, and the ultrasonic monitoring means 118, and the bendable portion 115 is disposed on the proximal side of the end portion 114F.

In this alternate example, the ultrasonic monitoring means 118 is made of a convex-array ultrasonic transducer 124. The optical monitoring means 119 has a slantly forward view. In this alternate example, the beam coverage 123 of the treatment ultrasonic beam, the ultrasonic monitoring coverage 128, and optical monitoring coverage 135 are designed to overlap.

In FIG. 34, the treatment function guide may be dispensed with, or it may be considered as part of the function of the optical monitoring means 119. In this case, the end portion 114F is constructed by arranging, from the distal side, the optical monitoring means 119, the ultrasonic treatment means 117, and the ultrasonic monitoring means 118. The bendable portion 115 is disposed on the proximal side of the end portion 114F.

The operation of the second embodiment and its alternate examples is almost identical to that of the seventh embodiment. The eighth embodiment and its alternate examples has the same advantages as the seventh embodiment and its alternate examples. Furthermore, with the eighth embodiment and its alternate examples, a flexibility is offered in arranging and configuring each means for the ultrasonic probe.

Figure 35:
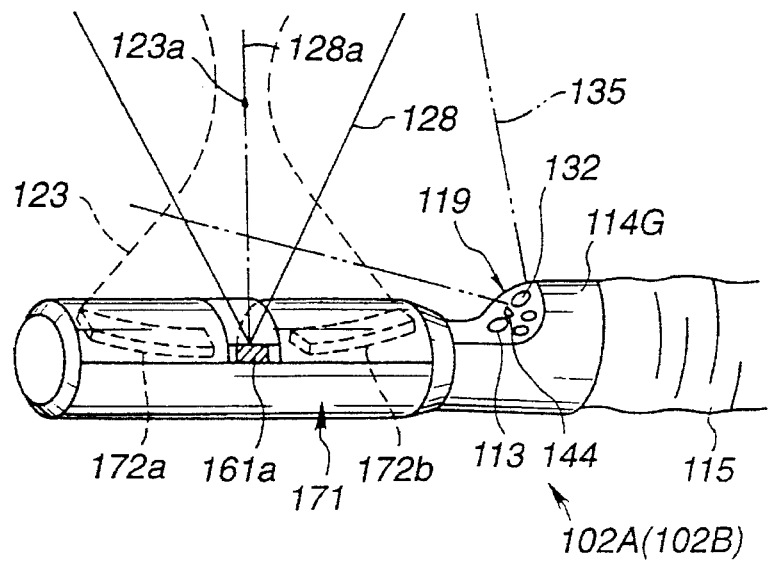
FIG. 35 to FIG. 38 relate to a ninth embodiment of the invention, FIG. 35 being a perspective view showing a distal-end side of an ultrasonic probe in the ninth embodiment.

FIG. 35 shows the construction of the end portion 114G of the ultrasonic probe 102A or 102B according to a ninth embodiment of the present invention. In the seventh and eighth embodiments (and their alternate examples), the ultrasonic treatment means 117 and the ultrasonic monitoring means 118 are separately arranged in position. In the ninth embodiment, both are integrated as an ultrasonic treatment and monitoring means 171.

In FIG. 35, the end portion 114G is constructed by arranging, from the distal side, the integrated ultrasonic treatment and monitoring means 171, the treatment function guide portion, and the optical monitoring means 119. The bendable portion 115 is disposed on the proximal side of the end portion 114G.

The integrated ultrasonic treatment and monitoring means 171 has a construction similar to the construction in which the concave faced ultrasonic transducer 120 in FIG. 27 is split into two at the bottom center of the concave, a mechanical radial scanning ultrasonic transducer 61a is disposed in the split position, and then both split concave ultrasonic transducers (172a, 172b) are placed with the mechanical radial scanning ultrasonic transducer 61a therebetween along the axis of the end portion 114.

The mechanical radial scanning ultrasonic transducer 161a functions as the ultrasonic monitoring means for the ultrasonic treatment and monitoring means 171, the two concave ultrasonic transducers 172a, 172b on both sides of the mechanical radial scanning ultrasonic transducer 161a functions as the ultrasonic treatment means.

As already described, the mechanical radial scanning ultrasonic transducer 161a is connected to a flexible shaft (not shown in FIG. 35), and this shaft is driven by a motor, and an ultrasonic monitoring coverage 128 is formed in a sector if viewed in a plane perpendicular to the axis of the insert portion.

In this embodiment, the optical monitoring means 119 has a slantly forward view. Like the previous embodiment, the beam coverage 123 of the treatment ultrasonic beam, the ultrasonic monitoring coverage 128, and optical monitoring coverage 135 are designed to overlap.

The two concave ultrasonic transducers 172a, 172b are symmetrically disposed on both sides of the mechanical radial scanning ultrasonic transducer 161a.

As shown in FIG. 35, the mechanical radial scanning ultrasonic transducer 161a and the concave ultrasonic transducers 172a, 172b are arranged such that the center axis 128a of the ultrasonic monitoring coverage 128 intersects the focus 123a of the treatment ultrasonic beam.

Figure 36:
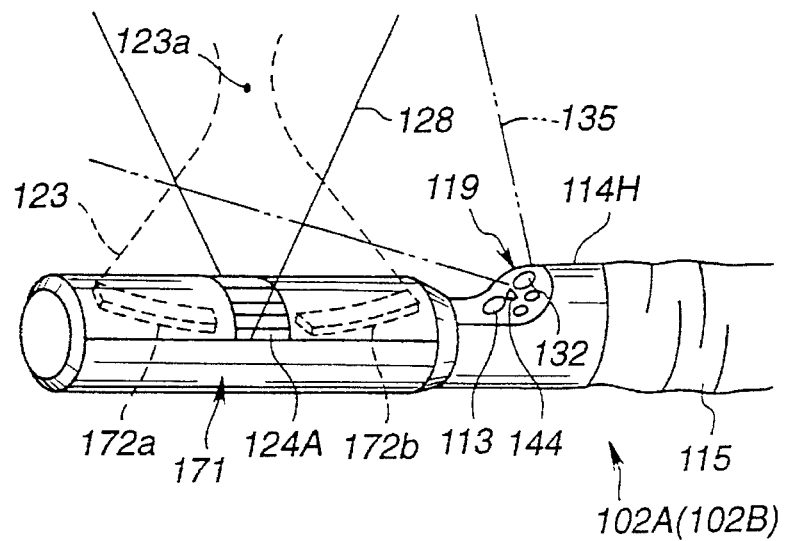

In FIG. 35, the mechanical radial scanning ultrasonic transducer 61a is disposed between the concave ultrasonic transducers 172a, 172b, an alternate example of the end portion 114H as shown in FIG. 36 is also acceptable wherein the electronic radial scanning ultrasonic transducer 124A is employed instead. No substantial difference exists in operation and advantage between FIG. 35 and FIG. 36, except for the driving method for the ultrasonic monitoring means.

Figure 37:
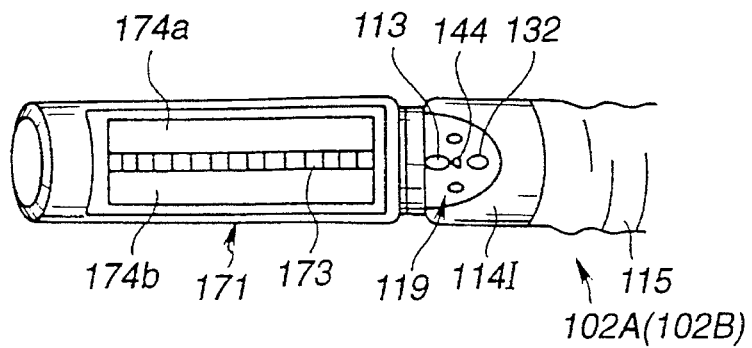

An alternate example of the end portion 114I as shown in FIG. 37 is also acceptable wherein the electronic linear scanning ultrasonic transducer 173 is employed instead. In FIG. 37, the end portion 114I is constructed by cutting the concave ultrasonic transducer 120 by the cross-section line P1 in FIG. 28B, disposing the electronic linear scanning transducer 173 along the cut line P1, and disposing two cut concave ultrasonic transducers (174a, 174b) on both sides of the electronic linear scanning transducer 173.

The electronic linear scanning transducer 173 offers its ultrasonic monitoring coverage in a plane in perpendicular to the sheet of FIG. 27, the plane in which the line of transducer layout (the axis of the insert portion) lies. By performing phase control, for example, by allowing a delay element or the like to shift the timing of application of each transmission pulse to each transducer 173 in the transmission and reception of the ultrasonic wave, a sectorial ultrasonic monitoring coverage is formed in which the axis of the insert portion.

The treatment ultrasonic beam derived from the two concave ultrasonic transducers 174a, 174b lies in a plane in which the ultrasonic monitoring coverage lies in, and their focus comes to the center line of the ultrasonic monitoring coverage.

Figure 38:
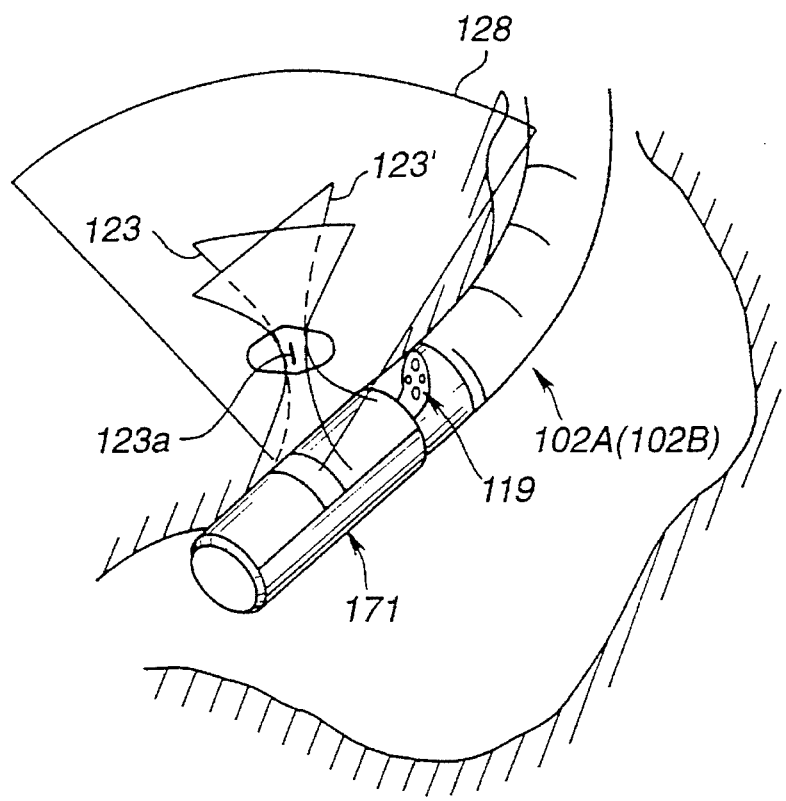

FIG. 38 shows the operation of the ninth embodiment. In FIG. 38, reference numeral 123' designates the beam coverage of the treatment ultrasonic beam, which is transversely focussed, and longitudinally focussed at the focus 123a with respect to the transducer surface (in FIG. 36, the ultrasonic transducers 172a, 172b are longitudinally and transversely concave). The ninth embodiment has the same advantages as the seventh embodiment and its alternate examples.

Furthermore, in this embodiment, setting the focus of the treatment ultrasonic wave to the center line of the monitoring coverage is easy, and this setting can be maintained when the focus of the treatment ultrasonic wave (although in the first alternate example of the seventh embodiment (refer to FIG. 28A, for example), it is possible to set the focus of the treatment ultrasonic beam to the center line of the monitoring coverage, the position of the focus will come off from the center line of the monitoring coverage if the focus of the treatment ultrasonic wave is repositioned. In contrast, in the third embodiment, the focus position shifts along the center line of the monitoring coverage even when the focus of the treatment ultrasonic wave is repositioned).

This embodiment constructed as above facilitates positioning and setting for ultrasonic treatment, and offers a substantially improved efficiency in ultrasonic diagnosis and treatment.

The ultrasonic treatment transducers are not limited to those in FIG. 35 through FIG. 37. As in the previous embodiments, the ultrasonic treatment transducers may be a single or a plurality of longitudinally concave one, phased array one. Also, any other structure that presents focussed ultrasonic beam is acceptable as long as it is associated by driving means.

The ultrasonic monitoring transducers are not limited to those in FIG. 35 through FIG. 37, any type is acceptable as long as it can be integrated with the ultrasonic treatment transducer.

Discussed in the seventh through ninth embodiments and their alternate examples are one probe type that comprises on the distal side of the bendable portion 115 the ultrasonic treatment means 117, the ultrasonic monitoring means 118, the treatment function guide portion, and the optical monitoring means 119 and another probe type that comprises the same components as above but with the ultrasonic treatment means 117 and the ultrasonic monitoring means 118 reversed in positional order. In addition, still another type is acceptable in which the ultrasonic treatment means 117, the ultrasonic monitoring means 118, the treatment function guide, and the optical monitoring means 119 in that order from the distal end.

Another type also acceptable comprises on the distal end of the bendable portion 115, at least, the ultrasonic treatment means 117, the ultrasonic monitoring means 118, the treatment function guide portion and the optical monitoring means 119.

Also acceptable is another type without the treatment function guide that comprises on the distal end of the bendable portion 115, at least, the ultrasonic treatment means 117, the ultrasonic monitoring means 118, and the optical monitoring means 119.

Figure 39:
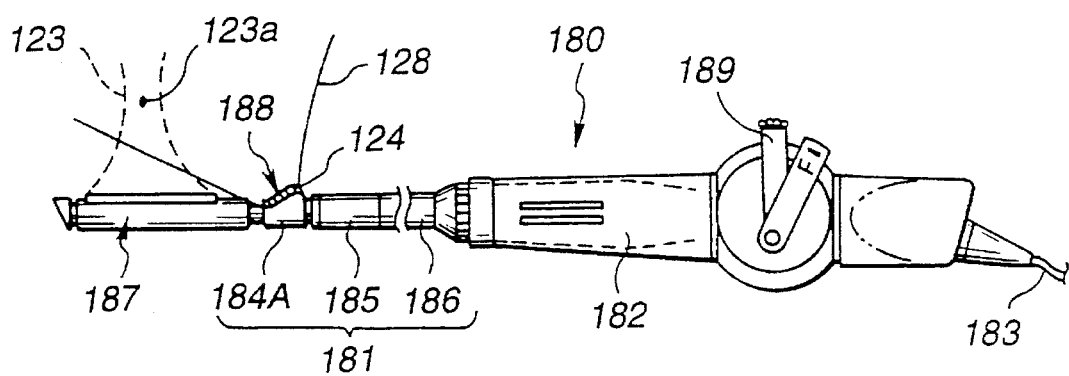
FIG. 39 and FIG. 40 relate to a tenth embodiment of the invention, FIG. 39 being a summary view showing an outer appearance of an ultrasonic probe in the tenth embodiment.

FIG. 39 shows the ultrasonic probe 180A according to a tenth embodiment of the present invention. The ultrasonic probe 180A is constructed of a small tube (capillary) insert portion 181, a wide operation portion 182 which is formed on the proximal of the insert portion 181 and which is gripped by an operator for insertion and bending operations, and a universal cable 183 extended from the operation portion 182, wherein the universal cable 183 is connected to the ultrasonic monitoring apparatus 105 (refer to FIG. 24).

The insert portion 181 comprises way from its distal end a hard end portion 184A, a bendable portion 185, and a hard small tube portion 86. The end portion 184A comprises way from its distal end an ultrasonic treatment means 187 and an ultrasonic monitoring means 188 along the axis of the insert portion 181. The bendable portion 185 is disposed on the proximal side of the end portion 184A.

The ultrasonic treatment means 187 is constructed of a concave ultrasonic transducer as shown in FIG. 24, and a driving voltage generator 122 in the ultrasonic diagnosis and treatment apparatus 105 (see FIG. 24) applies a driving voltage to the ultrasonic treatment means 187 via an unshown signal line routed through the insert portion 181. Thus, the treatment ultrasonic beam having a directivity pattern such as a beam coverage 123 is focussed at a focus 123a as shown by the dotted line in FIG. 39.

The ultrasonic monitoring means 188 is constructed of a convex-array ultrasonic transducer 124, and connected via an unshown signal line to a transmission pulse generator circuit 126 and the receiver processing circuit 127 (see FIG. 24), which form a signal processing system 105A. Then, the ultrasonic beam scans an ultrasonic monitoring coverage 128 as shown by fine lines as shown in FIG. 39. An operation portion 182 is provided with an angle knob 189 which controls the direction to which the bendable portion 185 bends.

As in the previous embodiments, the ultrasonic treatment transducer may be a single or a plurality of longitudinally concave one, square concave one, and phased array one. Also, any other structure that presents focussed ultrasonic beam is acceptable as long as it is associated by driving means.

FIG. 39 shows the convex-array ultrasonic transducer 124 as an example of the ultrasonic monitoring means 188. The ultrasonic monitoring means 188 is limited to this. Any structure is perfectly acceptable as long as it presents ultrasonogram for diagnosis.

Figure 40:
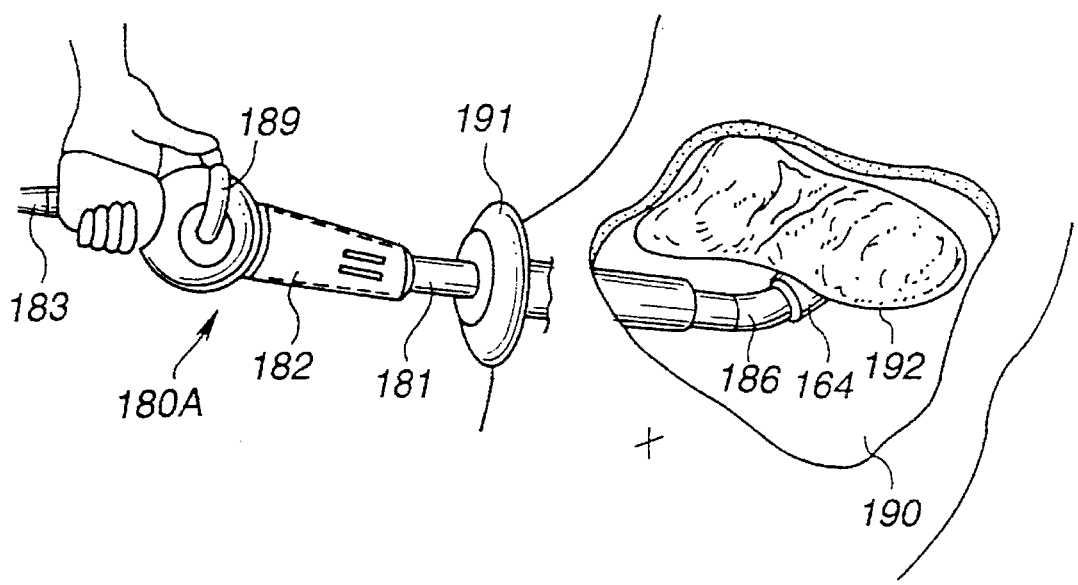

As shown in FIG. 40, the ultrasonic probe 180A constructed as above is inserted via a trocar 191 into the abdominal cavity 190 that has beforehand been fed with air by pneumoperitoneum. Observing optically using an unshown hard endoscope, bending operation is performed so that the end portion 184A is put into contact with an organ 192 to be treated in the abdominal cavity 192, via a balloon

164.

Thereafter, ultrasonic diagnosis and treatment are performed in the same manner as in previous embodiments.

According to this embodiment, the ultrasonic probe comprises the insertion portion provided with the ultrasonic monitoring function, the ultrasonic treatment function, and the insertion and bending function. The ultrasonic probe may be inserted into the thoracic cavity, the abdominal cavity or cerebral ventricles, and ultrasonic thermotherapy may be performed referring to ultrasonogram of a organ deep in the body cavity. The ultrasonic probe according to this embodiment thus expands its application for ultrasonic diagnosis and treatment in the body cavity.

Figure 41:
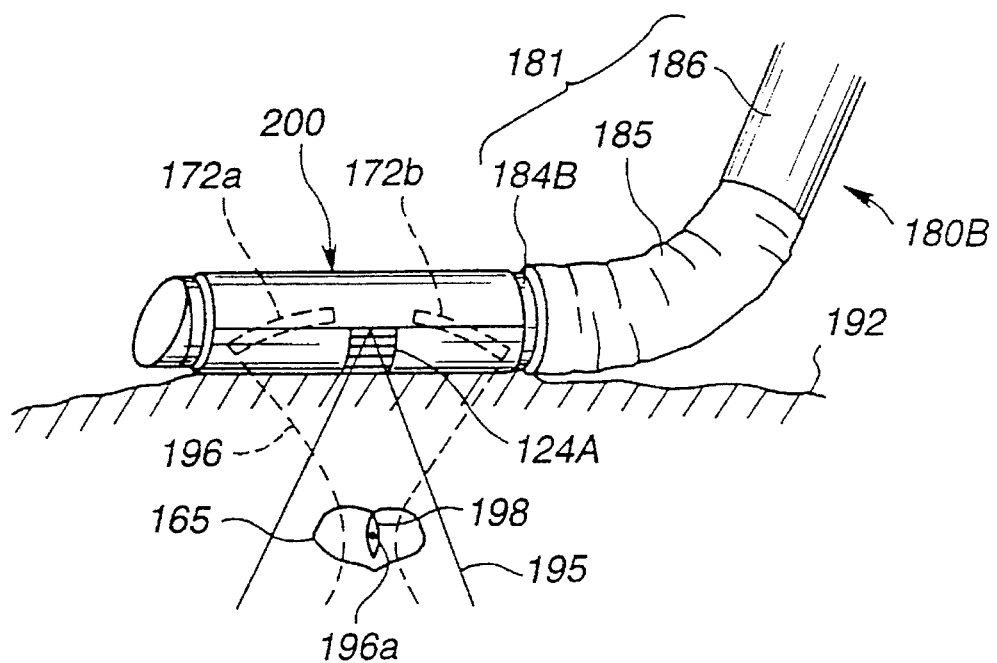
FIG. 41 to FIG. 43 relate to an eleventh embodiment of the invention, FIG. 41 being a perspective view showing a distal-end side of an ultrasonic probe in the eleventh embodiment.

FIG. 41 shows the end portion 184B of the ultrasonic probe 180B according to a eleventh embodiment of the present invention.

In this embodiment, the ultrasonic treatment means and the ultrasonic monitoring means are integrated as an ultrasonic treatment and monitoring means 200. The end portion 284B made of the ultrasonic treatment and monitoring means 200 is connected to the bendable portion 185.

In this embodiment, in the ultrasonic diagnosis and treatment system having a hard small tube with the bendable portion 185 that can be inserted into the body cavity, the insert portion 180B comprises the end portion 184B that is constructed of the ultrasonic treatment and monitoring means 100 for diagnosing and treating a living body, and the bendable portion 185 that is disposed on the proximal end of the end portion 184B along the axis of the insert portion 181.

As shown in FIG. 41, the ultrasonic treatment and monitoring means 200 comprises two split ultrasonic treatment transducers 172a, 172b (for example, similarly as shown in FIG. 27) as the ultrasonic treatment transducer and an electronic radial scanning ultrasonic transducer 124A as the ultrasonic monitoring transducer.

Disposed on the proximal side of the bendable portion 185 is a hard small tube 186, and the structure on the proximal side of the bendable portion 185 has the same outline as that of FIG. 40.

The ultrasonic treatment transducer is not limited to the one in FIG. 41. As in the previous embodiments, the ultrasonic treatment transducer may be a single or a plurality of longitudinally concave one, square concave one, and phased array one. Also, any other structure that presents focussed ultrasonic beam is acceptable as long as it is associated with driving means.

FIG. 41 also shows how treatment is performed. For example, as shown in FIG. 40, the probe is inserted via a trocar 191 into the abdominal cavity 190 to allow the end portion 184B to be in contact with an organ 192 in the abdominal cavity 190. The center axis of the ultrasonic monitoring coverage 195 is set to the lesion 164 observing ultrasonogram in the ultrasonic monitoring coverage 195 derived from the electronic radial scanning ultrasonic transducer 124A as the ultrasonic treatment transducer.

From ultrasonogram, by allowing the image of a lesion 165 to be placed in a position corresponding to the focus along the center axis of the treatment transducers 172a, 172b, the foot switch or the like is switched on to allow the treatment ultrasonic beam to be emitted from the ultrasonic treatment transducers 172a, 172b.

The treatment ultrasonic beam is emitted such that it is focussed at a focus 196a within the beam coverage 196 as shown by dotted lines in FIG. 41. Thus, the lesion 165 is set in the vicinity of the focus 196a within the beam coverage 196.

The advantage of this embodiment is identical to that of the seventh embodiment. Furthermore, since it is possible to place the focus of the treatment ultrasonic wave on the center axis of the ultrasonic monitoring coverage, the ease with which treatment is done by means of ultrasonic wave is substantially improved, resulting in an substantially improved efficiency in ultrasonic diagnosis and treatment.

Figure 42:
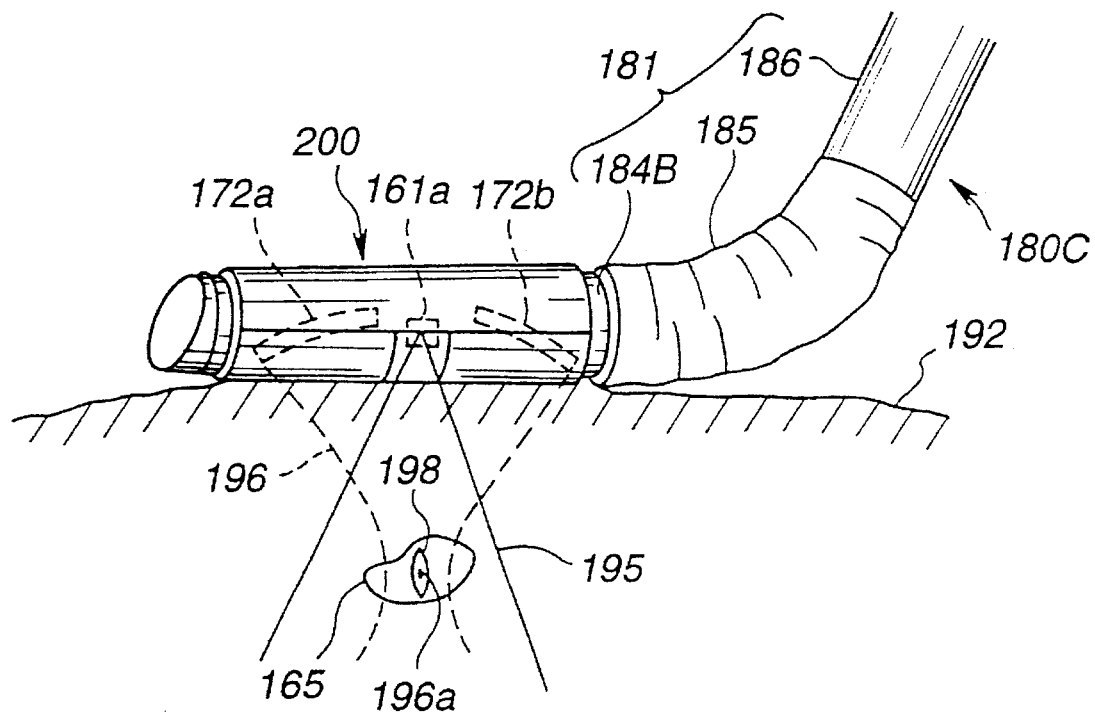

The ultrasonic monitoring transducer may be an ultrasonic probe 180C made of the ultrasonic treatment and monitoring means 200 constructed of the mechanical radial scanning transducer 161a in FIG. 42 instead of the electronic radial array ultrasonic transducer 124A in FIG. 41.

Figure 43:
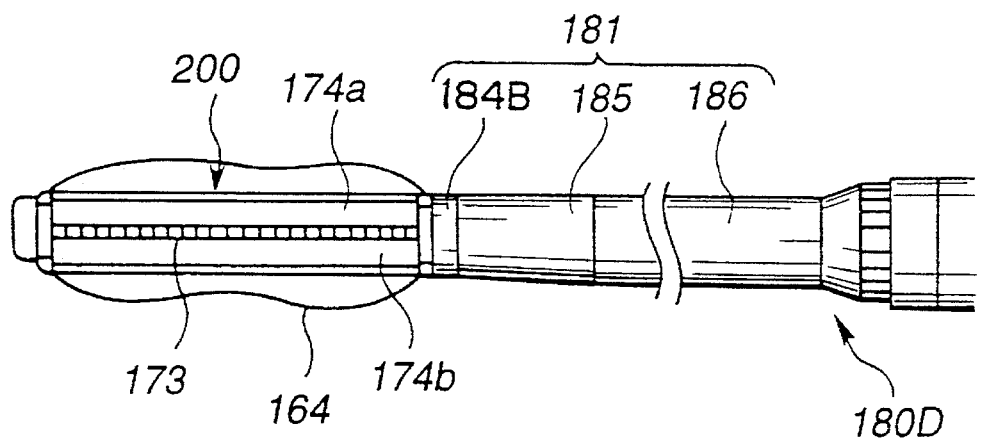

Also acceptable is an ultrasonic probe 180D which is made of the ultrasonic treatment and monitoring means 200 comprising the electronic linear scanning ultrasonic transducer 173 as in FIG. 37 disposed on the end portion 184B as shown in FIG. 43, and a pair of concave ultrasonic transducers 174a, 174b disposed on both sides of the electronic linear scanning ultrasonic transducer 173.

FIG. 43 shows the state in which a balloon 164 is installed.

The ultrasonic monitoring transducer is not limited to alternate examples in FIG. 42 and FIG. 43, and any structure will be acceptable as long as it can be integrated with the ultrasonic treatment transducer.

The operation and advantage of this alternate example remain unchanged from those of the eleventh embodiment.

Although the optical monitoring means is not provided in the ultrasonic probe 180A and 180B according to the tenth and eleventh embodiments (and their alternate examples), the ultrasonic probe may be provided with an optical monitoring means.

In the seventh through eleventh embodiments, the ultrasonic probe has been quoted as performing thermotherapy (cauterization) using ultrasonic wave.

The ultrasonic probe is not only applied to this, but also to other ultrasonic treatments including thermotherapy from within the body cavity, lithodialysis using ultrasonic wave, and acceleration of litholysis using ultrasonic wave.

Figure 44:
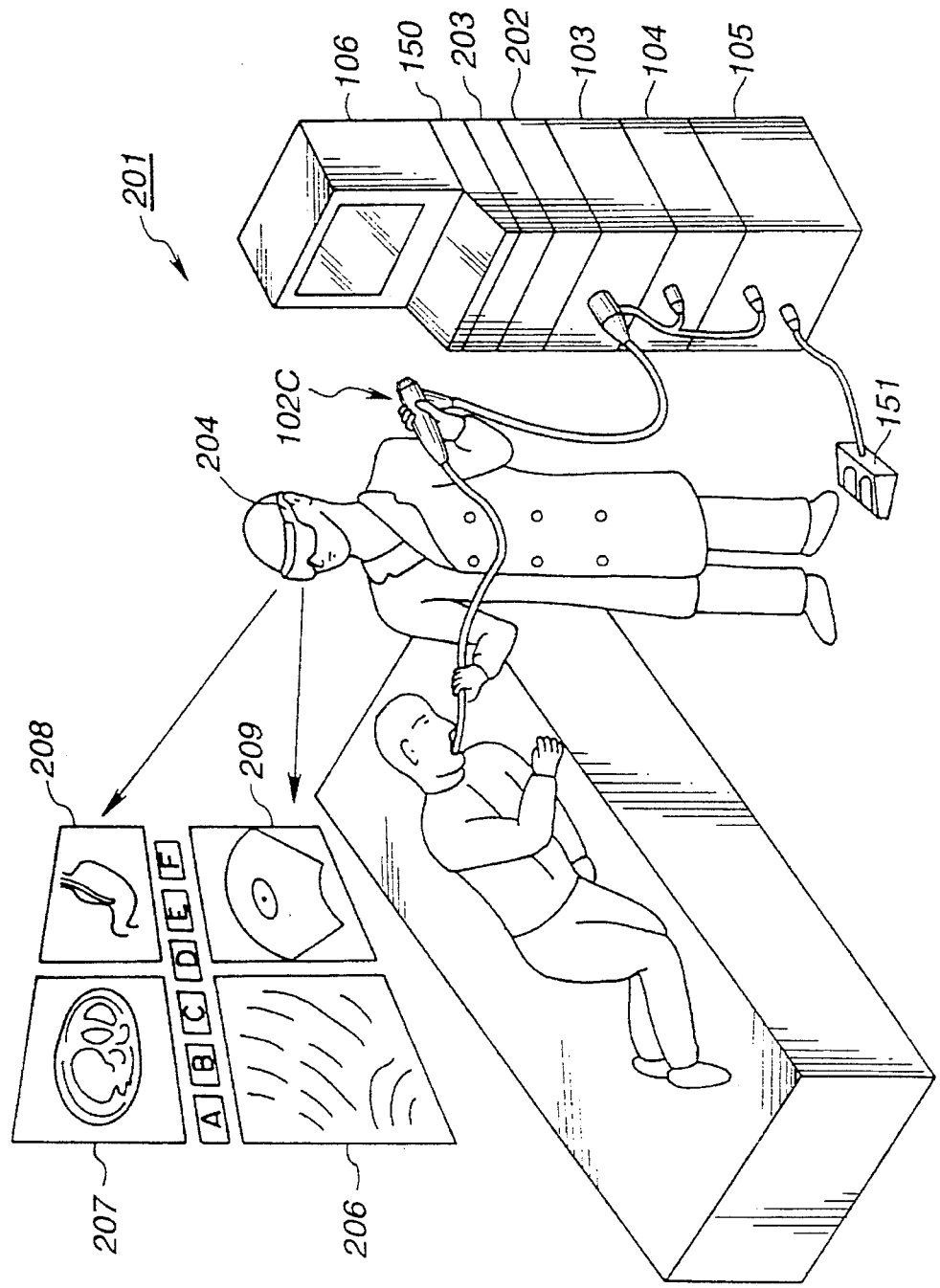
FIG. 44 is an explanatory view showing a whole arrangement of an ultrasonic diagnosis and therapy system according to a twelfth embodiment of the invention.

FIG. 44 shows generally the ultrasonic diagnosis and treatment system 201 according to a twelfeth embodiment of the present invention.

In addition to the system shown in FIG. 24, this embodiment comprises an image filing device 202, an image processor device 203, a face mount display (or head mount display, referred to as HMD hereinafter) 204.

The system 201 uses an ultrasonic probe 102C which comprises an optical monitoring means with two objective lenses and two CCDs. The endoscopic images picked up by two CCDs are signal processed by CCU 104 into video signal, which are output to a color monitor 106 via a superimposing circuit and the like. The video signals are also fed to the image processor device 203, where two video signals having parallax there between are processed and reproduced into an image with artificial reality attached.

The reproduced image with artificial reality attached is sent to HMD 204 from a video switch circuit via an unshown cable, and HMD 204 presents on its two liquid crystal displays the reproduced image 206 with artificial reality attached. X-ray image 208 and X-ray computer tomography image 207 stored in the image filing device 202, and ultrasonogram 209 derived from the ultrasonic monitoring means 118 can be sent to HMD 204 via the image switch circuit.

Also input to the image processor device 203 is the ultrasonogram that has been picked up and processed by the ultrasonic monitoring means 118.

The image processor device 203 processes the ultrasonogram so that it may be superimposed onto the reproduced image with artificial reality attached, subsequently for them to be output to HMD 204 via the image switch circuit.

The HMD 204 is provided with an unshown sensor which detects an operator's line of sight, and the detected line of sight signal is sent to a controller which controls display switching. In response to the detected signal, the controller switches video output to HMD 204. Depending on the position of the line of sight, the liquid crystal display is set to a semi-transparent state so that the operator can look a patient through the displayed image and the liquid crystal display.

In this embodiment, the operator who uses, wearing HMD 204, the ultrasonic diagnosis and treatment system is able to look a variety of images simultaneously or switchably in his vision.

Since the operator can look a plurality of images in his vision, there is no need for him to look different images on different monitors. This results in a substantially improved efficiency in diagnosis and treatment.

A thirteenth embodiment of the present invention is now discussed. First, the background of this embodiment is described. The ultrasonic treatment apparatus disclosed in PCT WO93/16641 is provided with an ultrasonic monitoring means which provides ultrasonogram by which diagnosis of a lesion and setting of a treatment are performed. In such a case, an image area available for diagnosis is limited, and furthermore, the use of a single means only prevents multiple-source diagnosis.

In view of this, the thirteenth through fifteenth embodiments and their alternate examples provide a diagnosis and treatment system which combines an external image diagnosis device and an ultrasonic diagnosis and treatment system so that multiple-source diagnosis may be achieved.

This embodiment is constructed of a diagnosis and treatment system having a small tube with a bendable portion that can be inserted into the body cavity and a combined external image diagnosis device. This embodiment thus performs image diagnosis and positioning of the small tube.

Figure 45:
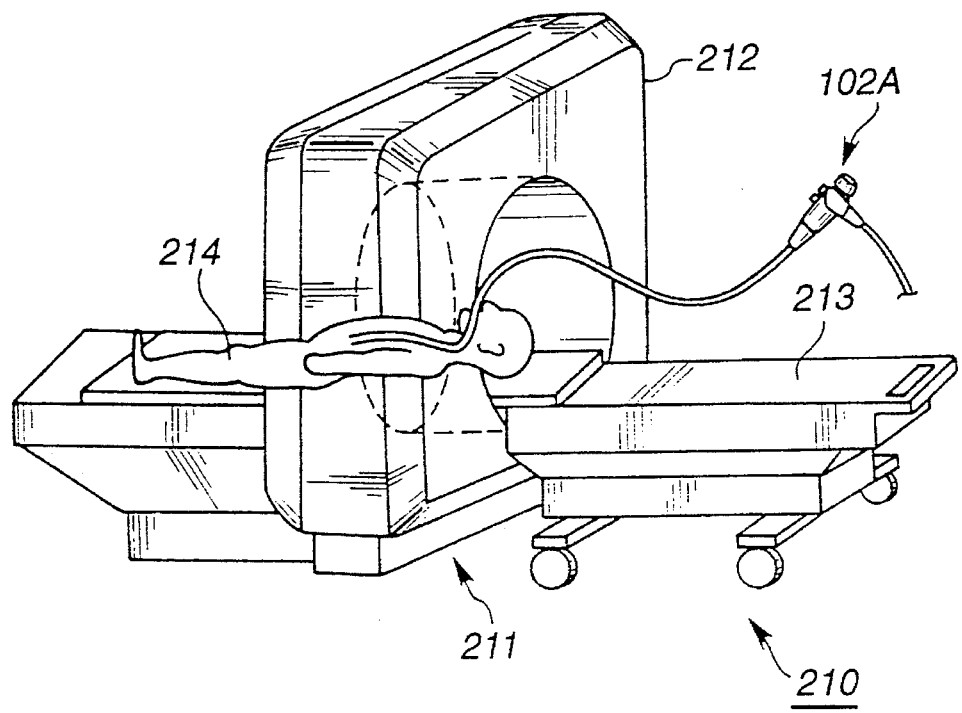
FIG. 45 is an explanatory view showing a principle part of an ultrasonic diagnosis and therapy system according to a thirteenth embodiment of the invention.
Figure 46:
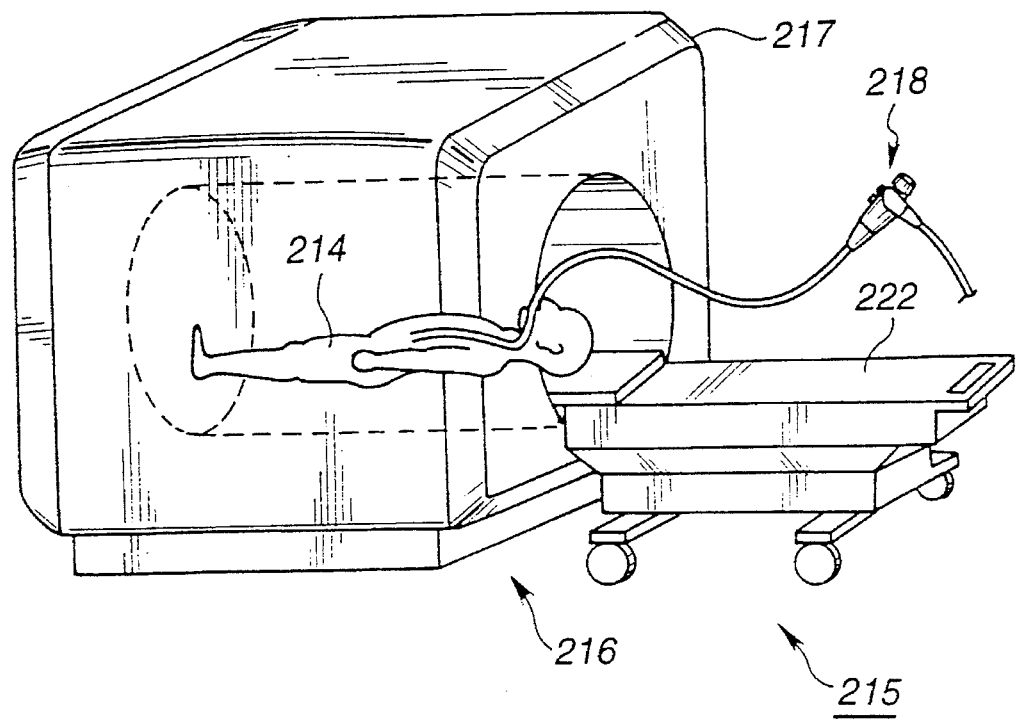
FIG. 46 is an explanatory view showing a principle part of a diagnosis and therapy system according to a fourteenth embodiment of the invention.
Figure 47:
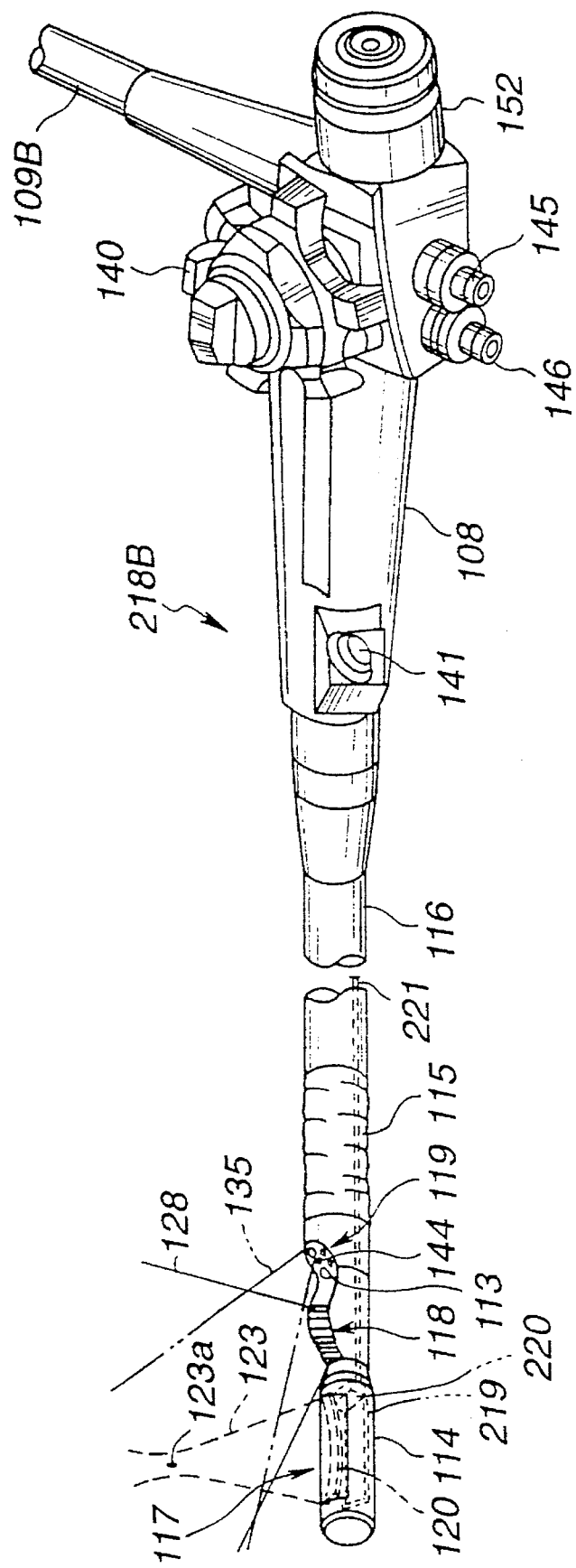
FIG. 47 to FIG. 50 relate to a fifteenth embodiment of the invention, FIG. 47 being a perspective view showing an arrangement of an ultrasonic probe in the fifteenth embodiment.
Figure 48:
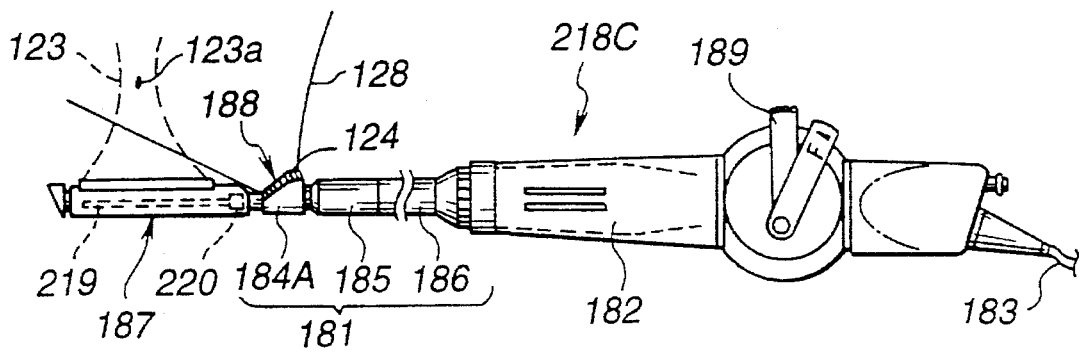
Figure 49:
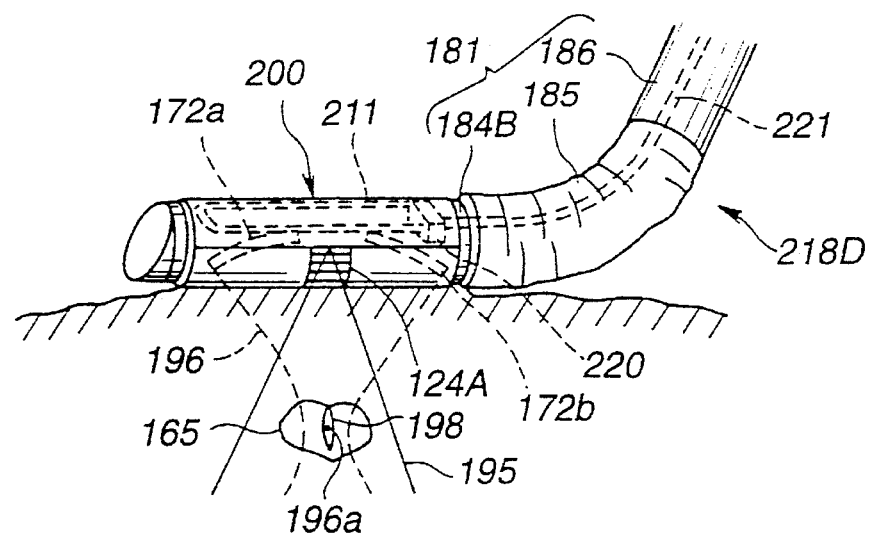
Figure 50:
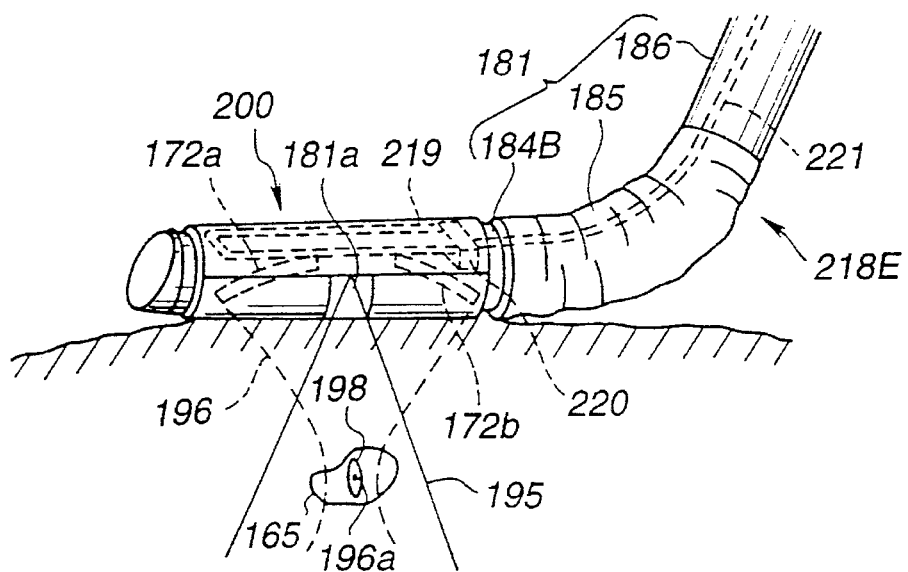

This embodiment may comprise a flexible insert portion as shown in FIGS. 45 through 47 like the previous embodiments or may comprise a hard insert portion as shown in FIGS. 48 through 50.

FIG. 45 partially shows a diagnosis and treatment system 210 wherein the external image diagnosis device is an X-ray computer tomograph.

The thirteenth embodiment of the diagnosis and treatment system 210 is constructed by combining the ultrasonic diagnosis and treatment system 101 (hereinafter referred to as main system) in FIG. 24 with the X-ray computer tomograph 211 (X-ray computer tomograph device including an image processor device) in FIG. 45.

Although the main system and the X-ray CT 211 are separately housed, both X-ray CT image and ultrasonogram from the ultrasonic probe 102A are observed for diagnosis and treatment.

Otherwise, the output from an unshown video output device of the X-ray CT device and the video output from the main system are connected to an image processor device such as CCU 104 in FIG. 24 (or a video processor), and the image processor device is connected to the color monitor 106 (see FIG. 24) where the image from the X-ray CT device corresponding to the external diagnosis device and the ultrasonogram from the main system are simultaneously or switchably displayed.

In the diagnosis and treatment system 210 constructed above, along with normal X-ray CT check, the ultrasonic diagnosis probe 102A shown in FIG. 25 is inserted in the body cavity, tract organs, the abdomen cavity, the thoracic cavity, or the cerebral ventricle of the patient 214 who is lying down on the bed 213 that is connected to a gantry 212.

X-ray tomogram image of a lesion is obtained from the X-ray CT device, and the lesion is diagnosed while the end portion of the ultrasonic probe 102A is checked. Further, ultrasonogram image is obtained from the ultrasonic probe 102A. Ultrasonogram image from within the body cavity and the X-ray tomogram image are examined for diagnosing the lesion, and determination of treatment area and positioning of the end portion of the ultrasonic probe are performed.

In this case, an operator may observe different image diagnosis devices (X-ray CT 211 and the ultrasonic probe 102A) for different image diagnosis on their respective display means. Using the image processor device according to this embodiment, however, different images from different image diagnosis devices are presented on the same display means.

Otherwise, as described in the twelfth embodiment in FIG. 44, video signals are processed and reproduced into an image with artificial reality attached by the image processor device 203, and the video output from the image processor device 203 is sent to MHD 204, which in turn provides a diversity of images, simultaneously or one by one switchably, into the vision of the operator who operates it.

Thereafter, ultrasonic treatment resumes as in the previous embodiments.

According to this embodiment, by performing image diagnosis, in particular, X-ray CT image diagnosis, in addition to ultrasonogram diagnosis using the ultrasonic probe, diagnosis of a lesion to be ultrasonically treated, determination and setting of treatment area, positioning of the ultrasonic probe end portion and its verification can be performed reliably and accurately based on a plurality of pieces of information.

FIG. 46 shows an fourteenth embodiment of the present invention, a diagnosis and treatment system 215 wherein the external image diagnosis device is a magnetic resonance imaging device (hereinafter referred to as MRI device) 216.

Since the MRI device 216 acquires MR signal for imaging under the presence of a high-intensity static magnetic field that is caused by a magnetic gantry 217, an ultrasonic probe 218 which is used in combination with the MRI device 216 should be designed to work under the strong magnetic field.

The diagnosis and treatment system 215 comprises the small tube (corresponding to the ultrasonic probe) which is constructed of non-magnetic or weak-magnetic material that has no effect on imaging process of the MIR device 216.

In the diagnosis and treatment system 215 constructed above, like normal MRI check, the ultrasonic diagnosis probe 218 is inserted in a tract organ, the abdomen cavity, the thoracic cavity, or the cerebral ventricle of the patient 214 who is lying down on the bed 220 that is connected to a magnet gantry 217. The operation thereafter is almost identical to that for the thirteenth embodiment.

According to this embodiment, by performing image diagnosis, in particular, MRI diagnosis, in addition to ultrasonogram diagnosis using the ultrasonic probe, diagnosis of a lesion to be ultrasonically treated, determination and setting of treatment area, positioning of the ultrasonic probe end portion and its verification can be performed reliably and accurately based on a plurality of pieces of information.

A fifteenth embodiment of the present invention is shown in FIG. 47 wherein an ultrasonic probe 218B contains in an end portion 114 a high-frequency coil 219 for receiving MR signal.

The ultrasonic probe 218B in FIG. 47 is constructed of the ultrasonic probe 102B in FIG. 26 and the high-frequency coil 219 contained therein. The high-frequency coil 219 made of a loop antenna may be disposed inside the ultrasonic treatment means 117, the ultrasonic monitoring means 118 or the optical monitoring means 119.

The output of the high-frequency coil 219 is coupled to an impedance matching circuit 220, and the output of the impedance matching circuit 220 is coupled to a cable 221. Thus, the MR signal picked up by the high-frequency coil 219 is sent externally outside of the ultrasonic probe 218B, and fed to a signal input of the MRI device 216.

In FIG. 47, the high-frequency coil 219 is installed into the end portion 114 of the ultrasonic probe 102B.

Alternatively, the high-frequency coil 219 is installed into the end portion 114 of the ultrasonic probe 102A in FIG. 25.

FIG. 48 through FIG. 50 show alternate examples of the fifteenth embodiment, ultrasonic probe 218C through 218E.

The ultrasonic probes 218C through 218E shown in FIG. 48 through FIG. 50 are provided with rigid insert portions 181. The ultrasonic diagnosis and treatment system is constructed by mounting the high-frequency coil 219 that receives MR signal into the small tube end portion 184A or 184B in the rigid insert portion 181.

In FIG. 48, the high-frequency coil 219 is mounted into the end portion 184A of the ultrasonic probe 180A in FIG. 39, and in FIG. 49, the high-frequency coil 219 is mounted into the end portion 184B of the ultrasonic probe 180B in FIG. 41, and in FIG. 50, the high-frequency coil 219 is mounted into the end portion 184B of the ultrasonic probe 180C in FIG. 42.

In the ultrasonic probes 218C through 218E, the high-frequency coil 219 made of a loop antenna is mounted into the ultrasonic treatment means 187, the ultrasonic treatment and monitoring means 200 or the ultrasonic monitoring means 188, in the same way as in the ultrasonic probe 218B in FIG. 47. The MR signal picked up the high-frequency coil 219 is sent to the signal input of the MRI device via the impedance matching circuit 220 and the cable 221.

The arrangement for displaying the image derived from the MRI device and the image derived from the ultrasonic probe remains unchanged from that for the eighth embodiment.

In the diagnosis and treatment system in the alternate example, like normal MRI check, any of the ultrasonic diagnosis probes 218C through 218E is inserted in a tract organ, the abdomen cavity, the thoracic cavity, or the cerebral ventricle of the patient who is lying down on the bed 220 that is connected to a magnet gantry 217. The operation thereafter is almost identical to that for the fifteenth embodiment.

Using the MR signal receiving high-frequency coil mounted in the ultrasonic probes 218C through 218E, a high-resolution internal MRI image is picked up in addition to the normal MRI image using external high-frequency coil, for diagnosis of a lesion.

Besides the advantages of the fifteenth embodiment, extremely high-resolution MR imaging offers diagnosis of a lesion and determination and setting of treatment area in a even more accurate manner.

The thirteenth through fifteenth embodiments offer diagnosis and treatment systems which are constructed by combining the ultrasonic diagnosis and treatment system with X-ray CT and MRI devices the external image diagnosis device. Other alternative device such as an external ultrasonic diagnosis device may be combined.

In this case, the diagnosis and treatment system comprises the ultrasonic diagnosis device as the external image diagnosis device, and the ultrasonic diagnosis device is characterized by its external ultrasonic diagnosis probe.

In the above arrangement, ultrasonic diagnosis of a lesion using the ultrasonic probe inserted into the body cavity is supported by external ultrasonic diagnosis of the lesion. Display of internal and external ultrasonogram images is handled in the same way as in the previous embodiments.

Besides the same advantages described with reference to the previous embodiments, support by the external image diagnosis device is easily obtained since the ultrasonic diagnosis device as the external image diagnosis device is compact and easy to use.

In an ultrasonic probe having a relatively compact ultrasonic transducer such as the one disclosed in PCT WO93/16641, the compact ultrasonic transducer is driven by high power to give high-intensity focussed beam in ultrasonic thermotherapy.

The major portion of (input) power is lost or dissipated in heat because driving method is continuous driving (continuous wave) or intermittent driving (burst wave) and because conversion efficiency of ultrasonic transducer is inherently low. The ultrasonic probe suffers heat generation during ultrasonic thermotherapy (being irradiated with high-intensity, focussed ultrasonic beam). This problem may incur a heat damage on a living tissue with which the ultrasonic probe is put into contact.

Figure 51:
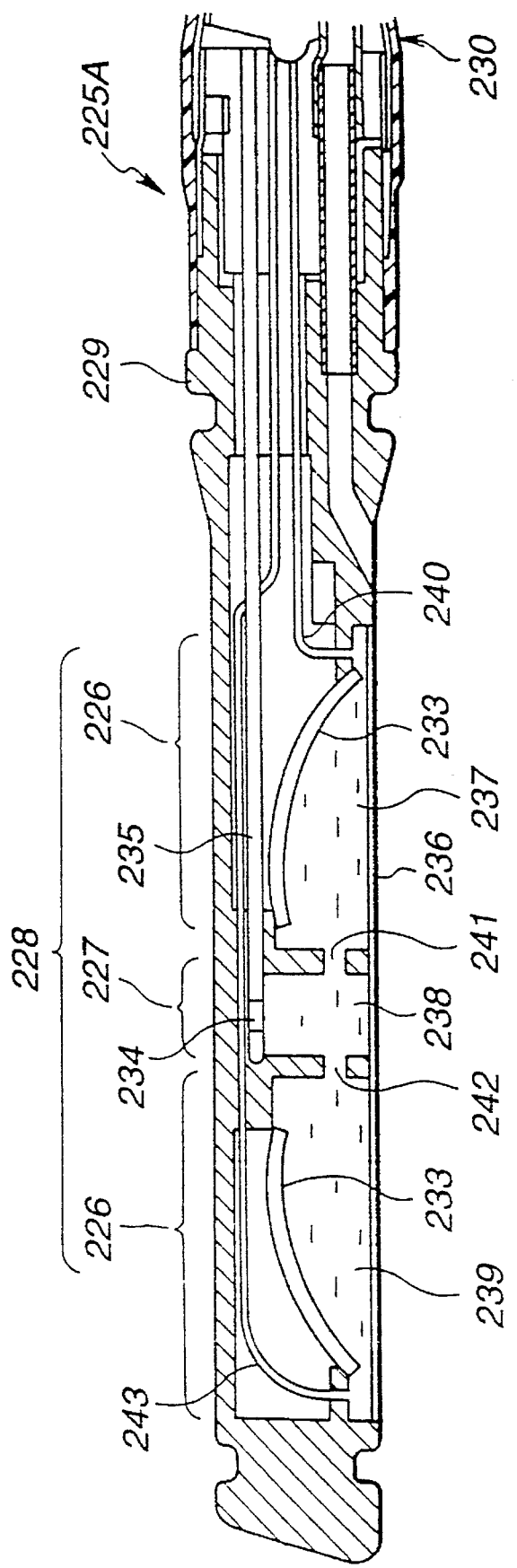
FIG. 51 is a cross-sectional view showing an arrangement of a distal-end part of an ultrasonic probe according to a sixteenth embodiment of the invention.

FIG. 51 is a cross-sectional view showing the construction of the end portion of the ultrasonic probe according to a sixteenth embodiment of the present invention, provided with means for resolving the above problem.

This embodiment is characterized in that cooling means for an ultrasonic treatment transducer is disposed in an ultrasonic diagnosis and treatment system having a small tube with a bendable portion that can be inserted into the body cavity.

In this embodiment, an ultrasonic probe 225 comprises an end portion 229 that includes an ultrasonic treatment and monitoring means 228 made of an ultrasonic treatment means 226 and an ultrasonic monitoring means 227. This embodiment is not limited to the ultrasonic probe.

A bendable portion 230 is disposed on the proximal side of the end portion 229.

The ultrasonic treatment means 226 contains ultrasonic treatment transducers 233, and the ultrasonic monitoring means 227 contains the end portion of a small-diameter ultrasonic monitoring probe 235 which acquires ultrasonogram image by causing the ultrasonic monitoring transducer 234 to mechanically scan.

To transmit ultrasonic wave emitted, an acoustic window 236 is disposed in the direction in which the ultrasonic treatment transducer 233 and the ultrasonic monitoring transducer 234 emit ultrasonic wave.

The acoustic window 236 constitutes part of the oute covering of the ultrasonic probe 225. Cooling water is introduced into spaces 237, 238, 239, formed between the acoustic window 236, the ultrasonic treatment transducer 233, and the end of the ultrasonic probe 235. The cooling water works as a transmission medium for ultrasonic wave.

The cooling water is supplied to the space 237 via a cooling water feeding piping 240 by an unshown cooling water supplier means in an ultrasonic diagnosis and treatment system main unit. Cooling water filled in the space 237 flows into the space 238 in the ultrasonic monitoring means 227 via a communicating passage 241, and into the space 239 via a communicating passage 242. Cooling water introduced into the space 239 is recovered out of the ultrasonic probe 225 via a cooling water recovery piping 243 by a cooling water recovery means in the ultrasonic diagnosis and treatment system main unit. The cooling means is a cooling water circulation means for the radiating face of the ultrasonic treatment transducer.

The operation of the sixteenth embodiment is now discussed.

In the above arrangement, acoustic medium in contact with the ultrasonic treatment transducer 233 is used as cooling water, and a circulation taking place in the course of feeding and recovering the cooling water during ultrasonic treatment is used to remove heat, caused by driving power loss in the treatment ultrasonic transducer 233, from the radiating face of the ultrasonic treatment transducer 233, in order to prevent the ultrasonic treatment transducer from rising to a high temperature When a compact ultrasonic treatment transducer is driven by high power to output a high-intensity, focused ultrasonic beam, heat generation takes place.

According to the present embodiment, however, both the ultrasonic transducer and the end portion of the ultrasonic probe are prevented from rising to a high temperature due to driving power loss, and thus a living organ is protected from heat damage.

Since cooling water is in contact with the ultrasonic treatment transducer on its radiating face only, no impedance rising takes place in the transducer, and cooling of the transducer only is possible. This offers the advantage that no load rise in the transducer arising circulation of cooling water takes place. Thus, the ultrasonic treatment transducer is free from subsequent driving voltage rise as a result of load rise.

Figure 52:
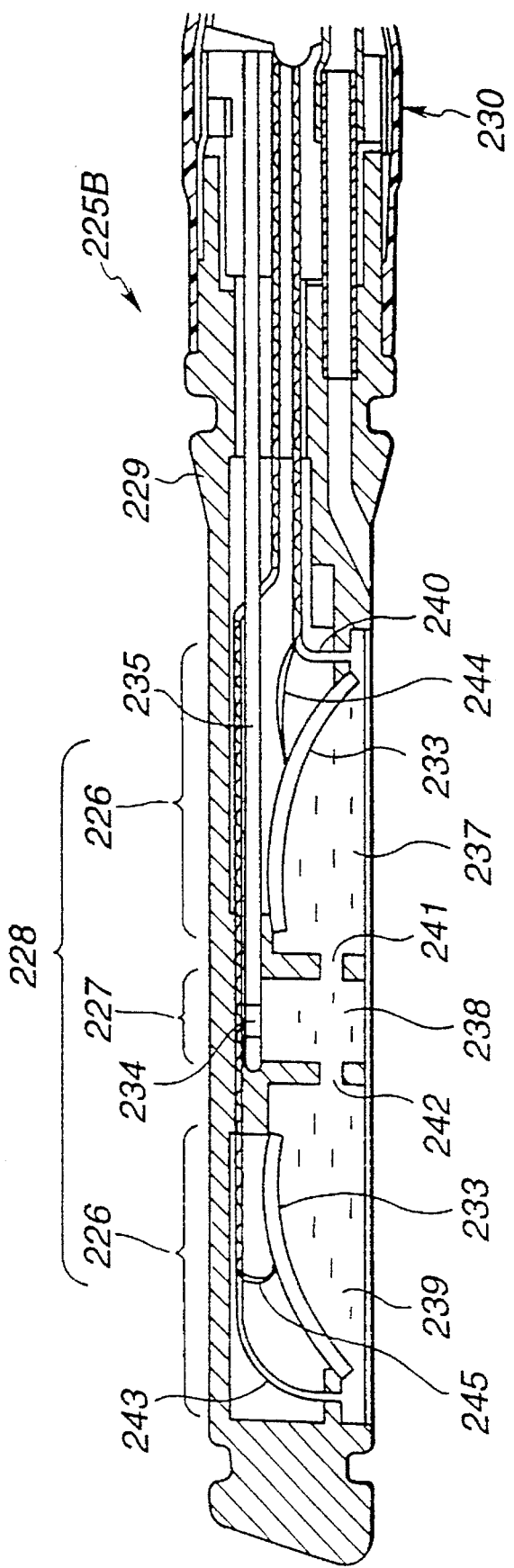
FIG. 52 is a cross-sectional view showing an arrangement of a distal-end part of an ultrasonic probe according to a seventeenth embodiment of the invention.

A seveteenth embodiment of the ultrasonic probe 225B in FIG. 52 is a modified version of the sixteenth embodiment of the ultrasonic probe 225, wherein the ultrasonic probe 225B offers a monitoring capability of temperature in the ultrasonic treatment transducer 233. Thus, the ultrasonic treatment transducer 233 is associated with temperature monitori means.

Disposed on the back face of the ultrasonic treatment transducer 133, namely the face playing no role in ultrasonic emission, are temperature sensor 244, 245 made of thermocouples or the like (junction portion in case of thermocouple). Leads of the thermocouples 244, 245 are respectively disposed on the cooling water feeding piping 240 and the cooling water recovery piping 243, and connected to unshown temperature monitoring means in the ultrasonic diagnosis and treatment system main unit. The temperature monitoring means presents detected temperature of the ultrasonic treatment transducer 233, and gives an alarm in response to unsafe temperature, leading to a shutdown of treatment.

In this embodiment, the temperature of the ultrasonic treatment transducer 233 is directly monitored, and thus from the detected temperature, the ultrasonic treatment system main unit determines whether the cooling water is present or absent and controls cooling water circulation speed.

The ultrasonic treatment transducer is thus effectively cooled.

Figure 53:
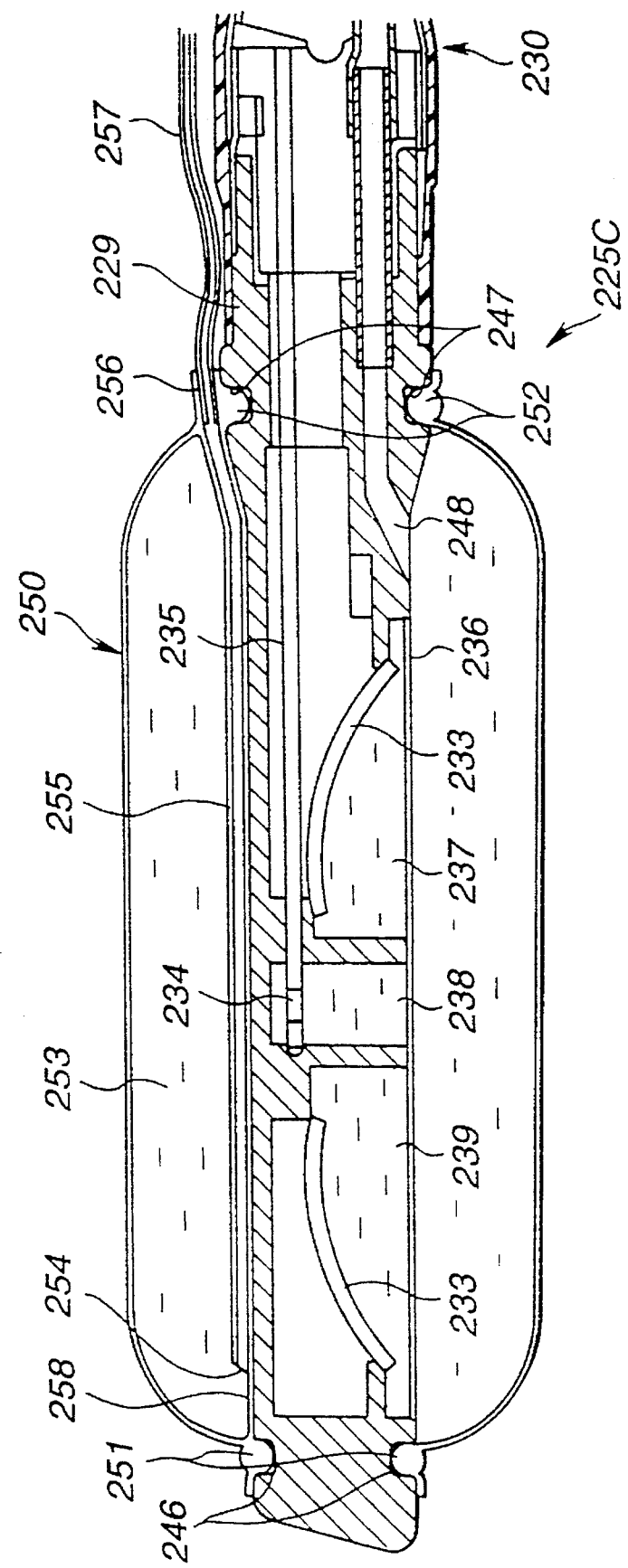
FIG. 53 and FIG. 54 relate to an eighteenth embodiment of the invention, FIG. 53 being a cross-sectional view showing an arrangement of a distal-end part of an ultrasonic probe in the eighteenth embodiment.

FIG. 53 shows the end portion 229 of the ultrasonic probe 225C according to a eighteenth embodiment of the ultrasonic diagnosis and treatment system wherein the cooling means is constructed of an expandable and shrinkable bag-like member cooling water circulation means that covers the ultrasonic treatment means 226 having the ultrasonic treatment transducer 233 therein The bag-like member is a balloon 250, and the balloon 250 closely encloses the outline of the ultrasonic treatment means 226. The balloon 250 is provided with O-ring portions 251, 252 which are engaged with mating grooves 246, 247 formed on the cover of the ultrasonic probe 225C in order to keep watertightness of the interior of the balloon. The balloon 250 is also provided with a suction passage 255, and a support joist 258 is disposed between the balloon end and the opening 254 of the suction passage in order to form and keep open the suction passage 255 and in order to support the suction passage 255 up to the end of the balloon.

The suction passage 255 of the balloon 250 is connected to a tube 257 via a piping junction portion 256 so that cooling water is circulated back out of the ultrasonic probe 225C by an unshown cooling water recovery means in the ultrasonic diagnosis and treatment system main unit.

The ultrasonic probe 225C is provided with a feeding passage 248 for cooling water that also works as acoustic medium, and the feeding passage 248 is open to the interior space 253 of the balloon 250. The cooling water is supplied to the interior space 253 via the cooling water feeding passage 248 by an unshown cooling water supplier means in the ultrasonic diagnosis and treatment system main unit.

On the other hand, inside the ultrasonic probe 225C, spaces 237, 238, and 239 formed between the ultrasonic treatment transducer 233, the end portion of the ultrasonic monitoring probe 235 and the acoustic window 236 are beforehand filled with acoustic medium.

In the above arrangement, the cooling water supplier means in the ultrasonic diagnosis and treatment system main unit supplies cooling water into the balloon 250 via the cooling water feeding passage, causing the balloon 250 to expand.

When the balloon 250 is filled with cooling water and expands to a desired size, the cooling water recovery means in the ultrasonic diagnosis and treatment system main unit sucks up and recovers cooling water at the same flow rate as that for feeding via the suction passage 255 and the tube 257.

Cooling water fills the balloon 250 to perform acoustic coupling to a living tissue, as acoustic medium, while circulating in the balloon 250.

Figure 54:
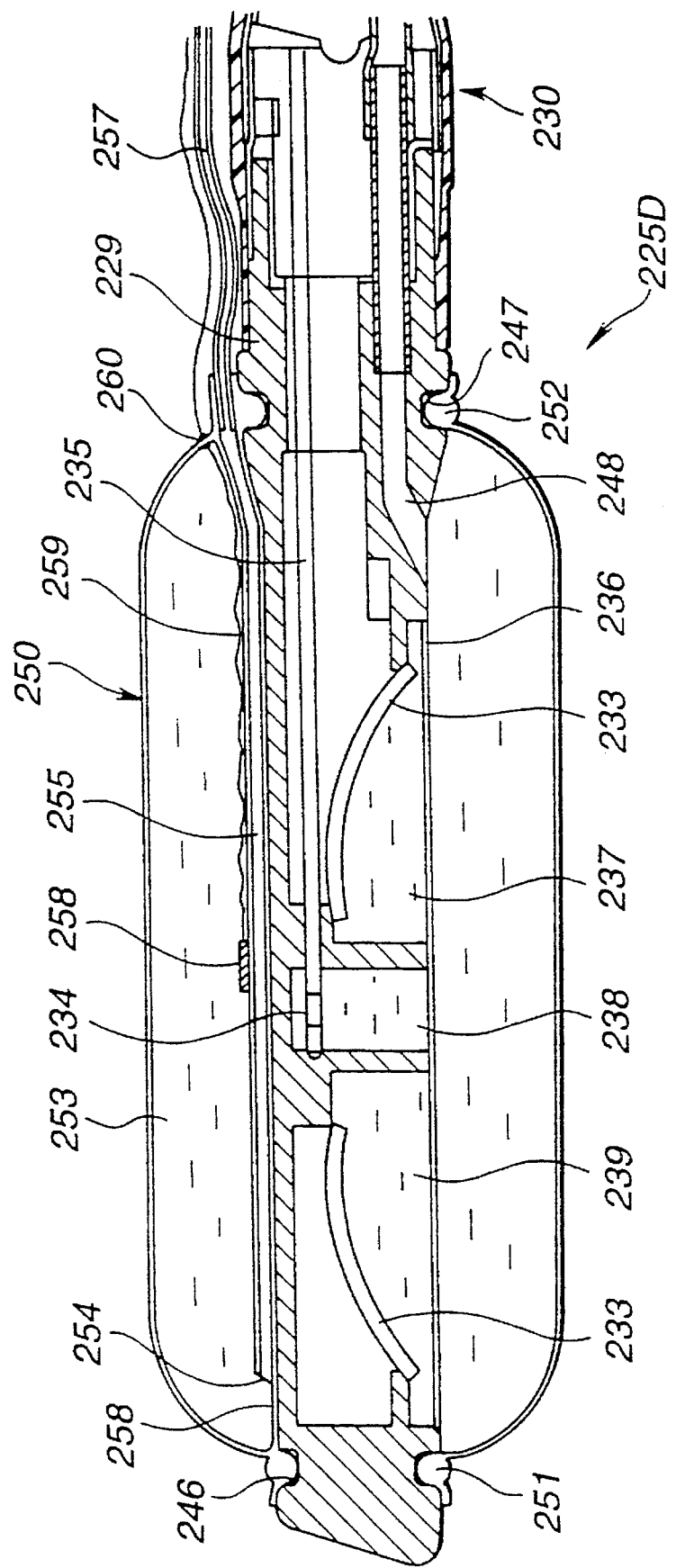

Circulation of cooling water in the balloon 250 may be made under flow rate control. As in an ultrasonic probe 225D according to an alternate example of the twelfth embodiment, shown in FIG. 54, a pressure sensor 258 may be provided in the balloon 250 in order to circulate cooling water under pressure control by an unshown balloon inner pressure/control means in the ultrasonic diagnosis and treatment system main unit.

The bag-like member cooling water circulation means may thus be provided with the pressure sensor inside the bag-like member to perform pressure control based on detected pressure in the bag-like member, and operates the same way.

The embodiment and its alternate example offer the advantage that heat damage to living tissue is prevented by cooling the outer surface of the ultrasonic probe with cooling water by circulating at a constant flow rate or constantly through inside the balloon, cooling water which at the same time performs acoustic coupling between the ultrasonic probe 225C and the living tissue.

When cooling water is circulated at a constant pressure, it is possible to adjust a stand-off clearance at will when the ultrasonic probe 225D is being put into contact with living tissue, while keeping the ultrasonic probe 225D cooled.

As an alternate example of the eighteenth embodiment, a temperature sensor may replace the pressure sensor 258 to detect temperature of the cooling water inside the balloon 250. Like the seventeenth embodiment, circulation control and treatment control may be performed. Such arrangement offers the same advantages and operation as the seventeenth embodiment.

Alternatively, a temperature/pressure sensor may replace the pressure sensor 258 to achieve the combined advantages and operation of the seventeenth and eighteenth embodiments.

Figure 55A:
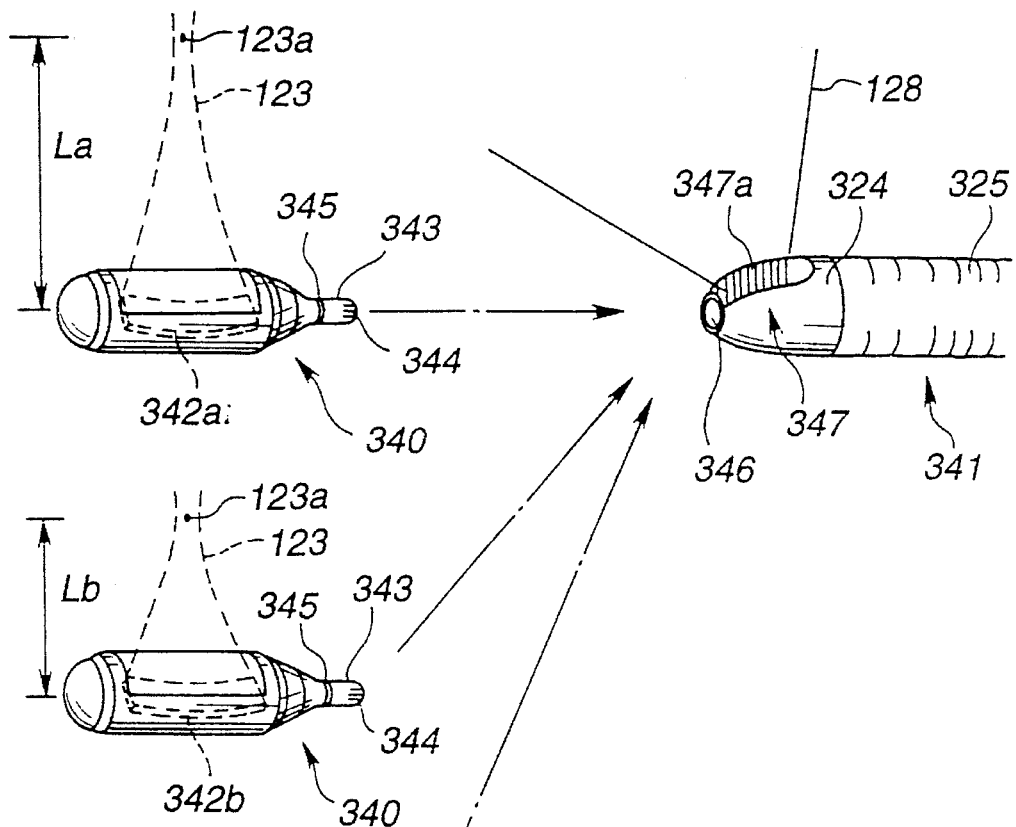

Discussed next is a ninteenth embodiment. As shown in FIG. 55A, the ultrasonic treatment means 240 has three ultrasonic treatment means 342a, 342b, and 342c available, having focal lengths La, Lb, and Lc (La>Lb>Lc), respectively. They are detachably mounted onto the ultrasonic probe main unit 341.

Figure 55B:
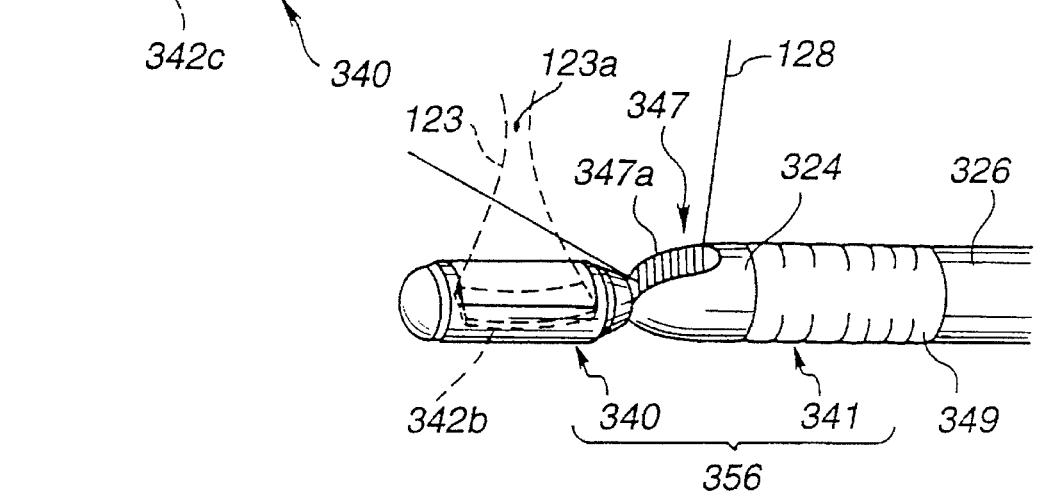
FIG. 55B is a perspective view showing an arrangement on the side of the distal end of the ultrasonic probe under a state in which ultrasonic therapy means is mounted.

FIG. 55B shows the ultrasonic treatment means 340 in which the ultrasonic treatment means 342b having a focal length Lb is mounted.

Each ultrasonic treatment means 340 has on its end a connector 343. The connector 343 is provided with an O-ring 345 to keep air-tight and terminals 344 for conducting driving signals for the ultrasonic treatment transducer 342i (i=a, b, c).

The ultrasonic probe main unit 341 is provided with a socket 346 which receives the connector. Disposed on the proximal side of the socket 346 is the end portion 324 having, for example, a convex-arra transducer 347a, of the ultrasonic monitoring means 347. Disposed on the proximal side of the ultrasonic monitoring means 347 is the bendable portion 325.

The rigid insert tube portion 326 is disposed on the proximal side of the bendable portion 325.

By detachably mounting the ultrasonic treatment means 340 in this emvodiment, three ultrasonic treatment transducers 342a, 342b, and 342c having different focal lengths may be selectively used.

This flexibility helps increase the depth range for treatment.

Figure 56A:
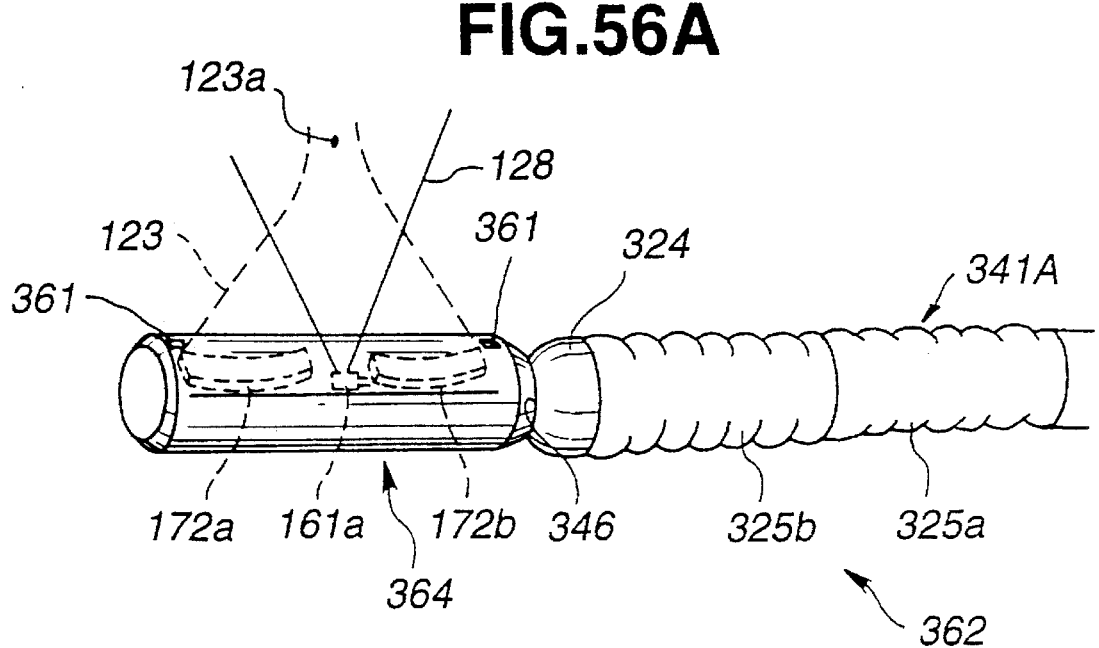
FIG. 56A is a perspective view showing an arrangement on the side of a distal end of an ultrasonic probe in a modification.

FIG. 56A shows the end portion of the ultrasonic probe 362 of thealternate alternate example of ninteen embodiment.

The end portion of the ultrasonic probe 362 is provided with the ultrasonic treatment and monitoring means 364. Tactile sensor 361 is mounted on the surface of the ultrasonic treatment and monitoring means 364. Disposed on the proximal side of the ultrasonic treatment and monitoring means 364 are two bendable curved portions 325a, 325b axially connected.

The ultrasonic treatment and monitoring means 364 is almost identical to the ninth embodiment in construction, and difference is that the ultrasonic treatment and monitoring means 364 is detachably mounted to the probe main unit 341A in this embodiment As shown in FIG. 56A, a connector socket 346 disposed on the end portion 324 of the probe main body 341A is mated with the connector 343 of the ultrasonic treatment and monitoring means 364 (see FIG. 55A, for example).

Figure 56B:
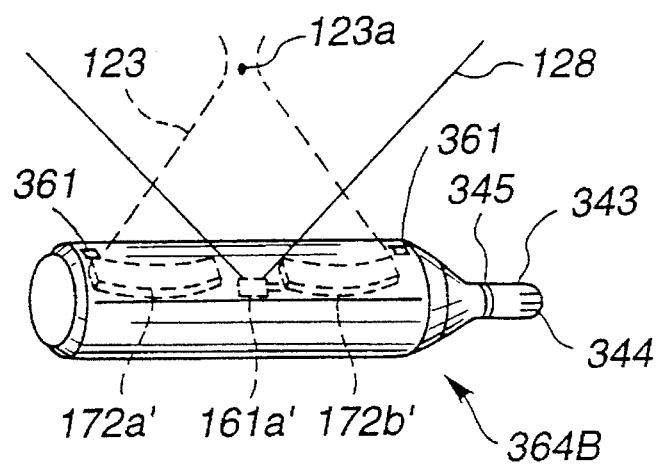
FIG. 56B is a view showing ultrasonic therapy means which is detachable with respect to the ultrasonic probe.
Figure 56C:
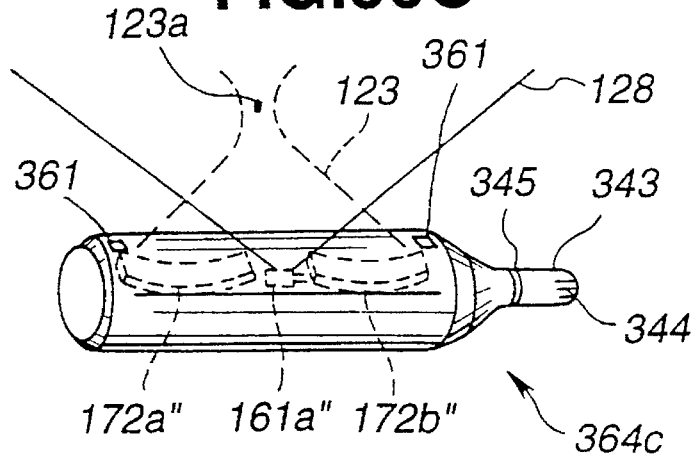
FIG. 56C is a view showing ultrasonic therapy means which is different in focal distance from that shown in FIG. 56B.

The ultrasonic treatment and monitoring means 364 in FIG. 56A may be replaced with the ultrasonic treatment and monitoring means 364A in FIG. 56B, or may be replaced with the ultrasonic treatment and monitoring means 364B in FIG. 56C. The ultrasonic treatment and monitoring means 364A in FIG. 56B uses ultrasonic treatment transducers 172a', 172b' having a focal length different (for example, shorter than) from that of the transducers 172a, 172b employed in the ultrasonic treatment and monitoring means 364 in FIG. 56A.

The ultrasonic treatment and monitoring means 364C in FIG. 56C uses ultrasonic treatment transducers 172a", 172b" having a focal length even shorter than that of the transducers 172a, 172b employed in the ultrasonic treatment and monitoring means 364A.

The ultrasonic treatment and monitoring means 364A in FIG. 56B uses the ultrasonic monitoring transducer 161a' having a monitoring coverage 128 different from (for example, wider than) that of the ultrasonic monitoring transducer 161a in the ultrasoni treatment and monitoring means 364 in FIG. 56A. The ultrasonic treatment and monitoring means 364B in FIG. 56C uses the ultrasonic monitoring transducer 161a" having a monitoring coverage wider than that of the ultrasonic monitoring transducer 61a' in the ultrasonic treatment and monitoring means 364A in FIG. 56B. Furthermore, as the ultrasonic monitoring transducer 161a, an ultrasonic monitoring transducer with a different driving frequency may be used.

Since a plurality of curved portions are used in the ultrasonic probe in this alternate, the end portion may be flexibly put in contact with a complicatedly configured organ. The monitoring means and treatment means may be arranged in the curved portions, resulting in a compact probe design. The monitoring means and the treatment means may be designed as disposable (expendable).

By detachably mounting the ultrasonic treatment and monitoring means 364, depth of treatment region is set variably. Furthermore, optimum diagnosis is achieved by changing driving frequency of the monitoring means depending on depth, for example, using a higher frequency in shallow area imaging to increase resolution, or using a lower frequency in deep area imaging to increase detection range further.

Figure 57A:
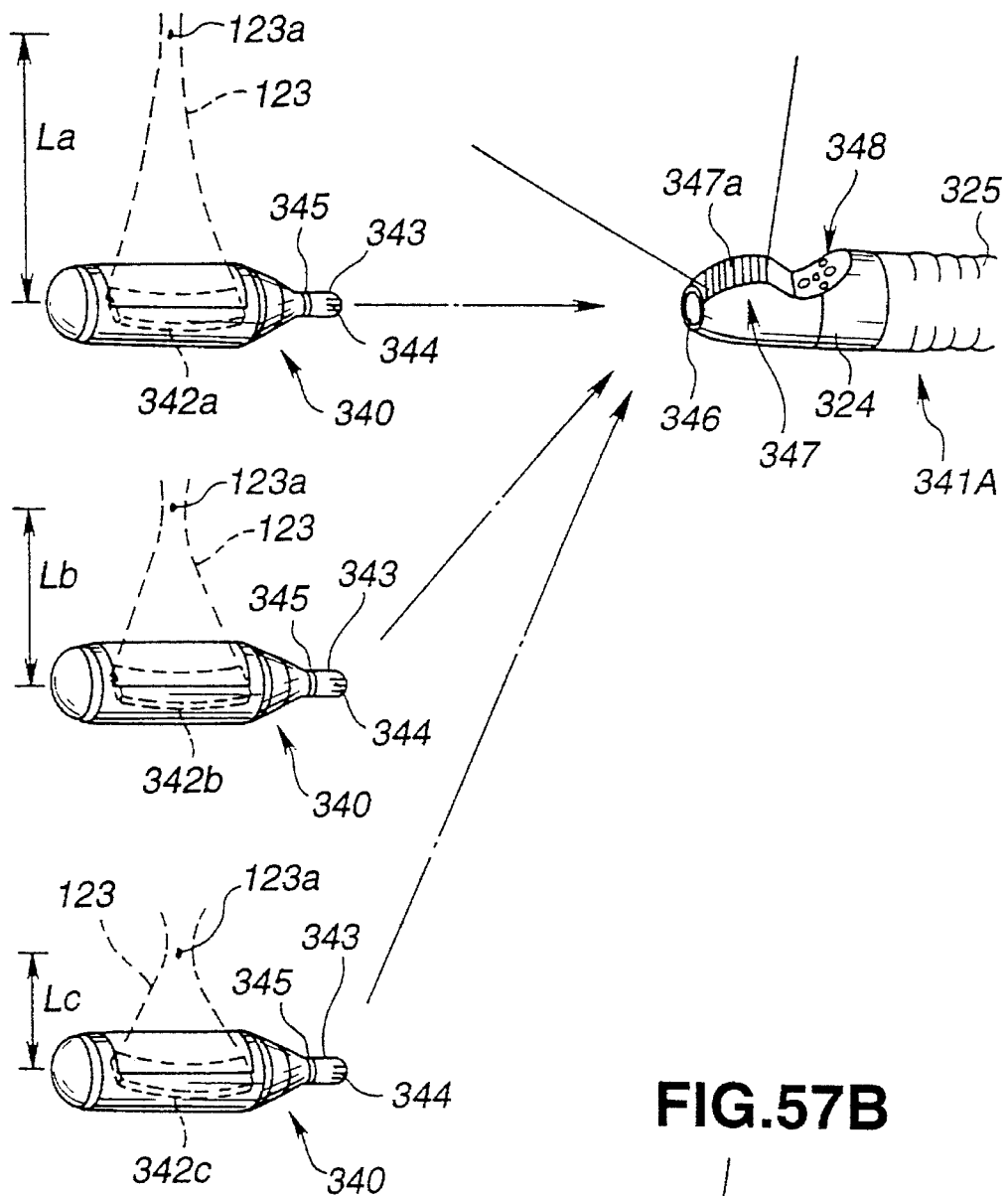
FIG. 57A is a perspective view showing an arrangement of an ultrasonic probe in another modification, with ultrasonic therapy means demounted.
Figure 57B:
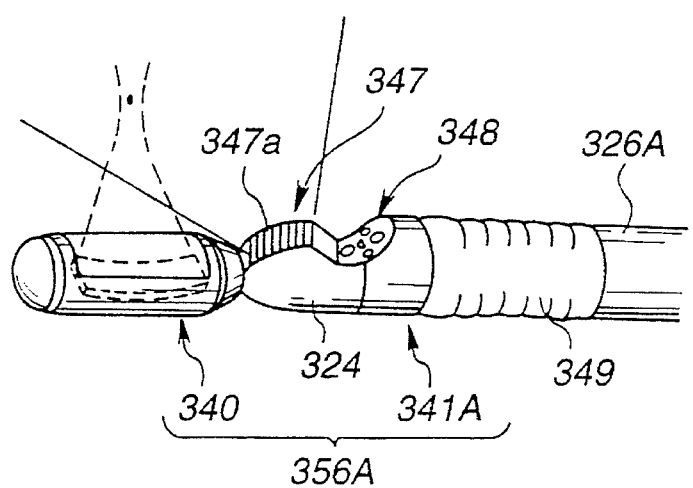

FIG. 57A and FIG. 57B shows an alternate example of the ninteenth embodiment of the present invention.

The ultrasonic probe 356A according to the present alternate comprises the ultrasonic probe 341A that includes an optical monitoring means 348 disposed on the end portion 324 of the ultrasonic probe main unit 341 in FIG. 55A. Furthermore, a soft insert tube 326A replaces the rigid insert tube 326 on the proximal side of the curved portion 325. In its assembled state, the ultrasonic probe 356A is essentially identical to the seventh embodiment in construction.

As in FIG. 57A, the ultrasonic treatment means 340 has three ultrasonic treatment means 342a, 342b, and 342c available, having focal lengths La, Lb, and Lc, respectively. They are detachably mounted onto the ultrasonic probe main unit 341A. Their construction has been discussed, and no further explanation is given here.

This alternate example offers the same advantages and operation as those for the seventh embodiment.

Furthermore, as already described previously, depending on the depth of treatment area, the ultrasonic treatment means 340 with the ultrasonic treatment transducer having a focal length equal to the depth may be used. Thus, an increased treatment depth range results, permitting a more appropriate treatment (for example, a treatment session is complete in a shorter time or necrotization of tissue other than a lesion is minimized).

Next a twentieth embodiment of the present invention is explained. As shown in FIG. 58, the ultrasonic diagnosis and therapy system 401 comprises, for instance, an ultrasonic probe 402 configured like an electronic endoscope, a light source 403 to supply the lighting for the probe 402, a camera control unit (CCU) 404 to process signals for an image pick-up means built in the probe 402, an ultrasonic diagnosis and therapy circuit 405 in which a signal processing system 405A for generating an ultrasonic image and a therapeutic signal generating system 405B for generating signals for therapy are both built, and a color monitor 406 which displays an endoscopic image and an ultrasonic image from video signals of the processing system (not shown) of CCU 404 and the ultrasonic signal processing system 405A.

Figure 59:
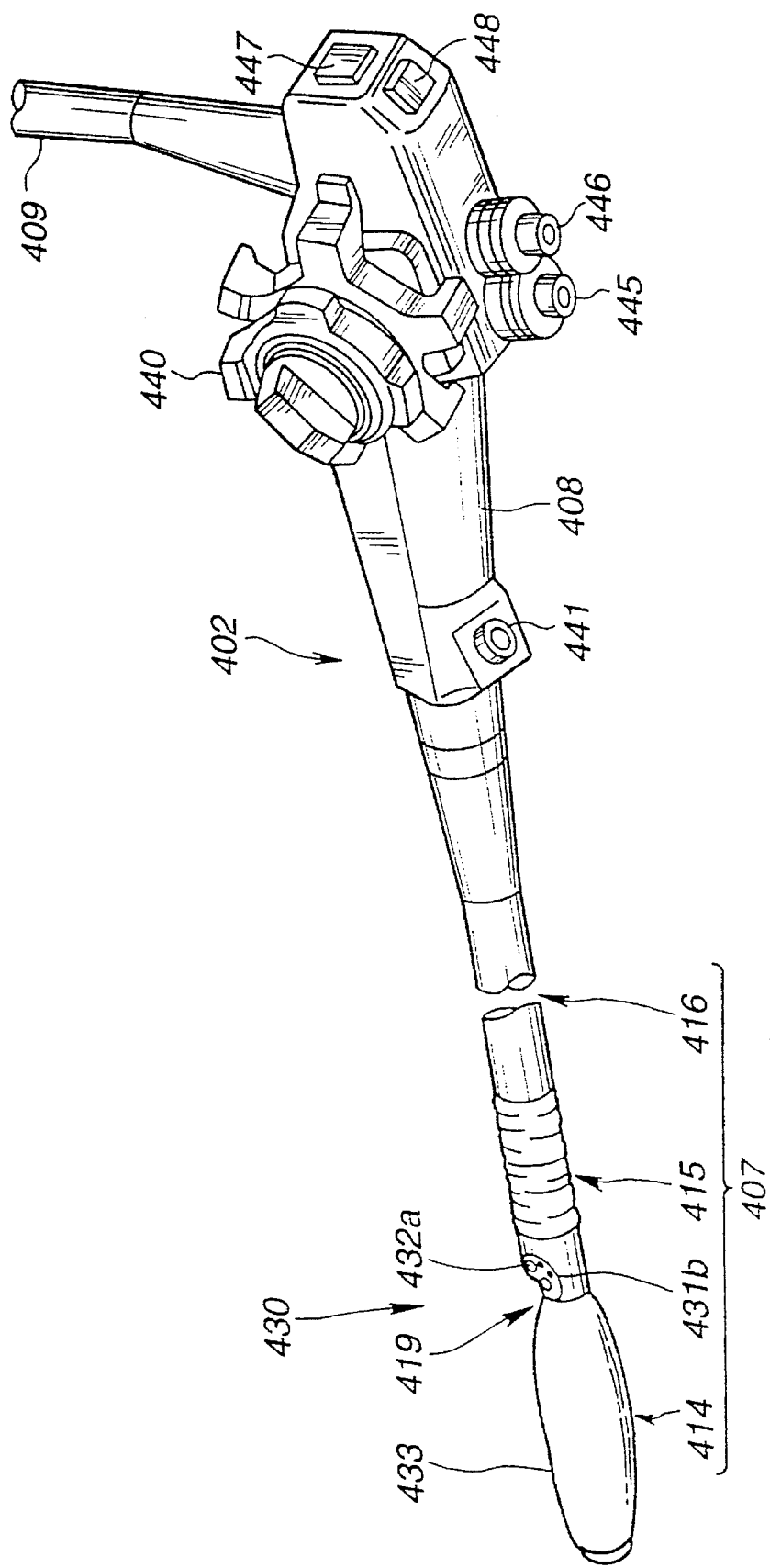

As shown in FIGS. 58 and 59, the ultrasonic probe 402 configured like said electronic endoscope has an insertion part 407 shaped in a small tube so as to be inserted into celom, and an operation part 408 which is provided at the rear end of the insertion part 407 and an operator grip for operation, and an universal cable 409 extended from the operation part 408. The cable 409 can be removably connected to the light source 403 through a light source connecter 410 provided at the end of the cable 409.

A signal connecter 412a at the one end of a signal cable 411 is connected to this connecter 410, while CCU connecter 412b connected to CCU 404, and an ultrasonic connecter 412c connected to the ultrasonic diagnosis and therapy circuit 405, are provided at the other end of the cable 411.

The insertion part 407 is successively formed in turn from the tip end, of a hard end portion 414, a bendable part 415 which is freely bent, and a flexible part 416 with flexibility. An ultrasonic therapy means 417, an ultrasonic observation means 418, a treatment function guide part 419, an optical observation means 430, and an ultrasonic focused point adjustment means 433, which will be described hereinafter, are arranged at the end portion 414.

The optical observation means 430 is formed of an illumination light emission means for emitting an illumination light through a light guide 431a and the lens 431b of an illumination window, and an image pick-up means having an object lens 432a for forming an optical image of the side view of an target organ illuminated by the light, and CCD 432b arranged at the focus plane of the lens 432a.

The light guide 431a can be connected to the light source 403 through into the insertion part, through the light source connecter 410, and the illumination light generated by a lamp 434 is focused on the rear end plane of the light guide 431a by the lens, and then transmitted to the end portion side, so as to illuminate the forward oblique direction passing through into an illumination lens 431b.

A range illuminated by the light emitted in the forward oblique direction is approximately met with the observation range by the lens 432a, such that a subject image of the observation region illuminated by the light is formed onto the image pick-up face of CCD 432b. The electric signals of the subject formed at CCD 432b are transmitted to a video signal processing system in CCU 404 through a signal line 436, and converted into video signals, and then displayed on the color monitor 406 as an endoscopic image 437 though a super impose circuit 429.

Figure 60:
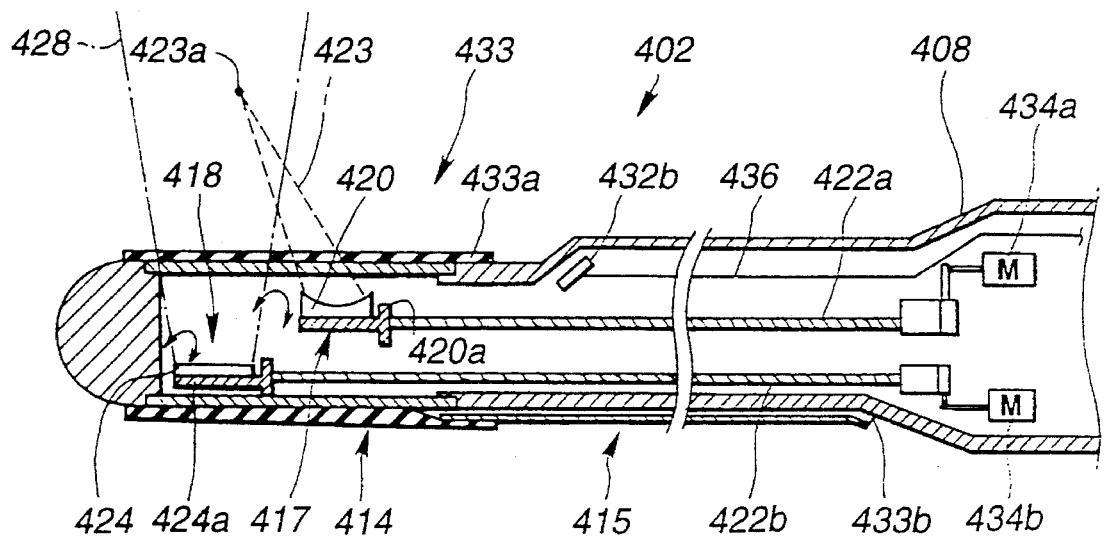

As shown in FIG. 60, an ultrasonic therapy means 417 for making the ultrasonic high-temperature therapy by irradiating ultrasonic waves at a part to be treated is, for example, a mechanical scanning type therapeutic ultrasonic transducer 420, wherein a concavity shaped in circular arc is formed in the insertion axial direction, one end of which is connected to a first flexible shaft 422a, and fixed integrally on a fixed member 420a which can be freely rotatable perpendicular to the insertion axial direction.

Rotational force by a motor 434a provided in the operation part 408 is transmitted to the first flexible shaft 422a, whereby the therapeutic transducer 420 is rotated perpendicular to the insertion axial direction. Drive signals are applied by a drive voltage generator 422 provided in the ultrasonic diagnosis and therapy circuit 405 connected to a lead line 421 passing through into the insertion part shown in FIG. 58, whereby ultrasonic waves are formed in therapeutic ultrasonic beam shown in a dashed line (FIG. 60) with directivity and irradiated from the concavity within the irradiation range 423, and focused on the focal point 423a at a determined distance.

The therapeutic ultrasonic waves irradiated from the transducer become an ultrasonic beam with extremely high intensity at the focal point 423a, namely has a high energy density acoustically.

Therefore, the drive signals are applied to the transducer 420 to irradiate acoustic energy at a high density onto, for example, a lesion tissue such as a tumor positioned adjacent to the focal point 423a, whereby the tissue can be cauterized for therapy.

The transducer 420 can be freely rotated perpendicular to the insertion axial direction, so the irradiation face of the transducer 420 can be easily provided against the region to be treated by rotating the transducer in such direction, thus, such configuration also functions as an ultrasonic focused point adjustment means which will be described later.

An ultrasonic observation means 418 for obtaining a ultrasonic image is, for example, a mechanical radial scanning type observatory ultrasonic transducer 424, wherein it is shaped in flat plate, one end of which is connected to a second flexible shaft 422b, and fixed integrally on a fixed member 420a which can be freely rotatable perpendicular to the insertion axial direction.

Rotational force by a motor 434b provided in the operation part 408 is transmitted to the second flexible shaft 22b, whereby the transducer 424 is rotated perpendicular to the insertion axial direction. The transducer 424 is connected to the signal processing system 405A having a transmit pulse generation circuit 426 and a receive processing circuit 427 through a lead line 424 passing through into insertion part shown in FIG. 58, and the transmit pulses of the generation circuit 426 are applied, whereby ultrasonic waves are transmitted to a target tissue side in a radial ultrasonic observation region 428 as shown in a dashed line in the drawing.

Then the ultrasonic waves reflected from the tissue side are received by the transducer 424 again, and converted into electric signals, then signal-processed by the receive processing circuit 427, and converted into video signals corresponding to an ultrasonic image, then input into the color monitor 406 through the super impose circuit 429, and an endoscopic image 437 and an ultrasonic sectional image 437' are displayed together.

A balloon 433a is provided at the outer circumference of the end portion 414 of the probe 402 in which said transducer 424 and 420 are arranged, and functions as an ultrasonic focused point adjustment means 433 for controlling the ultrasonic focused distance from a therapeutic ultrasonic transducer 420 to a therapeutic target region, such that ultrasonic waves irradiated from the transducer 420 can be irradiated to the therapeutic target region at a high energy density. The balloon 433a is expandable by injecting acoustic transmission medium such as a gelable liquid thereinto from an injection port provided on this side.

A bendable part 415 is formed of a plurality of bendable pieces rotatably connected each other in succession, and one end of the bendable part 415 is fixed at the end portion 414, and the other end is fixed at the flexible part 416. An angle wire 439 connected to a pulley 438 in the operation part is pulled or relaxed by adjustably rotating an angle knob 440, whereby the bendable part 415 can be bent in directions to which the wire 439 is pulled, namely in 404 directions; up, down, right and left, or in two directions; up-down or right-left. In this manner, the bendable part 415 is configured nearly in the same way as a bendable part used for a conventional endoscope.

An introductory port 441 for introducing a treatment tool such as a clamp is provided adjacent to the tip part of said operation part 408, and this port 441 is in communication with a treatment tool channel 442 provided in the insertion part, so the opening of the treatment function guide part 419 provided at the end portion 414 can be a clamp exit 442a. The clamp exit 442a is provided such that the opening comes to a position adjacent to an optical observation means 430, whereby the state of treatment made by, fore example, the treatment tool extruded from the exit 442a, can be easily observed when treatment for organ is made with the tool extruded from the exit 442a, In addition, an air/water supply button denoted with reference numeral 445, and a suction button 446 provided adjacent to the supply button 445, and image control .buttons (or image control switches) 447, 448 for freezing or switching the endoscopic image by the image pick-up means of the optical observation means 430, all of which are provided at the operation part 408.

Signals output from these image control buttons 447, 448 are input into CCU 404 and a controller 449.

The controller 449 is connected to a key board 450 and a foot switch 451, so the setting time for irradiation from the ultrasonic therapy means 417 and the clinical information of patients can be input by the key board 450. The therapy means 417 can be controlled for the start and stop by the foot switch 451.

The controller 449 is connected to the transmit circuit 426 in the ultrasonic diagnosis and therapy circuit 405, so all conditions for the ultrasonic transmission of the ultrasonic observation image, the signal processing for received signals, and the output of ultrasonic therapy can be changed, respectively.

In addition, the controller 449 is connected to CCU 404, so CCU 404 can be controlled by the keyboard 450.

The operation of the ultrasonic diagnosis and therapy system 401 configured as above will be described.

Figure 61:
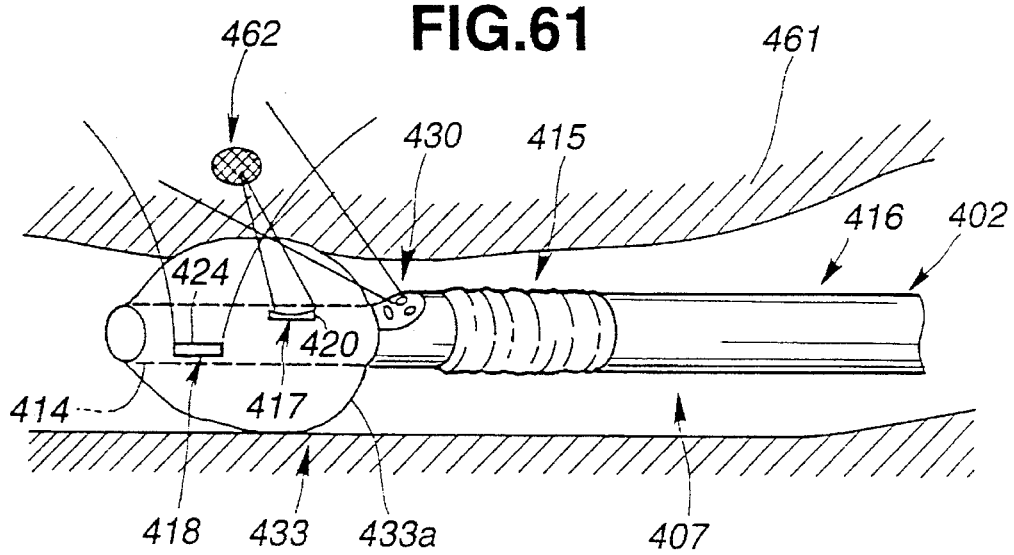

As shown in FIG. 61, the insertion part 415 of the ultrasonic probe 402 is inserted into, for example, a luminal organ 461 such as an esophagus. The bendable part 415 provided at the insertion part 415 is then manipulated to be positioned adjacent to the treatment region 462 for therapy based on an optical image by the optical observation means 430 and an ultrasonic diagnostic image by the ultrasonic observation means 418.

Then, the observatory ultrasonic transducer 424 is rotated for radial scanning by the motor 434b, namely a positioning control perpendicular to the insertion axial direction is made, and while an ultrasonic image of the region 462 is displayed on the monitor 406, the therapeutic ultrasonic transducer 420 is rotated by a required variant by the motor 434a, namely the positioning control for the irradiation face of the therapeutic transducer 420 is made perpendicular to the insertion axial direction.

Gelable liquid is injected from the injection port 433b into the balloon 433a arranged onto the outer circumference of the tip part arranged adjacent to a lesion in the luminal organ, and the balloon 433a is gradually expanded until a position of the region 462 in the depth direction from the irradiation face of the transducer 420 is a focused point of the therapeutic ultrasonic waves. Thus, the positioning adjustment for the ultrasonic focused point of the transducer 420 is made by the region 462.

After output conditions for the ultrasonic waves irradiated onto the treatment region 462 are checked by the controller 449 and key board 450, the therapeutic ultrasonic waves are irradiated from the transducer 420 toward onto the region by means of the foot switch 451, while the endoscopic image 437 and ultrasonic image 437' on the monitor 406 are observed.

Then The therapeutic ultrasonic waves at a high energy density are focused on the region 462 in position of the focused point and the region 462 is cauterized by the drastic increase in temperature. The therapeutic ultrasonic waves are irradiated onto the region 462, while observing the state of protein degeneration in the tissue by the cauterization on the ultrasonic diagnostic image 433, until the degeneration progresses up to the point required to cause the local death of the lesion cells.

After that, the irradiation are interrupted by means of the foot switch 451, and the achievement of the therapy is checked on the diagnostic laminagraphic image 437', and additional irradiation is continued if necessary, and then the achievement of the therapy is checked again, and the therapy is completed if it is enough.

In this manner, the ultrasonic waves at a high energy density are irradiated onto the treatment region to achieve the required therapy, wherein an mechanical radial scanning type therapeutic ultrasonic transducer which functions as the ultrasonic focused point adjustment means and is freely rotated perpendicular to the insertion axial direction is used, and the end portion provided with an ultrasonic therapy means is covered with a balloon as the adjustment means, and then an ultrasonic therapeutic transducer is rotated perpendicular to the insertion axial direction to provide the irradiation face of the transducer against the region, and the focused point of the transducer and the depth direction of the region are met with the adjustment of the balloon in diameter.

An mechanical scanning type observatory ultrasonic transducer and a therapeutic ultrasonic transducer can be integrally fixed at a single fixed member by means of adhesion and used for mechanical radial scanning, and one single observatory and therapeutic ultrasonic transducer having both functions of observation and therapy can be provided instead of employing two observatory ultrasonic transducer and therapeutic ultrasonic transducer separately provided at the ultrasonic probe, whereby the overall dimension of the probe can be small in diameter with only one fixed member used.

Figure 62:
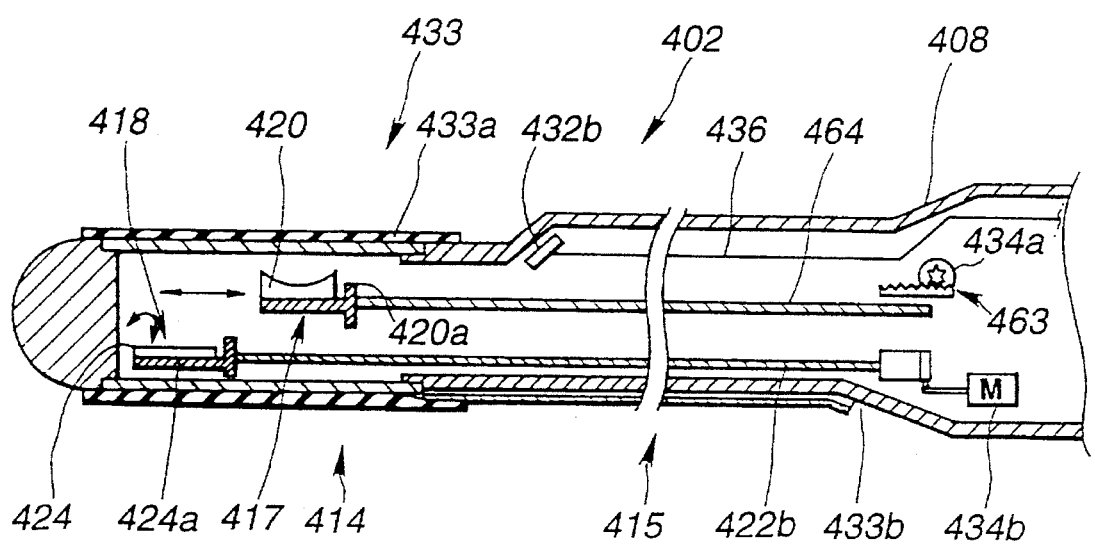
FIG. 62 is a cross-sectional view showing a schematic arrangement of an ultrasonic probe according to a twenty-first embodiment of the invention.

FIG. 62 is a sectional view showing a schematic structure of an ultrasonic probe according to the twenty-first embodiment of the invention.

In this embodiment as shown in the drawing, the ultrasonic therapy means of the ultrasonic probe 402 is configured such that rotational force by the motor 434a is transmitted to a shaft 464 through a rack-pinion mechanism 463 and the ultrasonic therapy transducer 420 is linearly moved for mechanical linear scanning, and then positioning control is made for the irradiation face of the transducer 420 to be provided against the treatment region, instead of the arrangement of the mechanical radial scanning type therapeutic ultrasonic transducer freely rotatable perpendicular to the insertion axial direction. The other configuration is similar to of the twentieth embodiment, and like reference characters denote like parts in the first embodiment, and the description will be omitted.

As shown in the twentieth embodiment of FIG. 61, the insertion part 415 of the probe 402 is inserted into, for example, a luminal organ 461 such as an esophagus. The end portion 414 is then manipulated to be positioned adjacent to the treatment region 462 for therapy based on an optical image by the optical observation means 430 and an ultrasonic diagnostic image by the ultrasonic observation means 418. Then, the operation part 408 of the probe 402 is twistedly manipulated to make a positioning control perpendicular to the insertion axial direction, and while the treatment region 462 is displayed on the monitor 406, the therapeutic ultrasonic transducer 420 is axially moved by the motor 434a, thus the irradiation face of the therapeutic transducer 420 is provided against the region 462. Other operations and advantages will be the same as of said twentieth embodiment.

Figure 63:
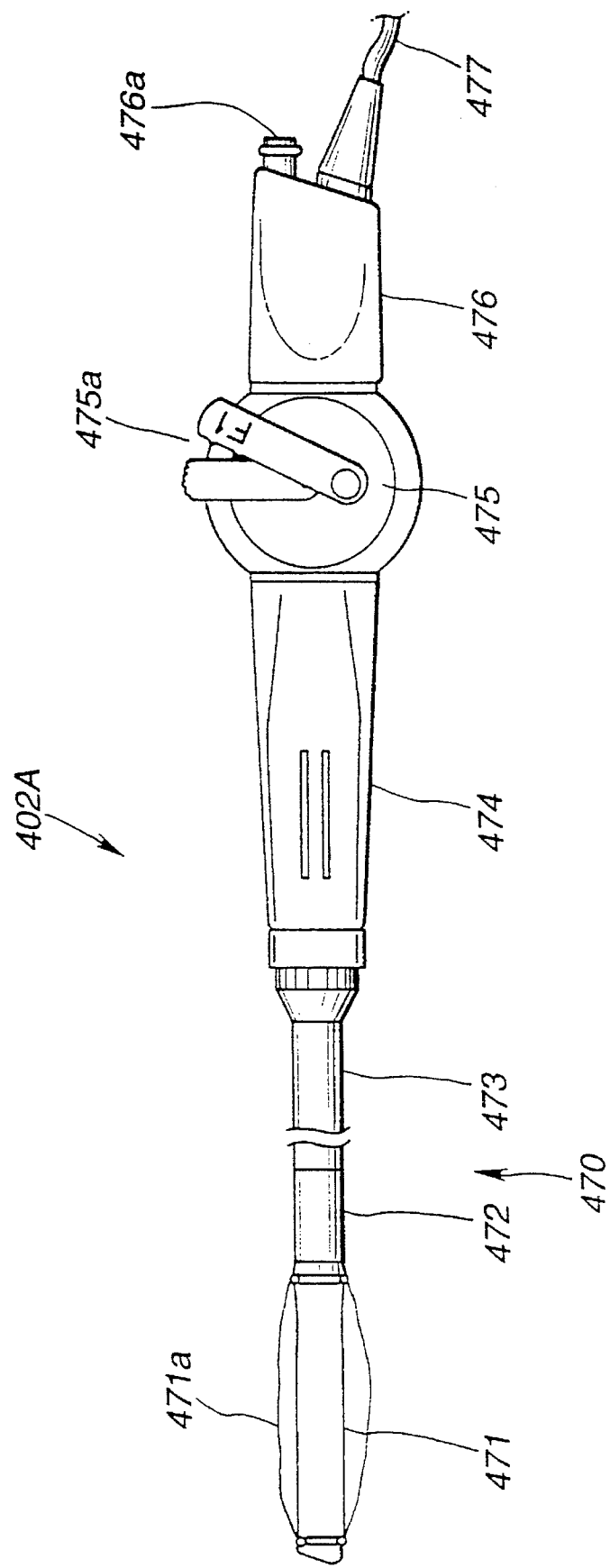
FIG. 63 to FIG. 70 relate to a twenty-second embodiment of the invention, FIG. 63 being a view showing an outer appearance of an ultrasonic probe for the interior of a peritoneal cavity, of the twenty-second embodiment.

In the twenty-second embodiment as shown in FIG. 63, the ultrasonic probe used for the ultrasonic diagnosis and therapy system 401 is an ultrasonic probe 402A used for the abdominal cavity. This probe 402A includes in turn from tip side, a end portion 471 having an ultrasonic therapy means 417 and an ultrasonic observation means 418 each being built therein and described later, an insertion part 470 formed in succession of a bendable part freely bent, for example, in up and down, and right and left directions, and hard insertion tube 473, a first grip part 474 griped when the probe 402A is inserted into the cavity, an operation part 475 provided with a bending operation knob 475a for manipulating said bendable part 472, and a second grip part 476 griped when the probe 402A is inserted into the cavity and the tip part 471 is positioned at a required point.

A balloon 471a which is freely expandable by injecting an acoustic transmission medium such as a gelable liquid thereinto, can be freely attachable to said end portion 471. Further, an universal cable 477 is extended out of the rear end of the second grip part 476.

The gelable liquid can be injected from an injection port 476a provided at the second grip 476, into the balloon 471a.

Figure 64:
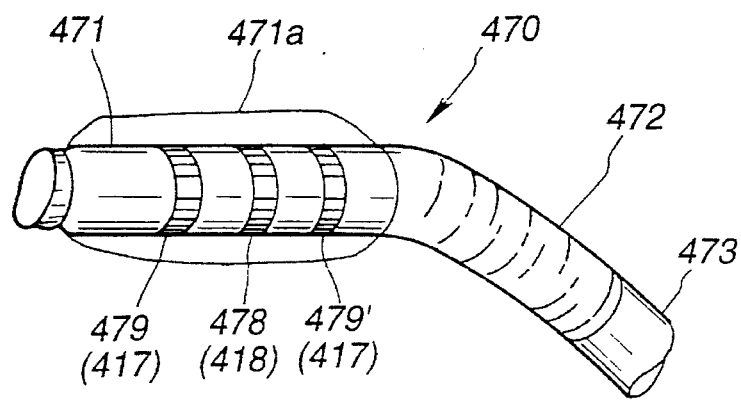

At the end portion 471 of the probe 402A as shown in FIG. 64, an electronic radial array type observatory transducer 478 is fixed in a belt shape over the full circumference at the simplified central part of the end portion 471 as the ultrasonic observation means 418, and on both sides of the transducer 478, electronic radial array type therapeutic transducers 479, 479' are fixed in a belt shape over the full circumference as the ultrasonic therapy means 417.

Figure 65:
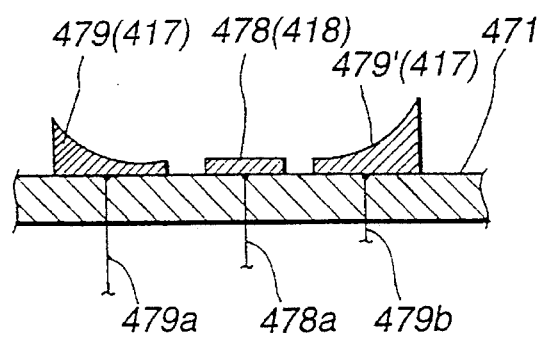

As shown in FIG. 65, the transducers 479, 479' have the same curvature and are formed symmetrically, such that the focused point is within the irradiation range of the observatory ultrasonic transducer 478.

The lead lines 478a, 479a and 479b extending out of respective transducers 478, 479 and 479' are connected to the ultrasonic diagnosis and therapy circuit not shown in the drawing, in the same manner as of said twentieth embodiment. Other configurations are the same as of said twentieth embodiment.

Figure 66:
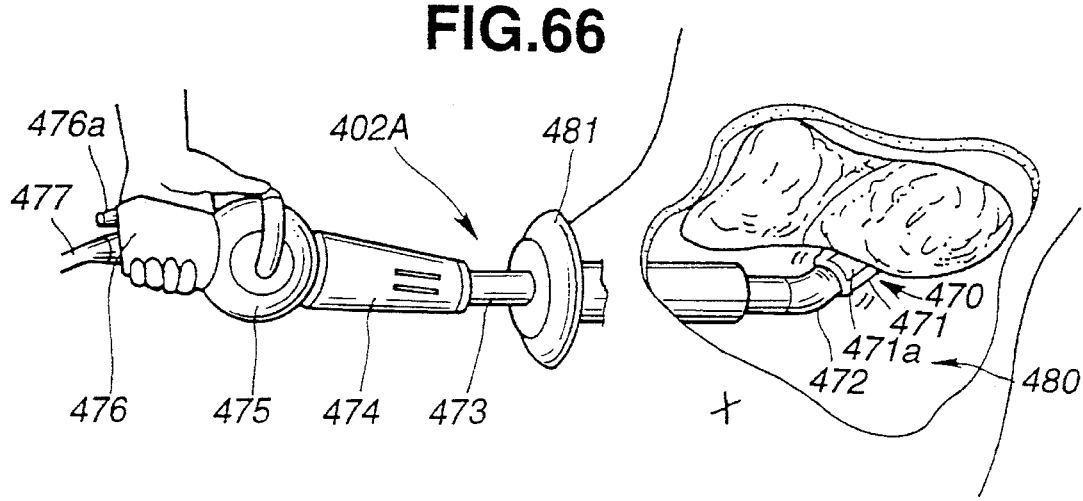

The operation of the ultrasonic probe 402A for use in an abdominal cavity for the ultrasonic diagnosis and therapy system 401 configured as described above, will be described. As shown in FIG. 66, the insertion part 470 of the probe 402A is inserted into an air injected abdominal cavity through a tracheal and the end portion 471 is positioned adjacent to a treatment region. Then, a bendable part 472 is bent by manipulating the bending operation knob 475a, such that the end portion 471 is positioned at the required point (nearly in contact with the surface of the region). Then, the observatory ultrasonic transducer 478 is scanned, and ultrasonic signals are transmitted/received, so as to display the lesion inside of the organ on a monitor.

Figure 67:
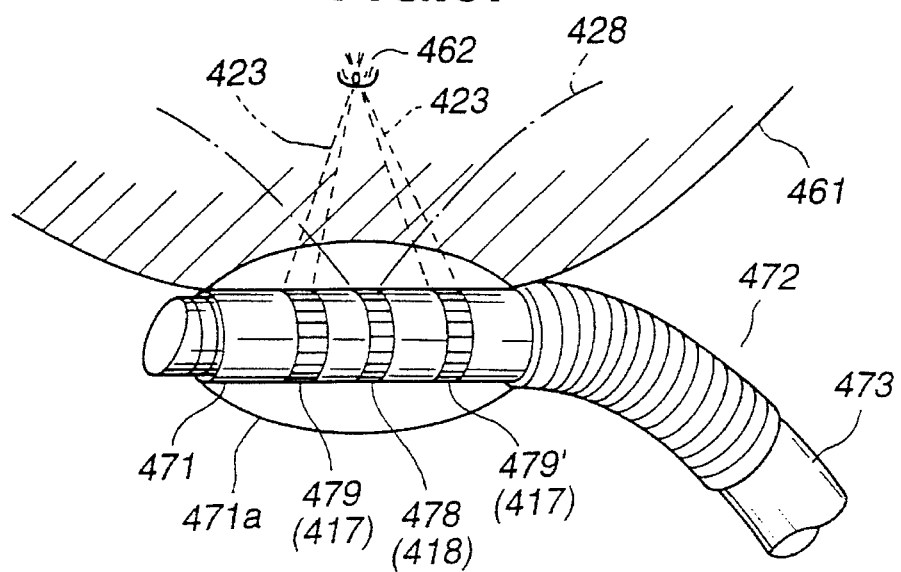

The balloon 471a is gradually expanded, and the bending operation is made for the probe 402A, and the therapeutic transducer 479, 479' is operated for electronic radial scanning perpendicular to the insertion axial direction, with reference to the ultrasonic laminagraphic image, such that the focused point of the therapeutic ultrasonic focused beam irradiated toward the treatment region 462 from the therapeutic ultrasonic transducer 479, 479' is at a required point after a treatment region 462 is captured within the ultrasonic observation region of the observatory ultrasonic transducer 478 as shown in FIG. 67, whereby positioning adjustment is completed.

Ultrasonic energy is irradiated from the transducers 479, 479' onto the treatment region 462 to cauterize the lesion organ in the same manner as of said twentieth embodiment, immediately after the positioning adjustment between said transducer 479, 479' and treatment region 462 is completed.

In this manner, the ultrasonic probe may not only be limited to a soft mirror, but also may be used for a hard mirror. Other operations and advantages will be the same as of said twentieth embodiment.

Figure 68:
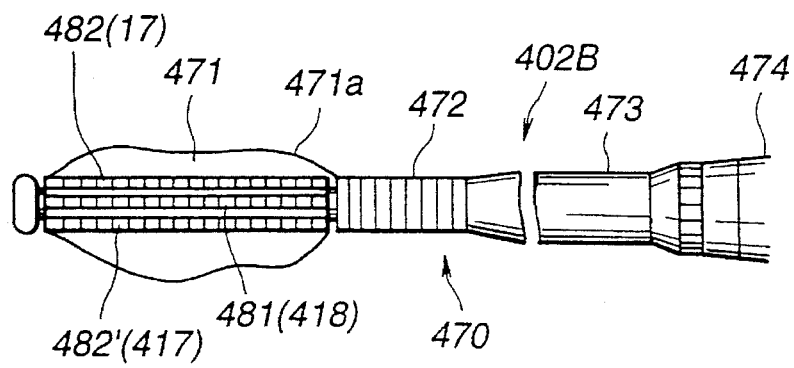

As shown in FIG. 68, an electronic linear array type observatory transducer 481 is provided in the axial direction at the end portion 471 of the probe 402B used in an abdominal cavity as the ultrasonic observation means 418 and observatory transducers 482, 482' are provided as the ultrasonic therapy means 417, such that positioning adjustment is made by scanning ultrasonic waves in the axial direction against the treatment region 62, instead of the electronic radial array type observatory transducer 478 described in the application of the twentieth embodiment and therapeutic transducer 479, 479'.

Figure 69:
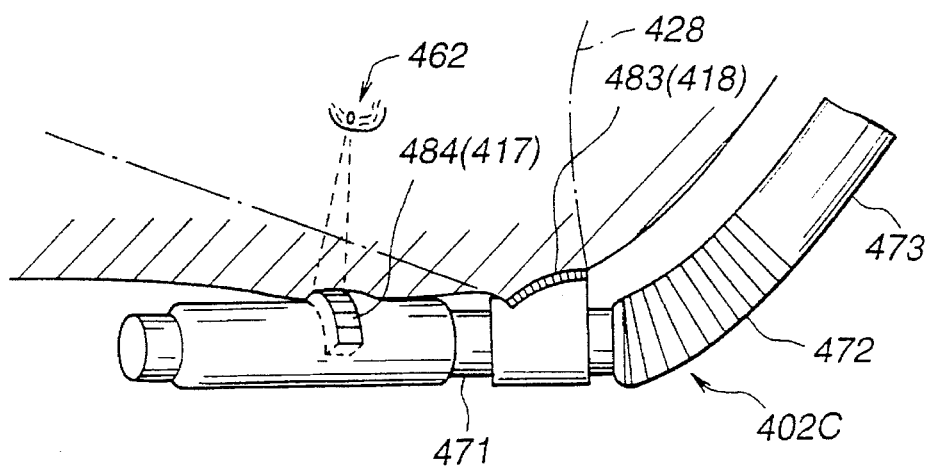
Figure 70:
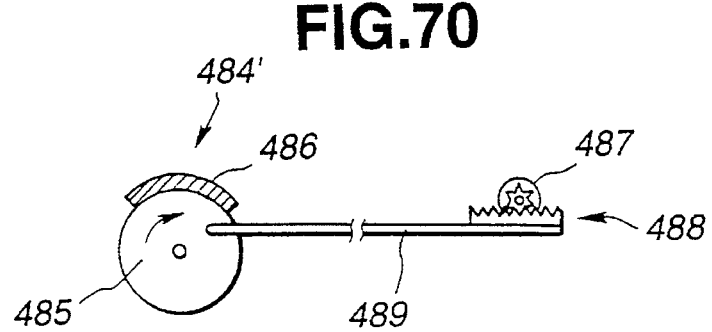

As shown in FIG. 69, a convex array type observatory ultrasonic transducer 483 having an observation range set in the forward oblique direction is fixed on this side of the tip part in front of the bendable part of the end portion 471 of a probe 402C as the ultrasonic observation means 418, and an electronic sector array type therapeutic ultrasonic transducer 484 is fixed at the center of end portion 471 as the ultrasonic therapy means 417, such that positioning adjustment of the focused point is made against the treatment region 462 to allow therapy.

For this probe 402C, the observatory ultrasonic transducer 483 is offset to cover the forward oblique range, so the transducer 483 and 484 can be separately provided, thus, the configuration can be also simplified, and it is possible to increase the opening diameter of the transducer 484, so as to improve efficiency in therapy.

The transducer 484 can control ultrasonic irradiation electronically perpendicular to the insertion axial direction. Other configurations are the same as of the embodiment previously described, and like reference characters denote like parts, and the description will be omitted.

The electronic sector array type therapeutic ultrasonic transducer 484 shown in FIG. 69 may be, so called, an mechanical sector type therapeutic transducer 484', wherein a therapeutic ultrasonic transducer 486 is fixed on a drum 485 as shown in FIG. 69, for example, rotational force by a motor 487 provided in the operation part is converted into linear movement to be transmitted to a shaft 489, so that sector scanning is made by the transducer 486 fixed on the drum 485.

Other embodiment will be described on the basis of the twentieth embodiment.

Figure 71:
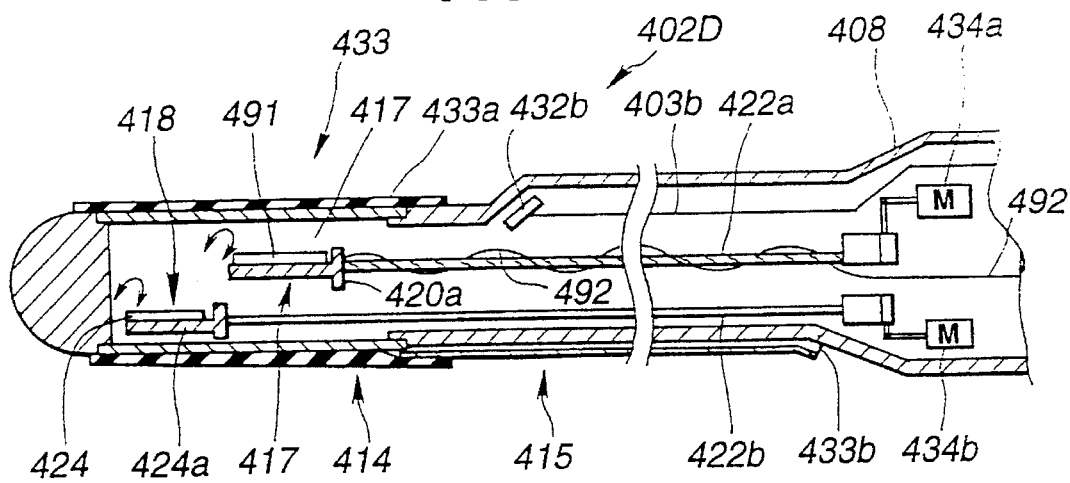
FIG. 71 is a cross-sectional view showing a schematic arrangement of a distal-end part of an ultrasonic probe to which a twenty-third embodiment of the invention relates.

FIG. 71 is a sectional view showing the schematic structure of the tip part of an ultrasonic probe 402D according to the forth embodiment of the invention.

As shown in the drawing, a therapeutic ultrasonic transducer 420 as the ultrasonic therapy means 417 in said first embodiment, is fixed at the fixed member 420a, and rotational force of the motor 434a is transmitted to the flexible shaft 422a for mechanical scanning, however, in this embodiment, the ultrasonic transducer 91 of a linear type transducer array is fixed at the fixed member as the means 417.

Scanning in the axial direction can be electronically achieved through a lead line 492 from this transducer 491 to the operation part.

Mechanical radial scanning can be possible by rotating the motor 434a on this side in the same manner as of the first embodiment. Namely, in this embodiment, the transducer 91 as the therapeutic ultrasonic means 17 can perform both the electronic linear scanning and mechanical radial scanning. The other configuration is similar to of the first embodiment, and like reference characters denote like parts, and the description will be omitted.

In the ultrasonic diagnosis and therapy system configured as above described, after the end portion 414 of insertion part is inserted adjacent to the treatment region in the same manner as in the twentieth embodiment, the region is mechanical radial scanned with the observatory ultrasonic transducer 424 to obtain an ultrasonic laminagraphic image.

Electronic scanning is made by the ultrasonic transducer 491 of the linear type transducer array for therapy for positioning control in the axial direction while the image on the monitor is observed, in the mean time, mechanical radial scanning with the transducer 491 is made by the rotational force of the motor 434a for positioning control perpendicular to the axial direction, and the variant of expansion for the balloon 433a is adjusted for the adjustment of distance in depth, and after the positioning adjustment of the focused point against the treatment region is completed, ultrasonic waves are irradiated onto the region. Other configurations are the same as of said first embodiment.

In this way, an linear type transducer array is employed as the ultrasonic transducer which is the ultrasonic therapy means, so as to allow electronic scanning in the axial direction, and the positioning control in depth is also allowed with the variant of balloon expansion. The focused point of ultrasonic waves to be irradiated onto the treatment region can be adjusted in 3-dimensions, so as to improve irradiation accuracy to the region and ensure therapy.

Instead of the use of the linear type transducer array as the transducer which is said therapy means, an electronic radial type transducer array which is the ultrasonic observation means, provided at the tip part side, is connected to a motor provided at the operation part on this side, so as to allow mechanical linear scanning, and the same advantages can be obtained even in this configuration. Further, it may be a configuration in that, an electronic sector type transducer array which is the ultrasonic observation means, provided at the tip part side, is connected to the motor provided at the operation part on this side, so as to allow mechanical linear scanning.

In addition, it may be configured that, a mechanical sector type transducer which is the ultrasonic observation means, at the tip part side, is connected to the motor provided at the operation part on this side, so as to allow mechanical linear scanning. Further, it may be configurated that, an mechanical linear type transducer which is the ultrasonic observation means, at the tip part side, is connected to the motor provided at the operation part on this side, so as to allow mechanical radial scanning.

Figure 72:
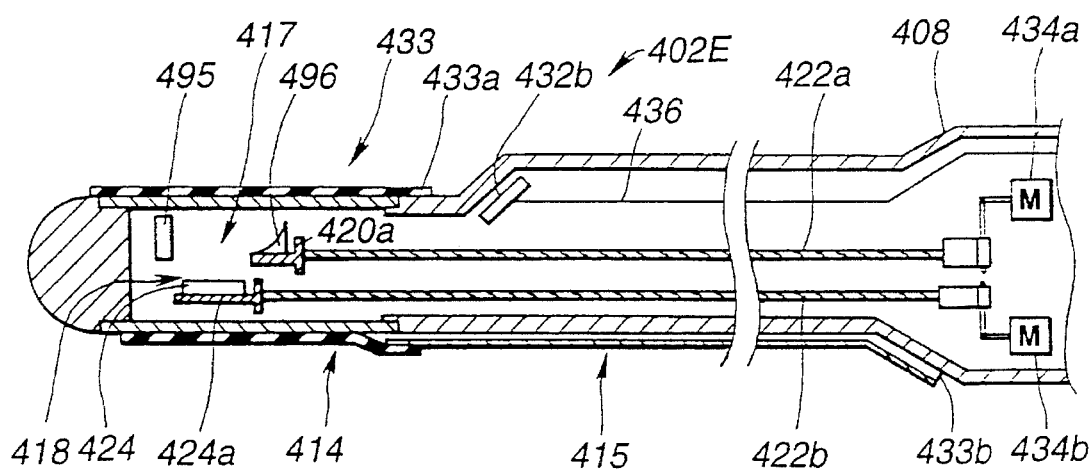
FIG. 72 is a cross-sectional view showing a schematic arrangement of a distal-end part of an ultrasonic probe to which a twenty-fourth embodiment of the invention relates.

FIG. 72 is a sectional view showing a schematic structure of the end portion of an ultrasonic probe 402E according to the twenty-fourth embodiment of the invention.

As shown in the drawing, in this embodiment, similarly in the twentieth embodiment, an observatory ultrasonic transducer 424 which is the ultrasonic observation means 418, is fixed at a fixed member 424a, and rotational force by the motor 434b provided in the operation part on this side is transmitted to a flexible shaft 422b so as to allow mechanical radial scanning.

A plane transducer 495 for therapy is fixed at the tip side of the end portion 414 as the ultrasonic therapeutic means 417, while a reflective irradiation mirror 496 for reflecting ultrasonic waves irradiated from said therapeutic plane transducer 495, in a predetermined direction, is provided at a fixed member 420a which is rotatable as turning force by a motor 433a is transmitted to the flexible shaft 422a. The other configuration is similar to of the twentieth embodiment, and like reference characters denote like parts in the twentieth embodiment, and the description will be omitted.

In the ultrasonic diagnosis and therapy system configured as above described, after the end portion 414 of insertion part is inserted adjacent to the treatment region in the same manner as in the twentieth embodiment, the region is mechanical radial scanned with the observatory ultrasonic transducer 424 to obtain an ultrasonic laminagraphic image.

Mechanical radial scanning is made by the reflective irradiation mirror 496 rotated by the motor 434a provided at the operation part 408 on this side, so as to allow the positioning control of the focused point for the mirror 496 against the treatment region, while the image on the monitor is observed. After the control, ultrasonic waves are irradiated from a therapeutic plane transducer 495 fixed at the tip part onto the mirror 496. Then the ultrasonic waves irradiated from the transducer 495 are reflected at the mirror 496, and focused on the target treatment region so as to make therapy. The other configuration is similar to of said embodiment.

Figure 73:
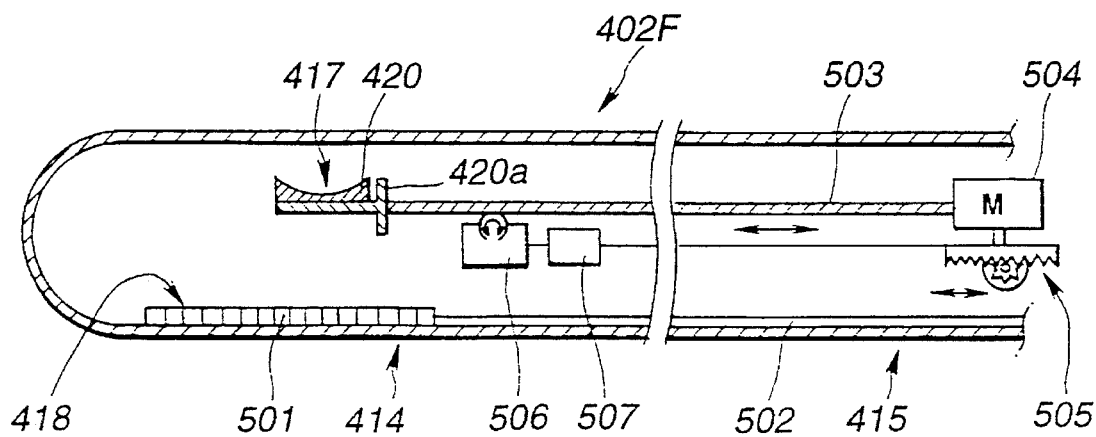
FIG. 73 is a cross-sectional view showing a schematic arrangement of a distal-end part of an ultrasonic probe to which a twenty-fifth embodiment of the invention relates.

FIG. 73 is a sectional view showing a schematic configuration of the end portion of an ultrasonic probe 402F according to the twenty-fifth embodiment of the invention.

As shown in the drawing, in this embodiment, an observatory electronic linear type transducer array 501 is provided at the end portion of an ultrasonic, probe 402F as the ultrasonic observation means 418, so that observation in the axial direction is achieved by lead line 502 extended on this side from the array 501.

In the mean time, the therapeutic ultrasonic transducer 420 which is the ultrasonic therapy means 417, is fixed at the fixed member 420a, but the member 420a is connected to a shaft 503. The shaft 503 can be given the linear movement in the axial direction by a rack and pinion mechanism which converts rotational force by a motor 504 provided at the operation part 408 on this side into linear movement.

A conversion part 506 which is in contact with the shaft 503 at the end portion 414 of the probe 402F and converts the linear movement of the shaft 503 into the rotational movement, is connected to a small sized encoder 507 which reads the rotational variant of the conversion part 106 and measures the linear distance of the shaft 503. The other configuration is similar to of the twentieth embodiment, and like reference characters denote like parts in the twentieth embodiment, and the description will be omitted.

In the ultrasonic diagnosis and therapy system configured as above described, after the end portion 414 of the insertion part is inserted adjacent to the treatment region in the same manner as in the twentieth embodiment, the region in the axial direction is observed by scanning with an observatory electronic linear type transducer array 501. When the region is captured, the shaft 503 is linearly driven by the rotation of the motor 504 through the rack and pinion mechanism 505, so as to allow linear scanning with the therapeutic ultrasonic transducer 420. In the mean time, the linear variant of the therapeutic transducer 420 in the axial direction is read by the conversion part 506 and encoder 507, and the rotational variant of the motor 504 is adjusted on the basis of the ultrasonic laminagraphic image of said array 501 and the linear variant detected, and the variant of the transducer 520 in the axial direction is numerically controlled, whereby the variant is appropriately adjusted, so that ultrasonic waves irradiated from the transducer 520 are effectively focused on the treatment region. Other operations will be the same as of said embodiment.

In this manner, the variant of therapeutic ultrasonic transducer in the axial direction is read by the encoder through the conversion part, such that accuracy in focusing ultrasonic waves irradiated from the transducer, on the treatment region, is improved. Other advantages will be the same as of said twentieth embodiment.

It is not limited to the configuration in that the encoder detecting the variant of the therapeutic transducer is provided only at the end portion, so it may be configured that the encoder is provided at both tip part and this side part or only at this side part.

Figure 74:
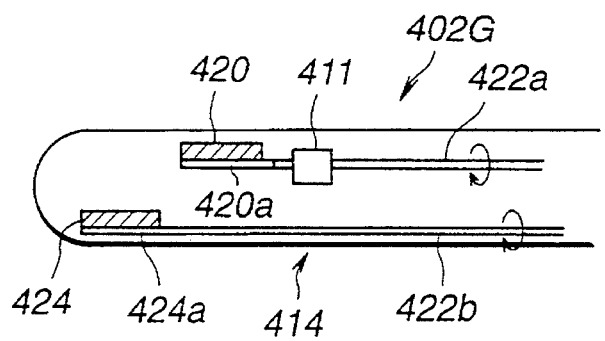
FIG. 74 to FIG. 76 relate to a twenty-sixth embodiment of the invention, FIG. 74 being a view showing a schematic arrangement of a distal-end part of an ultrasonic probe.

As shown in FIG. 74, in the end portion 414 of an ultrasonic probe 402G in the twenty-sixth embodiment, similarly as in the twentieth embodiment, it is configured that the therapeutic transducer 420 and observatory transducer 424 are fixed at the fixed members 420a, 424a, respectively, and the rotation of motor not shown in the drawing is transmitted to the flexible shafts 422a, 422b to allow mechanical radial scanning. In addition, a rotation detection part 111 which will be described later, is provided at the flexible shaft 422a which rotates said transducer 420.

Figure 75:
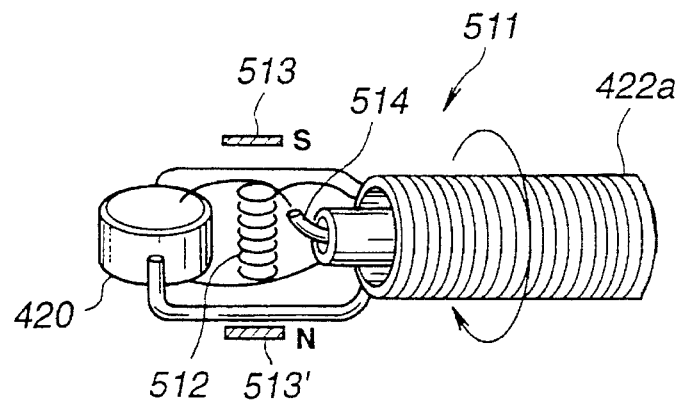

As shown in FIG. 75, the rotation detection part 511 is connected to an inductor 512 in parallel with the therapeutic transducer 420, and magnets 513, 513' are arranged outside of the inductor 511, such that electro motive force by electromagnetic induction is generated in the inductor 511 in response to the rotation of the transducer 420.

One end of the flexible shaft 422a is connected to the transducer 420, and the other end of the shaft 422a is coupled with the rotational shaft of a motor in a drive unit not shown in the drawing.

A coaxial cable 514 is connected to the therapeutic ultrasonic transducer 420 and inductor 512, and the cable 514 is connected to a transmit/receive circuit which will be described later, passing through into the radial center of the shaft 422a.

Figure 76:
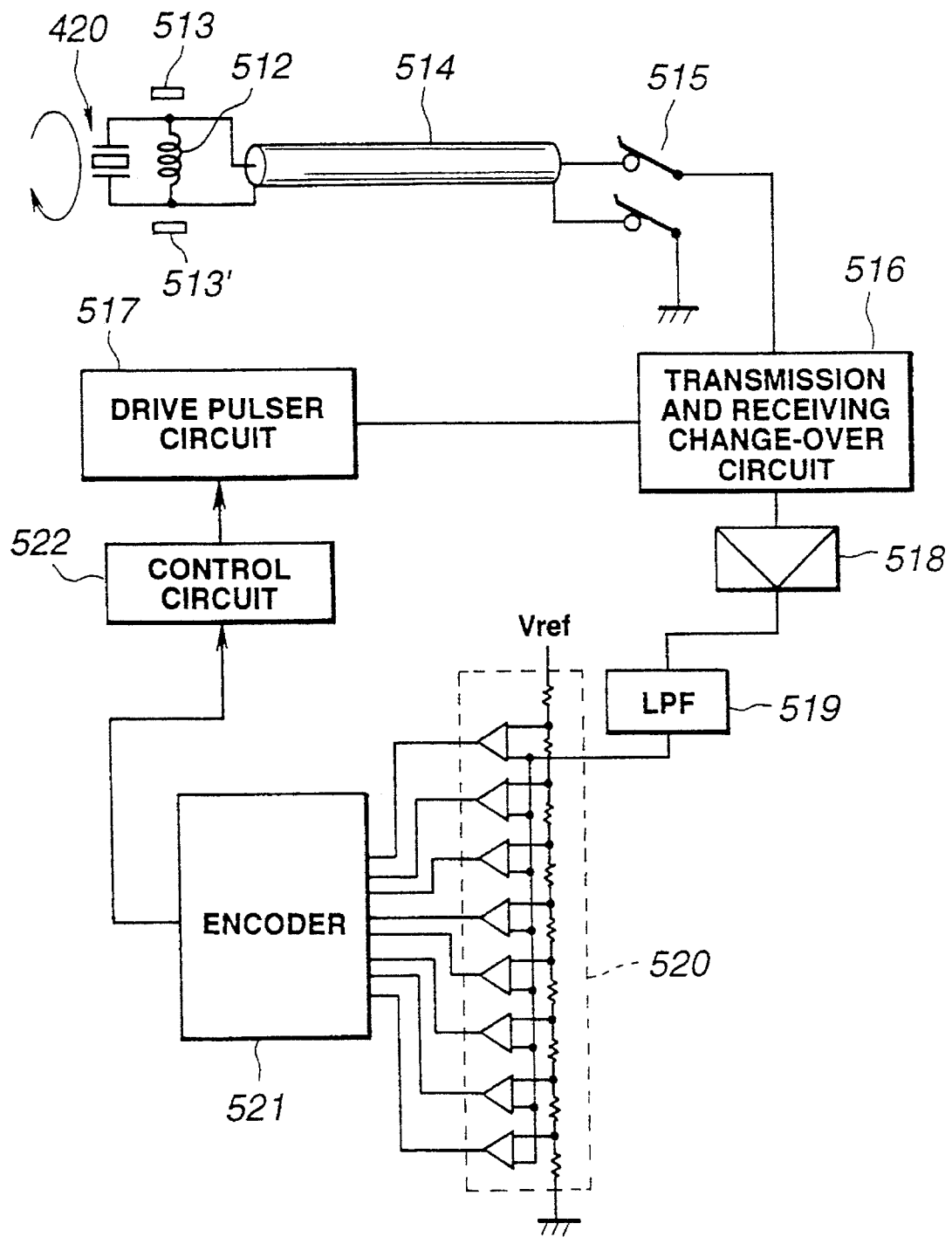

As shown in FIG. 76, the coaxial cable 514 extending out of the transducer 420 is connected to a transmit/receive switching circuit 516 through a slip ring 515. The circuit 516 is separately connected to a driving pulser circuit for generating transmit/receive driving pulses 517 and a pre-amplifier 518.

The output of said pre-amplifier 518 is supplied to a comparator 520 through a low-pass filter (LPF) 519, and the output of the comparator 520 is supplied to an encoder 521. The output of the encoder 521 is supplied to a control circuit for the driving pulser circuit 517.

In the ultrasonic diagnosis and therapy system configured as above described, after the end portion 414 of insertion part is inserted adjacent to the treatment region in the same manner as in the twentieth embodiment, the target diseased region in the transversal direction is observed by the observatory ultrasonic transducer 424.

Then ultrasonic laminagraphic image from said transducer 424 and the detected oscillation (oscillation produced by electromagnetic induction generated by the rotation of the transducer 420) from the rotation detection part 511 are read to determine the focused position of the therapeutic ultrasonic waves, and the transducer 420 is rotated by the motor to be an appropriate position on the basis of the detected signals if correction in position is required. After that ultrasonic waves from the transducer 420 is irradiated onto the treatment region so as to achieve therapy.

In this manner, the detection part which reads the variant perpendicular to the insertion axial direction, is provided adjacent to the therapeutic ultrasonic transducer, whereby accuracy for focusing ultrasonic waves on the treatment region can be improved, similarly as in said twenty-fifth embodiment.

Figure 77:
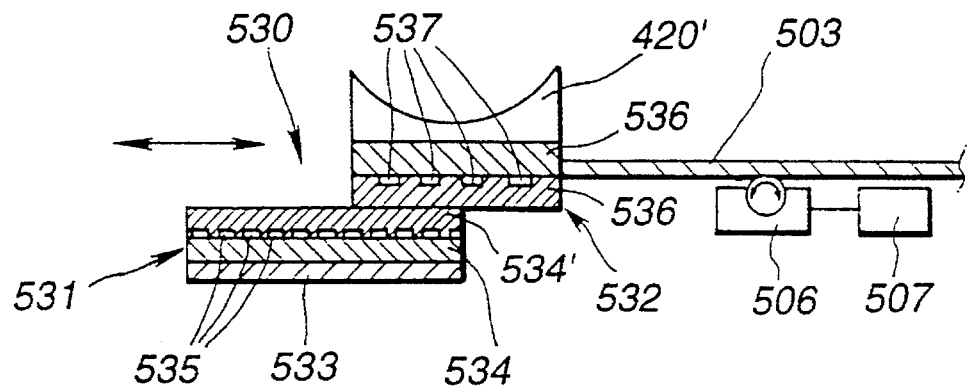
FIG. 77 to FIG. 79 relate to a twenty-seventh embodiment of the invention, FIG. 77 being an explanatory view showing linear scanning of a therapeutic ultrasonic transducer in the twenty-seventh embodiment.

FIG. 77 is an illustrative diagram showing the linear scanning of a therapeutic ultrasonic transducer according to the twenty-seventh embodiment of the invention.

In this invention, the linear scanning of the therapeutic ultrasonic transducer 420' provided at the probe 402F of said twnty-fifth embodiment is carried out by an electrostatic motor 530 provided at the end portion 414, instead of the motor 504 provided at this side.

Said electrostatic motor 530 is configured of a stator 531 and a rotor provided against the stator, and the stator is configured to have, for example, a first insulating layer which is formed of silicon dioxide and silicon nitride or the like, provided on a silicon semiconductor substrate 533, a second insulating layer 534' provided on the first layer 534, and a plurality of electrodes 535 which are formed of aluminum or the like, provided between the first and second insulating layers 534 and 534'.

On the other hand, the rotor 532 is configured to have a first insulating layer 536 fixed on a second insulating layer 536', and a plurality of electrodes 537 provided between the first and second insulating layers 536 and 536'.

The second layer 534' of said stator 531 and the second layer 536' of said rotor 532 are slidably contacted each other.

A pitch of the electrodes 535 provided at said stator 531 is shorter than of the electrodes 537 at said rotor 532, so the rotor 532 can move in the insertion axial direction in relation to the stator 531 when voltage is applied to the electrodes. The shaft 503 is also connected to said rotor 532. The other configuration is similar to of said twenty-fifth embodiment, and like reference characters denote like parts, and the description will be omitted.

In the ultrasonic diagnosis and therapy system configured as above described, after the end portion 414 of insertion part is inserted adjacent to the treatment region in the same manner as in the twentieth embodiment, when the treatment region is determined, voltage is applied to the electrodes 135 of the electrostatic motor 530 to drive the shaft 503 linearly so as to allow linear scanning with the therapeutic ultrasonic transducer 420'.

Then, the variant of the transducer 420' in the axial direction is read by the conversion part 106 and encoder 507, and the variant of the transducer 420' in the axial direction is numerically controlled on the basis of the ultrasonic laminagraphic image of said observatory electronic linear type transducer array 501 and the variant detected, whereby the variant is appropriately adjusted, so that ultrasonic waves irradiated from the transducer 420' are effectively focused on the treatment region. Other operations will be the same as of said twenty-fifth embodiment.

In this manner, the variant of the therapeutic ultrasonic transducer is read by the encoder, similarly as in the sixth embodiment, such that accuracy in focusing ultrasonic waves on the treatment region is improved, in addition to this, the workability of an operator is extremely improved, since the therapeutic transducer is driven by a leading actuator.

Figure 78:
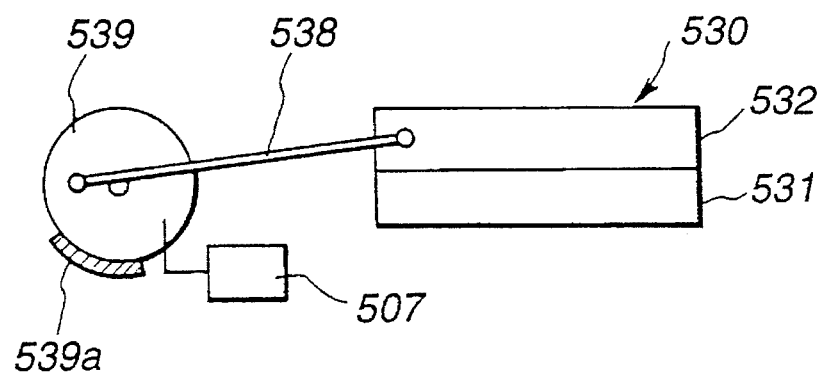
Figure 79:
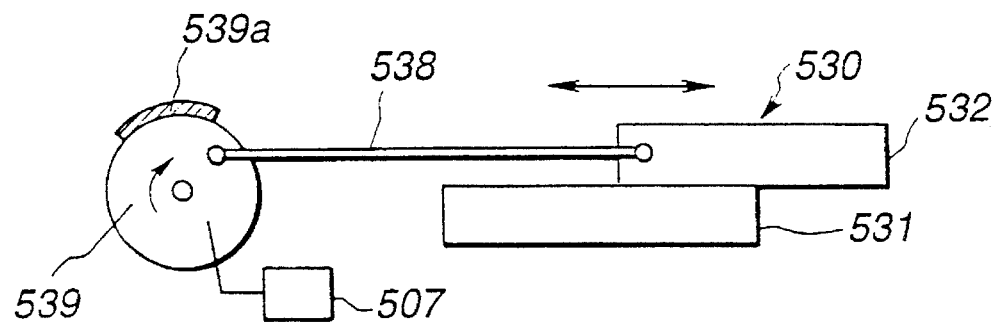

As shown in FIGS. 78 and 79, it may be configured that one end of a shaft 538 is connected to the electrostatic motor 530, and the other end of the shaft 538 is fixed at a drum 539 fixed at the therapeutic ultrasonic transducer 539*a*, and then sector scanning with the transducer 539*a* can be made by the linear movement of the motor 530. In the mean time, if the encoder 507 is connected adjacent to the drum 539, the position of the transducer 539*a* will be accurately obtained by detecting the variant of the drum 539, so that accuracy in focusing ultrasonic waves on the treatment region is improved.

Figure 80:
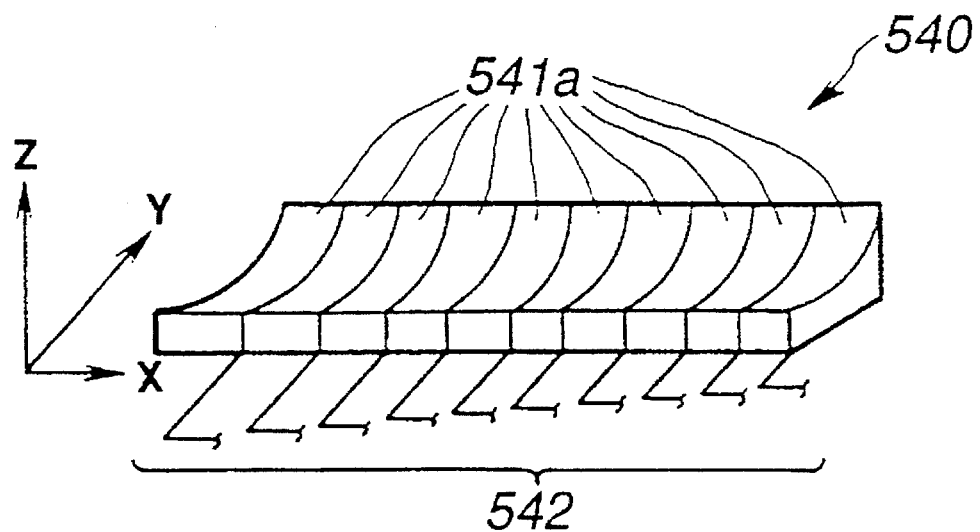
FIG. 80 and FIG. 81 relate to a twenty-eighth embodiment of the invention, FIG. 80 being an explanatory view showing a schematic arrangement of a therapeutic ultrasonic transducer in the twenty-eighth embodiment.

FIG. 80 is an illustrative diagram showing a schematic structure of the therapeutic ultrasonic transducer according to the twenty-eighth embodiment of the invention.

As shown in the drawing, a therapeutic ultrasonic transducer 540 is formed of phased arrays including a plurality of therapeutic ultrasonic transducers 541*a*, 541*a*, 541*a*, . . . configured in a specific curvature and arranged in turn from the tip side in the insertion axial direction, and lead lines 542 extended out of each transducer 541*a*, 541*a*, 541*a*, . . . are connected to a control part at this side not shown in the drawing.

The therapeutic ultrasonic transducer 540 configured as above described, is formed to arrange a plurality of therapeutic ultrasonic transducers having a specific curvature for each, 541*a*, 541*a*, 541*a* . . . , so the focused position in the Y direction can be determined unconditionally by the curvature. Applied voltage is controlled by the control part at this side not shown in the drawing through the lead line 542, whereby the focused position in the XZ directions is positioned as required.

In this manner, the therapeutic ultrasonic transducer is formed with the phased arrays and the applied voltage is controlled, whereby the ultrasonic focused position is controlled to improve accuracy in focusing ultrasonic waves.

Figure 81:
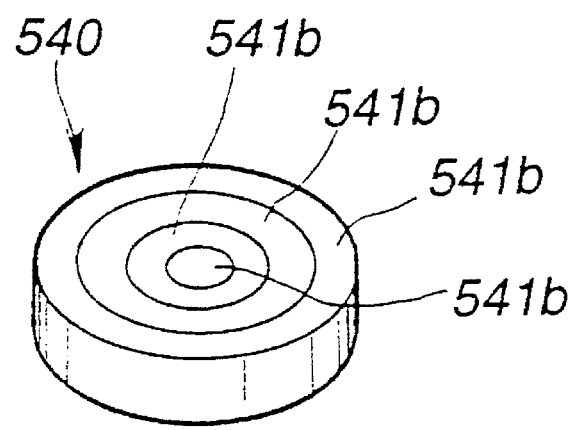

It may be configured that circular type annular transducers 541*b* as shown in FIG. 81, are arranged in turn from the center, such that focusing ultrasonic waves perpendicular to the insertion axial direction is controlled, instead of the use of the phased arrays 541 which are arranged in said axial direction and each having a specific curvature. It may also be configured that focused point in depth can be controlled with a single plate irradiation transducer consecutively changed in thickness.

Figure 82:
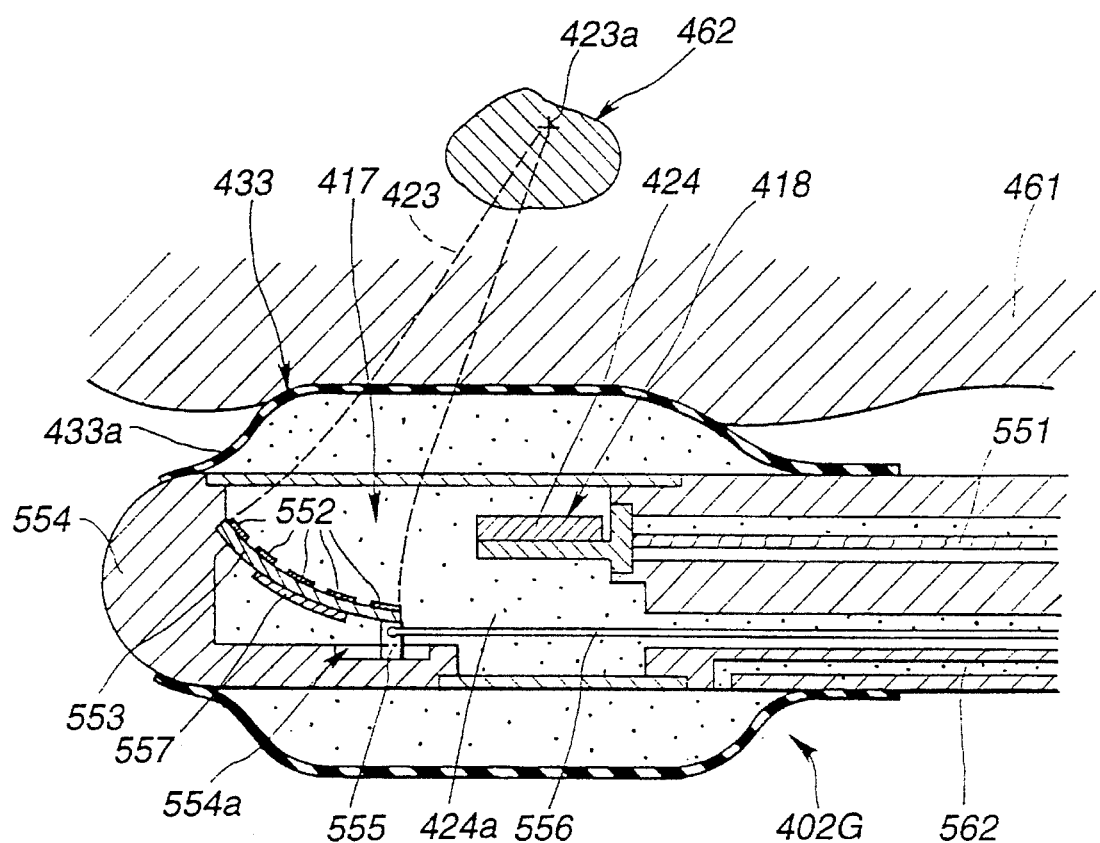

FIG. 82 is a diagram showing a schematic configuration of the end portion of an ultrasonic probe 402G in the twenty-ninth embodiment.

As shown in FIG. 82, the observatory ultrasonic transducer 424 which is the ultrasonic observation means 418, is fixed at the fixed member 424*a*, and radial scanning is achieved by a rotary shaft 551 which is freely rotatable and is fixed at the member 424*a* with its one end.

A balloon 433*a* communicating with a tubular passage 562 is provided at the end portion of the endoscope.

Meanwhile, as shown in FIG. 82 and FIGS. 84A–84C, the ultrasonic therapy means 417 is formed of a plurality of therapeutic ultrasonic transducers 552, 552, 552 . . . arranged on the silicon or urethane elastic plate 553. The elastic plate 553 is fixed at an endoscope end portion 554 with its one end and fixed at a guide member 555 with its other end.

Figure 83:
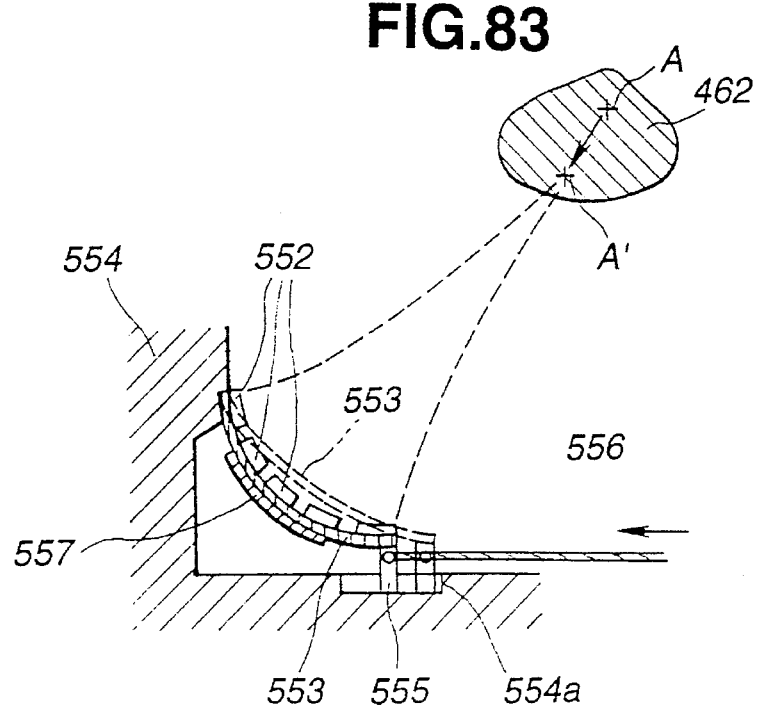
Figure 84A:
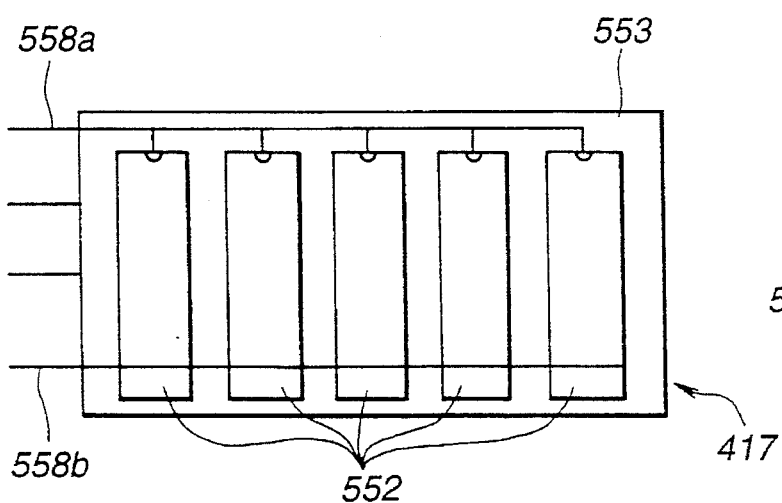
FIG. 84A, FIG. 84B and FIG. 84C are, respectively, a top plan view, a side elevational view and a rear view showing a schematic arrangement of the therapeutic ultrasonic transducer.
Figure 84B:
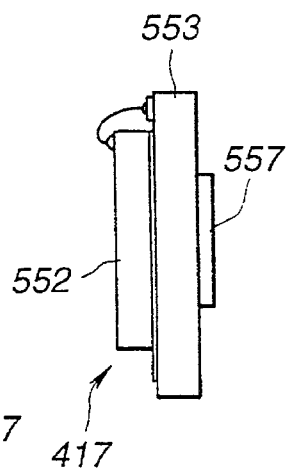
Figure 84C:
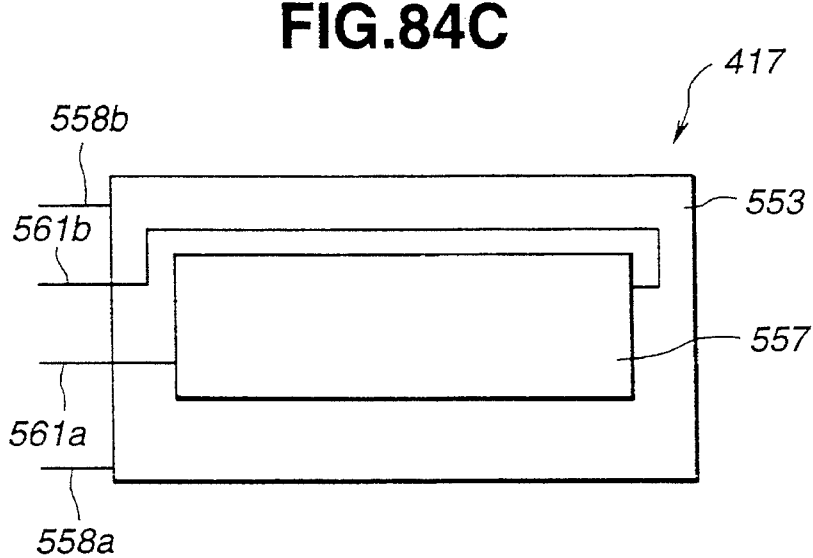

As shown in FIG. 83, said guide member 555 is slidably arranged in a slot 554*a* formed in the tip part 554. The guide member 555 slides onto the slot 554*a* in the axial direction by a push/pull operation for a wire 556 connected to the guide member 555, whereby bending the elastic plate 553 to the predetermined curvatures so as to change the focused point of ultrasonic waves in respect to the treatment region such as focused points A and A'.

A distortion sensor 557 for detecting the distortion variant of the elastic plate 553 is provided on the other side of the elastic plate.

As shown in FIGS. 84A–84C and 86, the therapeutic ultrasonic transducers 552, 552, 552 . . . are connected to a lead line 559 through electrodes 558*a*, 558*b*, and extended to the operation part 408 at this side.

Figure 85:
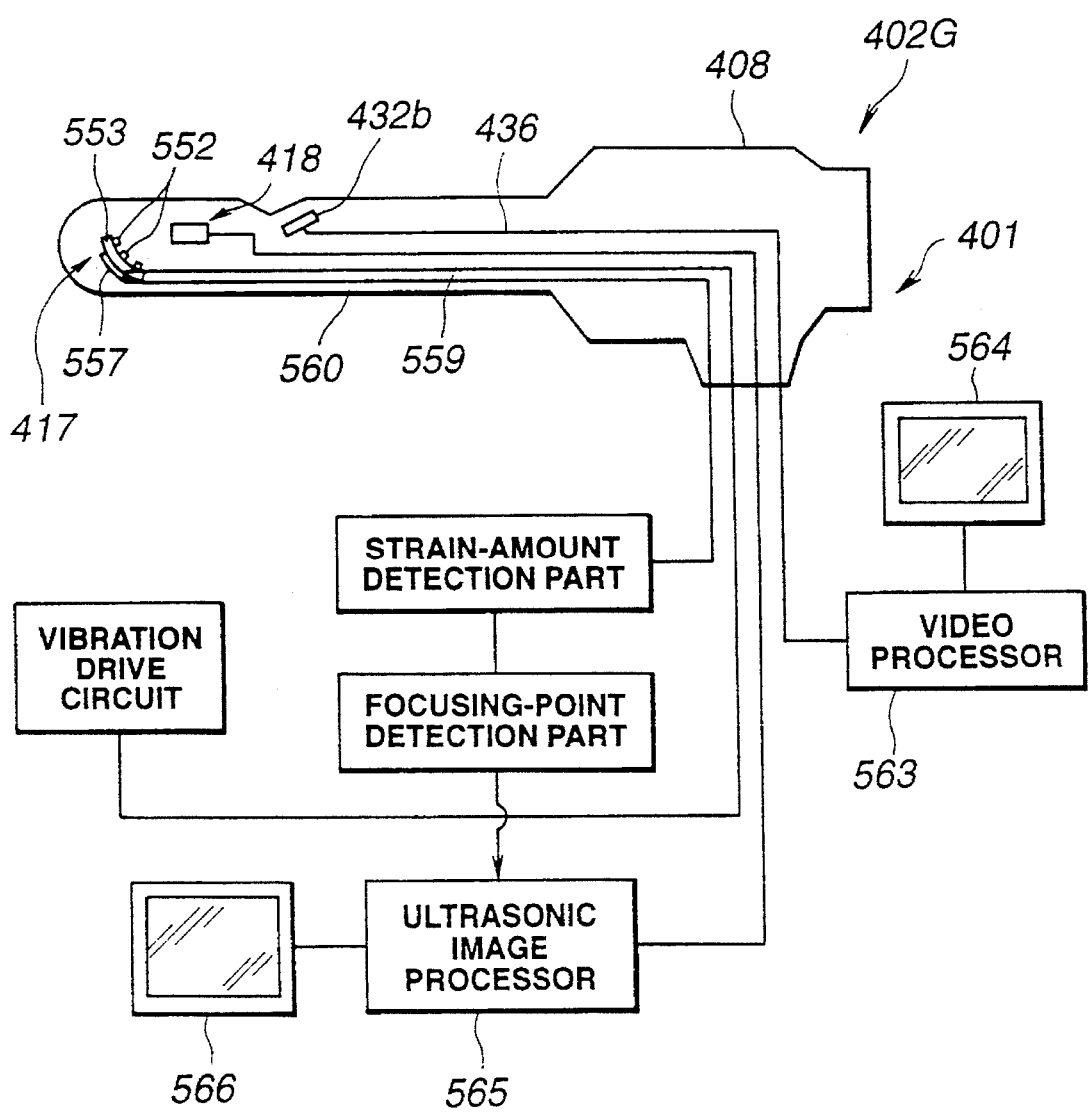

In the ultrasonic diagnosis and therapy system 401 configured as above described, as shown in FIG. 85, an optical image captured by an imaging element 432*b* such as CCD provided at an ultrasonic probe 402G is displayed on TV monitor 564 through a video processor 563, while electric signals transmitted/received by the ultrasonic observation means 418 are displayed on TV monitor 566 through an ultrasonic image processing processor 565.

The ultrasonic therapy means 417 formed of a plurality of therapeutic ultrasonic transducers 552 fixed at the elastic plate 553, is connected to an transducer driving circuit 567, and the distortion sensor provided on the reverse side of this elastic plate 553 is connected to the distortion variant detection part 568, the focused point detection part 569, and the ultrasonic image processing processor 565, respectively. The distortion variant of the elastic plate 553 is captured by the distortion sensor 557, and the focused point position of ultrasonic waves is calculated from the distortion variant to display on TV monitor 566.

Therefore, after the balloon 433*a* provided at the end portion is expanded, the wire is pulled or pushed to bend the elastic plate 553, while TV monitor 566 is observed, whereby the distortion variant of the elastic plate 553 is detected by the distortion sensor 557, and ultrasonic waves focused point calculated by the distortion variant detection part 568 and focused point detection part are checked on the TV monitor 566 while it is adjusted to be an appropriate position.

In this manner, it is configured that the therapeutic ultrasonic transducer which is the ultrasonic therapy means is arranged on the elastic plate which can be freely bent, whereby the curvature of the elastic plate is changed by pushing or pulling the wire, so as to move the ultrasonic focused point position.

With the distortion sensor attached on the elastic plate, the bending variant of the elastic plate on which the therapeutic transducers are attached, can be obtained by calculation, and the ultrasonic focused point can be displayed on TV monitor 566, so workability can be extremely improved.

Figure 86:
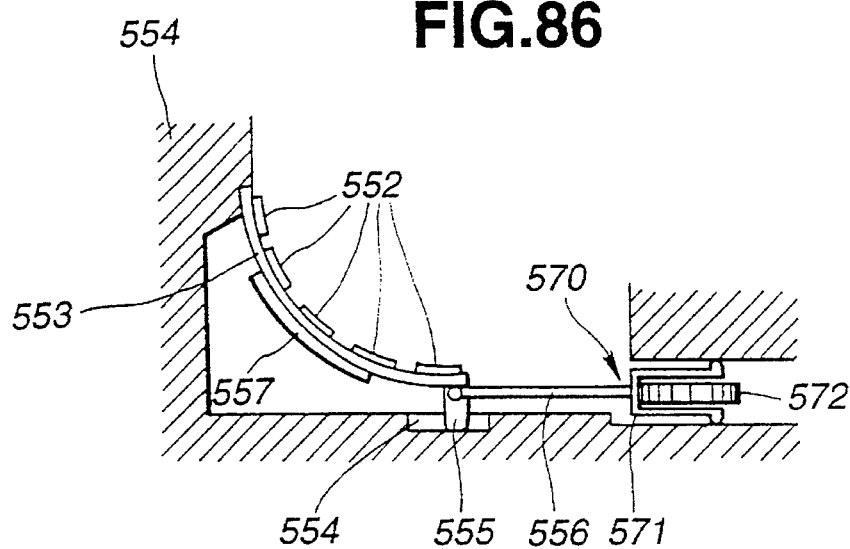

As shown in FIG. 86, in the thirtieth embodiment, it is configured with a piezoelectric actuator 570 provided at the end portion of endoscope, instead of the configuration in that the elastic plate on which a plurality of ultrasonic therapeutic transducer 552 are arranged, is bent by the push-pull movement of the wire to change the curvature in said twety-ninth embodiment.

Figure 88A:
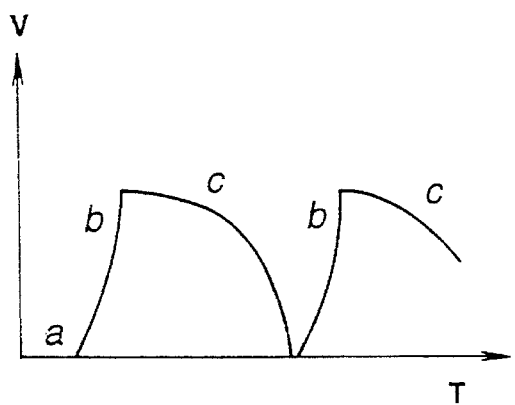
FIG. 88A and FIG. 88B are waveform views showing, respectively, voltage patterns which are applied to the piezoelectric actuator.
Figure 88B:
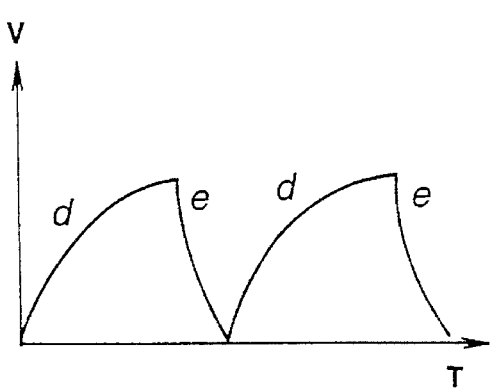
Figure 87A:
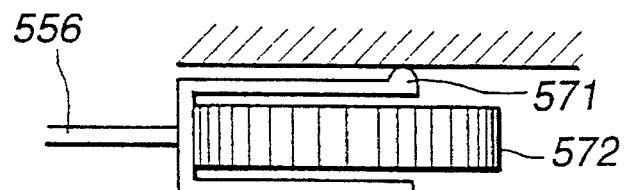
FIG. 87A to FIG. 87E are explanatory views of operation of a piezoelectric actuator of the focusing-point adjusting means.
Figure 87B:
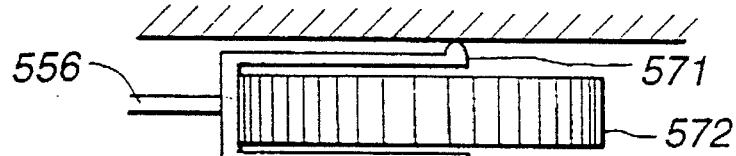
Figure 87C:
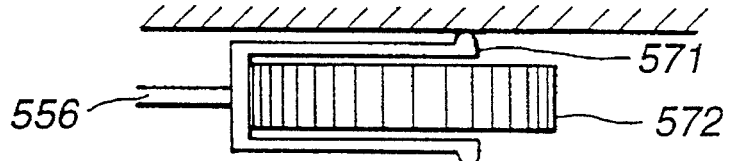
Figure 87D:
Figure 87E:
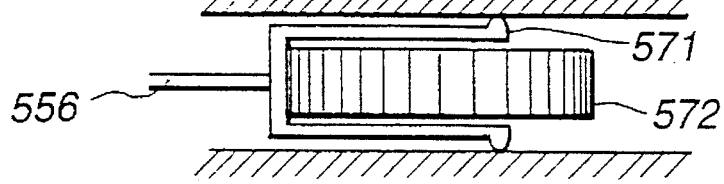

This piezoelectric actuator 570 is that has been proposed in Patent Application No. Hei 5-44140 by this applicant, and includes a moving member 571 and a laminated piezoelectric element 572, wherein as voltage pattern as shown in FIG. 88A or FIG. 88B is changed into a, b to c, or d to e, the laminated piezoelectric element 572 expands and contracts in response to the voltage pattern to move the moving member 571 in the axial direction, as shown in FIGS. 87A–87E, such that the curvature of the elastic plate is changed. The other configurations and operations are similar to of said twenty-eighth embodiment, and like reference characters denote like parts, and the description will be omitted.

In this manner, when the curvature of the bendable plate on which the therapeutic ultrasonic transducers are fixed, is required to change, the elastic plate is bent as required, by only application of voltage which drives the piezoelectric actuator, so as to change the ultrasonic focused point easily. The other advantages are the same as of said embodiment.

Figure 89:
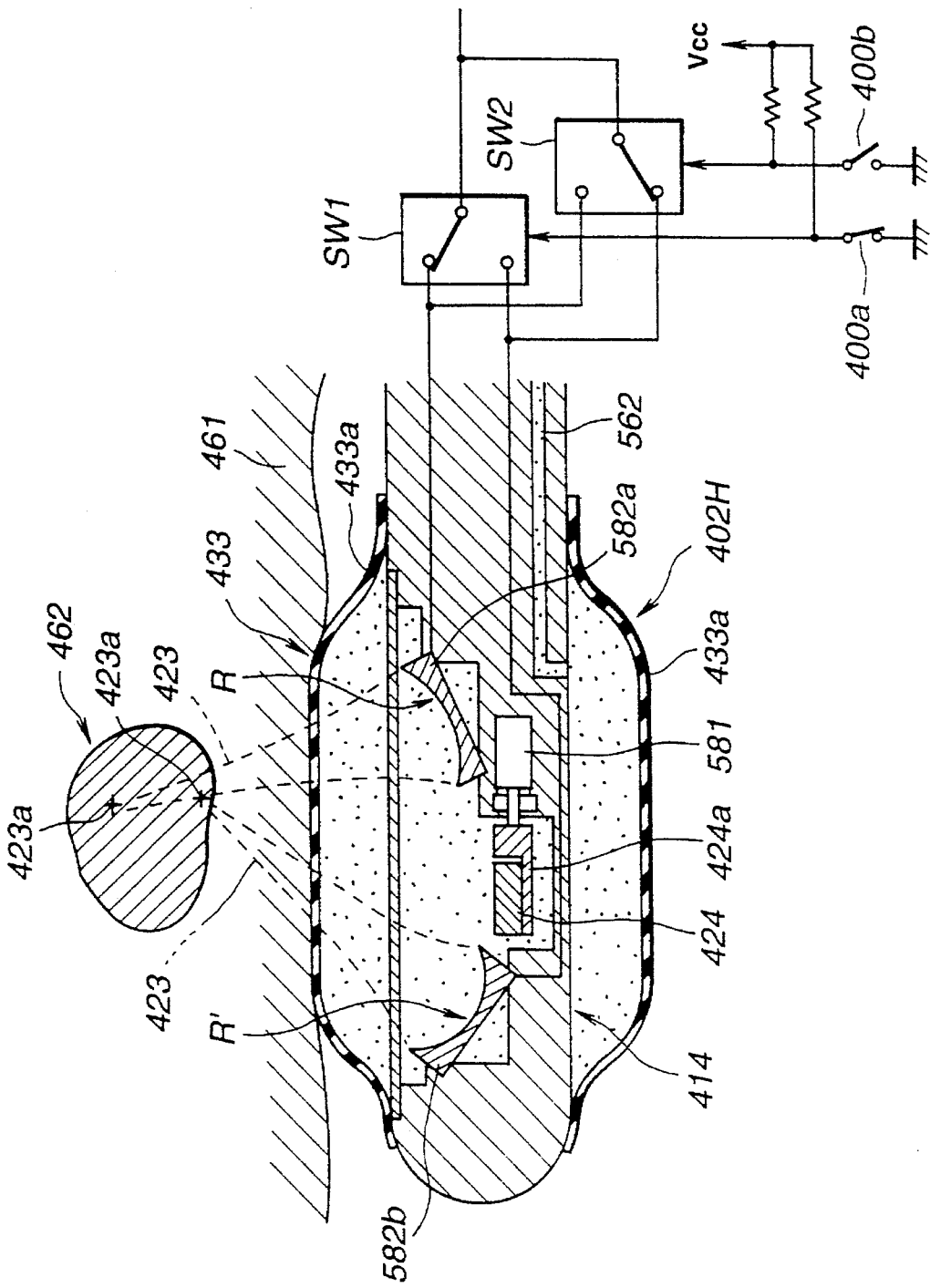
FIG. 89 to FIG. 92 relate to a thirty-first embodiment of the invention, FIG. 89 being a view showing a schematic arrangement of a distal-end part of an ultrasonic probe in the thirty-first embodiment.

FIG. 89 is a diagram showing a schematic configuration of the end portion of an ultrasonic probe 402H according to the thrty-first embodiment of the invention.

In this embodiment, a motor 581 is built in the end portion 514 of an ultrasonic probe 402H, such that the observatory ultrasonic transducer 424 is rotated by the rotation of the motor 581 to allow mechanical radial scanning.

Two therapeutic ultrasonic transducers 582a, 582b which are different in curvature R, R', namely different in focused point, are fixed from the beginning.

These transducers 582a, 582b are applied to driving signal through analog switches SW1,SW2. These analog switches SW1,SW2 select respectively one which is being driven from two transducers 582a, 582b depending upon selecting switches 400a,400b by operation of user. Since two analog switches SW1,SW2 and selecting switches 400a, 400b are prepared, not only selecting means(or exchanging means) for one of them, but also for two simultaneousuly is formed.

The other configurations are similar to of said embodiment, and like reference characters denote like parts, and the description will be omitted.

In this manner, the rotation of the motor is directly transmitted to rotate the therapeutic ultrasonic transducer, so as to allow steady mechanical radial scanning.

Further, therapeutic ultrasonic transducers which are different in focused point, are provided, whereby therapy for treatment region is ensured with the therapeutic ultrasonic transducers having the focused points corresponding to the regions. The other operations and advantages are similar to of said embodiment, Ultrasonic waves from two therapeutic ultrasonic transducers are irradiated at the same time, so as to allow the therapy for the wide treatment region at the same time.

In this embodiment, two therapeutic ultrasonic transducers which are different in curvature are provided, though, the therapeutic ultrasonic transducer provided at the end portion are not only limited to the two units, so more than 403 units of the transducers may be provided.

Figure 90:
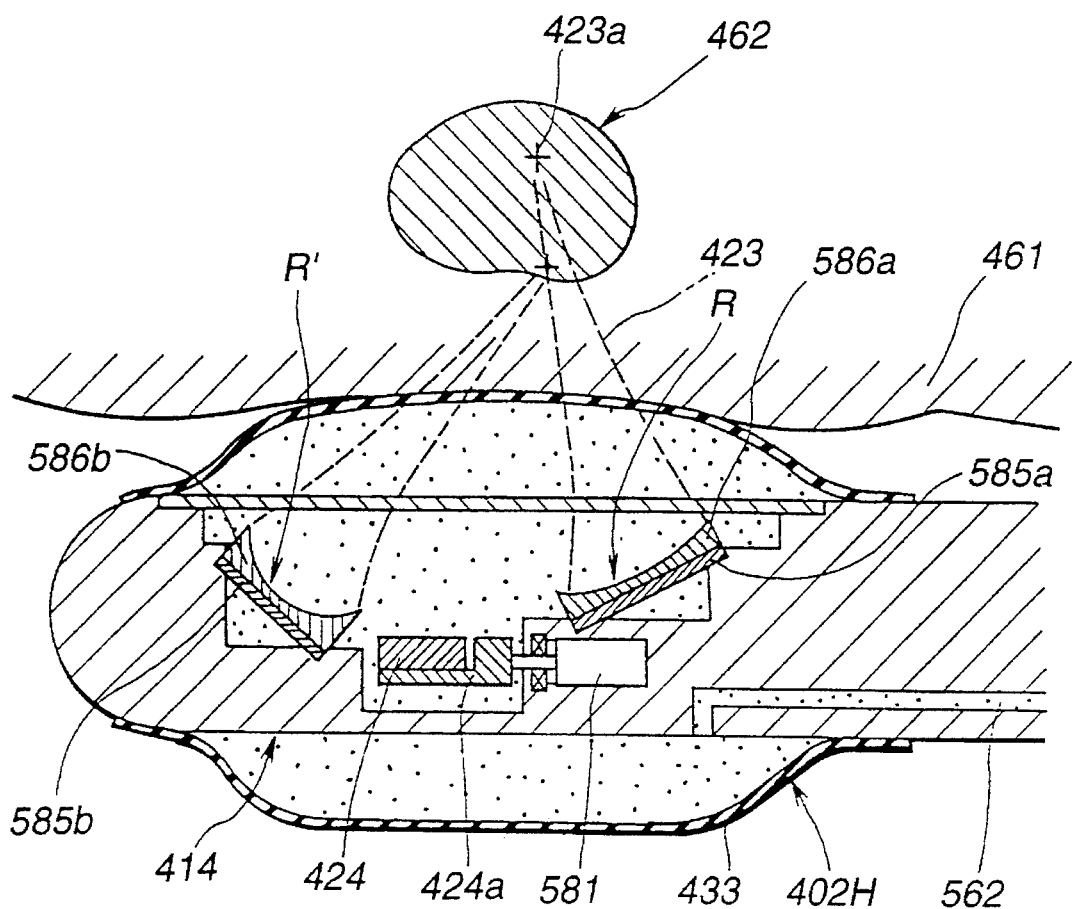

The same operations and advantages are obtainable even if acoustic lenses 586a, 586b which are different in curvature R, R', is provided on plane transducers 585a, 585b as shown in FIG. 90, instead of the use of two therapeutic ultrasonic transducers 582a, 582b which are different in curvature R, R' shown in said FIG. 89.

Figure 91:
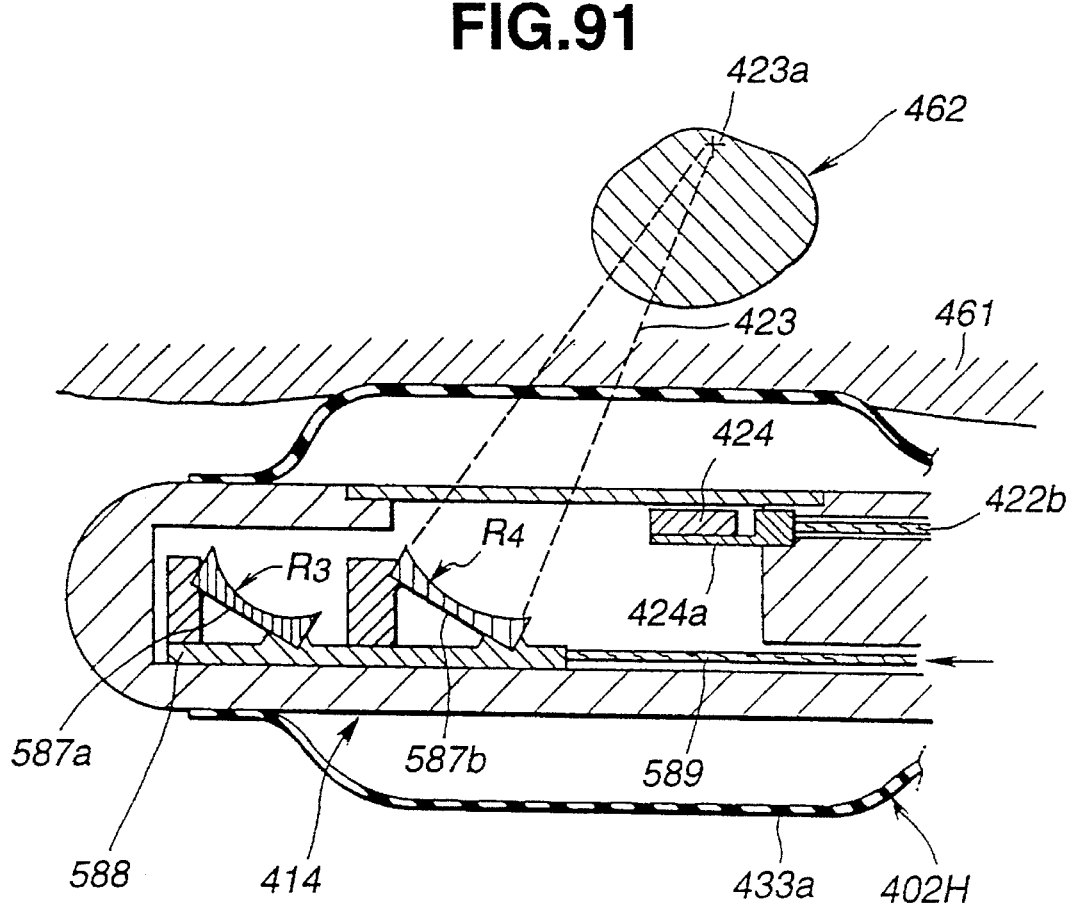
Figure 92:
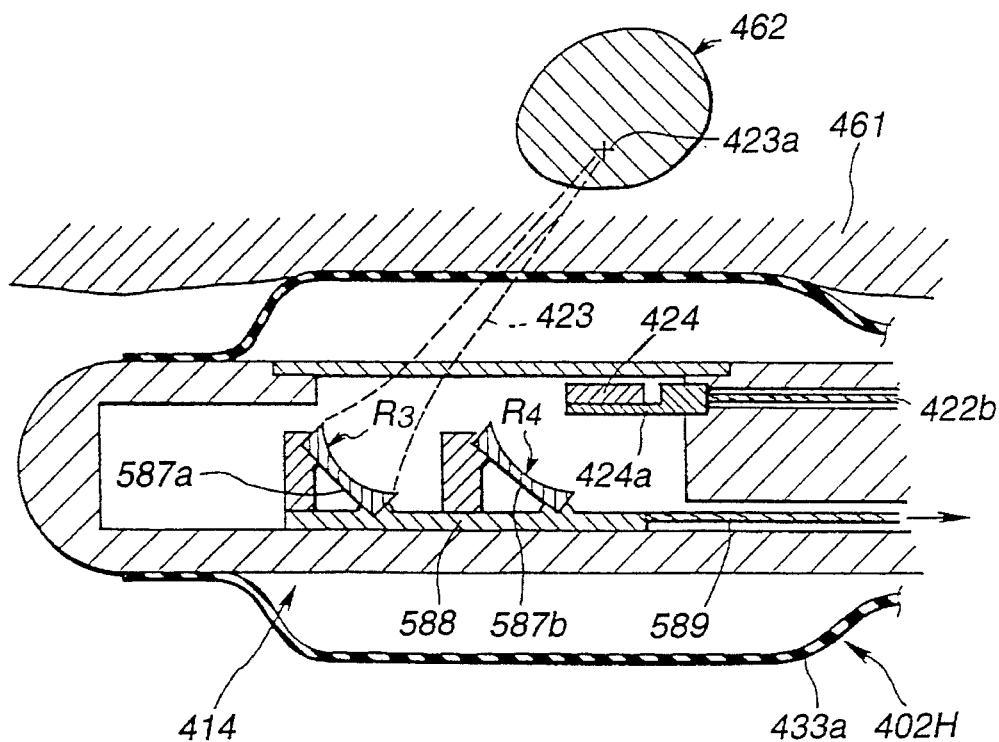

As shown in FIGS. 91 and 92, in the end portion of an ultrasonic probe 402H, the flexible shaft 422b is fixed at the fixed member 424a fixing the observatory ultrasonic transducer 424, so as to allow mechanical radial scanning, while the balloon 433a for controlling the ultrasonic focused point position, is provided, and in the end portion 414 of the probe 402H, therapeutic ultrasonic transducers 587a, 587b which are different in curvature R3, R4, are fixed onto a slider unit 588 which is slidable in the axial direction.

The slider unit 588 are slidingly moved in the axial direction in the end portion of the endoscope by the push-pull operation of the wire 589, such that the therapeutic ultrasonic transducer having ultrasonic focused point 423a suitable for therapy can be appropriately selected.

Figure 93A:
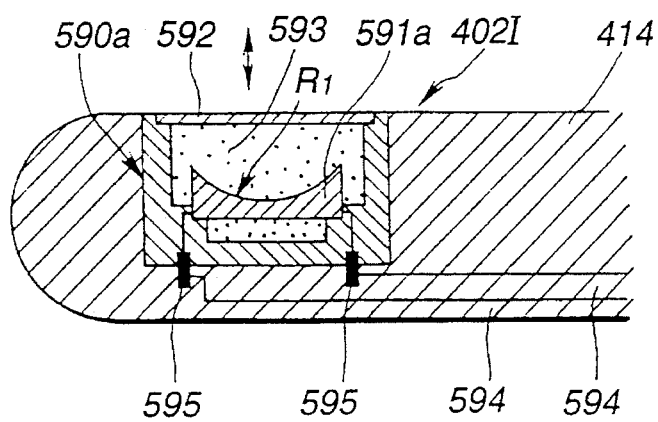

FIG. 93A is a diagram showing the schematic configuration of the end portion of an ultrasonic probe 402I of the thirty-second embodiment.

As shown in FIG. 93A, a first transducer unit 590a provided with the therapeutic ultrasonic transducer 591a having a curvature of R1, is removably provided in the end portion 414 of the probe 402I. An elastic membrane 592 is provided on said transducer unit 590a, and a filling material 593 such as a gelable liquid is filled in the unit 590a.

Lead lines 595 built in the probe body and electrodes of the unit 590a are electrically connected when assembled.

Figure 93B:
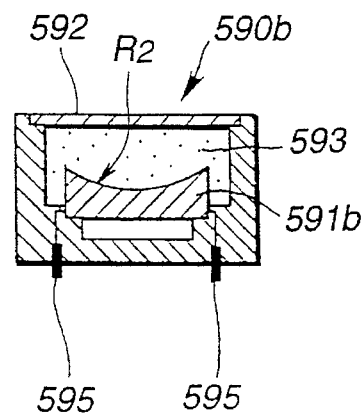
FIG. 93B is a view showing a simple substance of a transducer unit which is detachably mounted on the distal-end part of the ultrasonic probe.

Reference numeral 590b in FIG. 93B is a second transducer unit which can be replaced with the first unit 590a and has the same outline dimension as the first unit 590a. The therapeutic ultrasonic transducer 591b with a curvature of R2, the elastic membrane 592, and the filling materials 593 are built in the unit to change the focused point of the ultrasonic waves.

After the probe 402I provided with the transducer unit 590a is inserted in a celom, therapeutic ultrasonic waves are irradiated from the therapeutic ultrasonic transducer 591a toward the treatment region. If the ultrasonic focused point does not meet with the region, the probe 402I will be removed out of the celom once, and then the unit can be replaced with other transducer unit 590b having a suitable ultrasonic focused point so as to allow therapy for the region.

In this manner, transducer units each having therapeutic transducer with different curvature, are provided to be replaceable for the probe, such that the ultrasonic probes having various focused points can be available.

It is configured that the transducer unit can be replaced, whereby the shape of the end portion can be simplified and thus the probe dimension can be sized in a small diameter.

Further, the therapeutic transducer is replaceable, so as to facilitate cleaning and sterilizing for the therapeutic transducer and ultrasonic probe.

Figure 94:
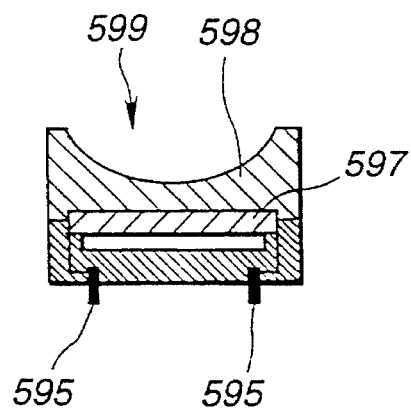

As shown in FIG. 94, an transducer unit 599 may be configured with a plane type transducer 597, and an irradiation face type acoustic lens 598 fixed over the upper part of the transducer 597, instead of the transducer units 590a, 590b provided with the irradiation face type transducers 591a, 591b.

Figure 95A:
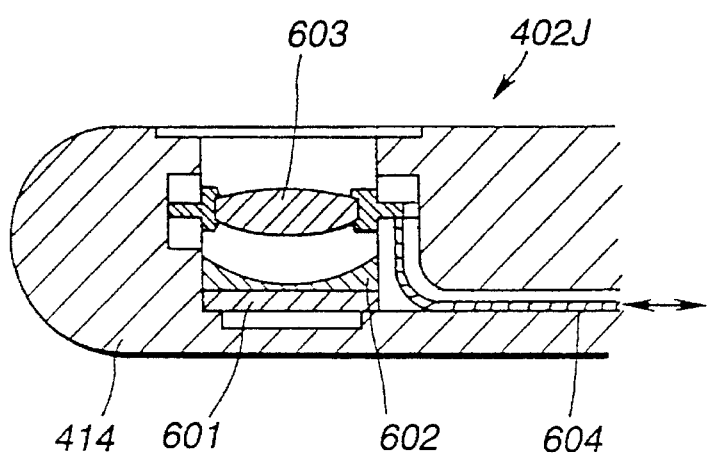
FIG. 95A to FIG. 95C relate to a thirty-third embodiment of the invention, FIG. 95A being a view showing a schematic arrangement of a distal-end part of an ultrasonic probe in the thirty-third embodiment.

FIG. 95A is a diagram showing a schematic configuration of the end portion of an ultrasonic probe 402J according to the thirty-third embodiment of the invention.

As shown in FIG. 95A, a plane type therapeutic transducer 601, an acoustic lens 602, and a focus variable acoustic lens 603 are provided in the tip part 414 of an ultrasonic probe 402J.

Figure 95B:
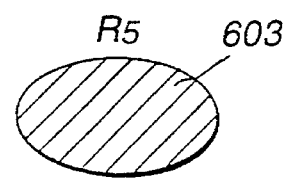
Figure 95C:
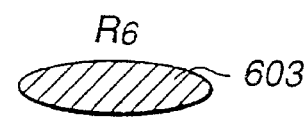

The variable focus acoustic lens 603 is formed of an elastic bag-like body filled up with gelable liquid or gel-like material, and the curvature of the lens 603 can be changed into, for example, R5, R6, by the push-pull movement of a wire 604 as shown in FIGS. 95B, 95C, so as to vary the focused point of ultrasonic waves irradiated from the therapeutic ultrasonic transducer. The other operations and advantages are similar to of said embodiment, and like reference characters denote like parts, and the description will be omitted.

The present invention is not limited to the above, and includes modifications or embodiments derived from or a combination of the aboveembodiments and alternate examples.

What is claimed is:

1. An ultrasonic diagnosis and therapy system comprising:

ultrasonic observation and therapy means provided with an observation ultrasonic transducer for transmitting and receiving an observation ultrasonic wave in order to acquire an ultrasonic image and a therapeutic ultrasonic transducer for outputting a therapeutic ultrasonic wave for conducting therapy with respect to an object part so as to be focused, on the side of a distal end of an elongated insertion part capable of being inserted into a coelom;

signal processing means for conducting signal processing which generates a signal driving said observation ultrasonic transducer and which generates an image signal from an ultrasonic signal which is received by said observation ultrasonic transducer;

drive means for driving said therapeutic ultrasonic transducer to generate a drive signal for generating a therapeutic ultrasonic wave;

display means for inputting said image signal to thereby display said ultrasonic image corresponding to said image signal; and scanning means for scanning said observation ultrasonic wave under a state in which a focusing point of said therapeutic ultrasonic wave is locked to a predetermined position within a scanning range of said observation ultrasonic wave.

2. A system according to claim 1, wherein said scanning means includes mechanical scanning means for rotating said observation ultrasonic transducer, for at least a predetermined angle which covers said scaning range, wherein said focusing point exists in an irradiation direction of said observation ultrasonic wave at a time said observation ultrasonic transducer is rotated through a certain angle.

3. A system according to claim 1, wherein said observation ultrasonic transducer is formed by a transducer array in which a plurality of ultrasonic transducers are arranged in the form of a belt along a single plane, wherein said scanning means includes electronic scanning means which electrically drives said transducer array in changing of timing, and wherein said scanning range including a direction to which said focusing point belongs is scanned with said observation ultrasonic wave by said electronic scanning means.

4. A system according to claim 3, wherein said single plane is a planar plane, and wherein said electronic scanning means electrically drives the plurality of ultrasonic transducers in changing of timing, whereby said scanning range including the direction to which said focusing point belongs is scanned by said observation ultrasonic wave.

5. A system according to claim 3, wherein said single plane is a cylindrical face, and wherein said electronic scanning means successively drives each of said ultrasonic transducers electrically, whereby scanning is made radially in each of directions corresponding to said scanning range including a direction to which said focusing point belongs, by said observation ultrasonic wave.

6. A system according to claim 3, wherein setting is made such that said focusing point exists in a radial direction of an outputting face which outputs the ultrasonic wave, of at least one of said plurality of ultrasonic transducers.

7. A system according to claim 1, wherein said focusing point is set so as to reside on a two equally divided line which substantially divides the scanning range in two.

8. A system according to claim 1, further comprising marker display means for displaying a marker at a position which corresponds to said focusing point, on an image of said ultrasonic signal.

9. A system according to claim 1, wherein said therapeutic ultrasonic transducer has a concave-shaped outputting face which outputs the ultrasonic wave to output the focused therapeutic ultrasonic wave from said outputting face.

10. A system according to claim 1, wherein manipulation of transmission and receiving of said observation ultrasonic wave is possible in parallel with manipulation which irradiates said therapeutic ultrasonic wave to said focusing point.

11. A system according to claim 1, wherein said observation ultrasonic transducer and said therapeutic ultrasonic transducer are driven by respective frequencies which are different from each other.

12. A system according to claim 1, wherein said observation ultrasonic transducer and said therapeutic ultrasonic transducer are driven by respective frequencies thereof which are different from each other, of 2 to 12 MHz.

13. A system according to claim 1, wherein said therapeutic ultrasonic transducer includes a plurality of ultrasonic transducers which are different in distance to the focusing point from each other, and wherein the system further comprises selection means for selecting the used ultrasonic transducers.

14. A system according to claim 1, wherein said therapeutic ultrasonic transducer includes distance modification means for modifying a distance to the focusing point.

15. A system according to claim 1, wherein said scanning means includes therapeutic ultrasonic scanning means for scanning the therapeutic ultrasonic wave.

16. A system according to claim 1, wherein said display means includes head mount displays having respective display faces thereof in front of eyes of an operator.

17. A system according to claim 1, further comprising an X-ray CT device for displaying a tomographic image due to an X-ray.

18. A system according to claim 1, further comprising an MRI device for displaying a tomographic image which utilizes nuclear magnetic resonance.

19. An ultrasonic probe comprising:

an elongated insertion part insertable into a coelom;

a first therapeutic ultrasonic transducer arranged on the side of a distal end of said insertion part, for outputting a therapeutic ultrasonic wave for conducting therapy with respect to an object part, so as to be focused;

an observation ultrasonic transducer arranged on the side of the distal end of said insertion part, for transmitting and receiving an observation ultrasonic wave over a scanning range which is set in order to acquire an ultrasonic image; and lock means for locking a focusing point of said therapeutic ultrasonic wave to a predetermined position in said scanning range.

20. An ultrasonic probe according to claim 19, further comprising a bendable curvature part at the side of the distal end of said insertion part.

21. An ultrasonic probe according to claim 19, wherein a curvature part is provided closer to the rear of the insertion part than said therapeutic ultrasonic transducer and said observation ultrasonic transducer.

22. An ultrasonic probe according to claim 19, further comprising optically observing optical observation means on the side of the distal end of said insertion part.

23. An ultrasonic probe according to claim 22, wherein said optical observation means is provided closer to the rear of the insertion part than said first therapeutic ultrasonic transducer and said observation ultrasonic transducer.

24. An ultrasonic probe according to claim 22, wherein said optical observation means is of a strabismus type whose observation direction is a slant forward direction.

25. An ultrasonic probe according to claim 19, wherein said insertion part includes a channel therein into which a treatment tool for conducting a treatment is insertable.

26. An ultrasonic probe according to claim 19, further comprising ultrasonic focusing means for focusing the ultrasonic wave outputted from said first therapeutic ultrasonic transducer through a predetermined distance.

27. An ultrasonic probe according to claim 26, wherein said ultrasonic focusing means is formed by one in which a face of said first therapeutic ultrasonic transducer, which outputs the ultrasonic wave, is formed substantially into a concave face.

28. An ultrasonic probe according to claim 19, wherein said first therapeutic ultrasonic transducer has an area outputting the ultrasonic wave, which is larger than that of said observation ultrasonic transducer.

29. An ultrasonic probe according to claim 19, further comprising scanning means for scanning the ultrasonic wave which is outputted from said observation ultrasonic transducer.

30. An ultrasonic probe according to claim 29, wherein said observation ultrasonic transducer has an ultrasonic transducer array in which a plurality of ultrasonic transducers are arranged, and wherein said scanning means has includes electronic scanning means for electronically driving said ultrasonic transducer array.

31. An ultrasonic probe according to claim 29, wherein said scanning means has mechanical scanning means for mechanically driving said observation ultrasonic transducer.

32. An ultrasonic probe according to claim 29, wherein said scanning means includes radial scanning means for scanning the ultrasonic wave which is outputted from said observation ultrasonic transducer, in a radial direction which is perpendicular to an axis of said insertion part.

33. An ultrasonic probe according to claim 29, wherein said scanning means includes linear scanning means for scanning the ultrasonic wave which is outputted from said observation ultrasonic transducer, in a plane which is parallel to an axis of said insertion part.

34. An ultrasonic probe according to claim 29, wherein said observation ultrasonic transducer includes an ultrasonic transducer array in which the plurality of ultrasonic transducers are arranged along a convex face, in a plane including an axis of said insertion part, and wherein said scanning means electronically drives said ultrasonic transducer array.

35. An ultrasonic probe according to claim 19, wherein said focusing point is set substantially to a center of said scanning range.

36. An ultrasonic probe according to claim 19, further comprising cooling means for cooling said first therapeutic ultrasonic transducer.

37. An ultrasonic probe according to claim 36, wherein said cooling means includes a line for supplying cooling liquid for cooling said first therapeutic ultrasonic transducer, to a location in the vicinity of said first therapeutic ultrasonic transducer.

38. An ultrasonic probe according to claim 19, further comprising temperature detection means for detecting temperature in the vicinity of said first therapeutic ultrasonic transducer.

39. An ultrasonic probe according to claim 19, further comprising a receiving coil which receivers a nuclear magnetic resonance signal which utilizes nuclear magnetic resonance, on the side of the distal end of said insertion part.

40. An ultrasonic probe according to claim 19, wherein said first therapeutic ultrasonic transducer is provided nearer the distal end of said insertion part than said observation ultrasonic transducer.

41. An ultrasonic probe according to claim 40, wherein said first therapeutic ultrasonic transducer is provided detachably at a position nearer the distal end of said insertion part than said observation ultrasonic transducer.

42. An ultrasonic probe according to claim 41, wherein a second therapeutic ultrasonic transducer which is different in characteristic from said first therapeutic ultrasonic transducer is capable of being detachably mounted on a position near the distal end of said insertion part.

43. An ultrasonic probe according to claim 19, wherein said first therapeutic ultrasonic transducer and said observation ultrasonic transducer have an integrated structure.

44. An ultrasonic probe according to claim 19, wherein said first therapeutic ultrasonic transducer and said observation ultrasonic transducer have structures formed at different positions by a common electric acoustic conversion element.

45. An ultrasonic probe according to claim 19, wherein said observation ultrasonic transducer is formed substantially at a center position of said electric acoustic conversion element.

46. An ultrasonic probe according to claim 19, wherein a balloon which receives an ultrasonic transfer medium is mounted at the periphery of a portion of said insertion part, in which said first therapeutic ultrasonic transducer and said observation ultrasonic transducer are built.

47. An ultrasonic probe according to claim 19, wherein said first therapeutic ultrasonic transducer has a plurality of ultrasonic transducers which are different from each other in distance to the focusing point.

48. An ultrasonic endoscope comprising:

an elongated insertion part insertable into a coelom;

an illumination optical system arranged on the side of a distal end of said insertion part, for outputting illumination light;

an observation optical system for optically observing an object which is illuminated by said illumination light;

an observation ultrasonic transducer arranged on the side of the distal end of said insertion part, for transmitting and receiving an observation ultrasonic wave to acquire an ultrasonic image; and a therapeutic ultrasonic transducer arranged on the side of the distal end of said insertion part, for irradiating, in focusing, an ultrasonic wave for conducting therapy with respect to an object part.

49. An ultrasonic diagnosis and therapy system comprising:

ultrasonic observation and therapy means provided with a bendable curvature part, an observation ultrasonic transducer for transmitting and receiving an observation ultrasonic wave to acquire an ultrasonic image and a therapeutic ultrasonic transducer for outputting a therapeutic ultrasonic wave for conducting therapy with respect to an object part so as to be focused;

signal processing means for conducting signal processing for generating a signal driving said observation ultrasonic transducer and for generating an image with respect to the ultrasonic wave which is received by said observation ultrasonic transducer;

drive means for driving said therapeutic ultrasonic transducer to generate a drive signal for generating the therapeutic ultrasonic wave; and display means for displaying an image signal which is generated by said signal processing means.

50. A system according to claim 49, further comprising focusing-point adjusting means for variably setting a focusing point at which the ultrasonic wave which is outputted from said therapeutic ultrasonic transducer is focused within the object part.

51. A system according to claim 50, wherein said focusing-point adjusting means is depth adjusting means for variably setting the focusing point with respect to a depth direction of said object part.

52. A system according to claim 50, wherein said focusing-point adjusting means variably sets the focusing point with respect to a direction perpendicular to the depth direction of said object part.

53. A system according to claim 50, wherein said focusing-point adjusting means is movement means for moving said therapeutic ultrasonic transducer.

54. An ultrasonic diagnosis and therapy system comprising:

ultrasonic observation and therapy means provided, on the side of a distal end of an elongated insertion part capable of being inserted into a coelom, with an illumination optical system for outputting illumination light, an observation optical system for optically observing an object which is illuminated by said illumination light, an observation ultrasonic transducer for transmitting and receiving an observation ultrasonic wave to acquire an ultrasonic image and a therapeutic ultrasonic transducer for irradiating the ultrasonic wave for conducting therapy with respect to an object part so as to be focused;

signal processing means for conducting signal processing for generating a signal driving said observation ultrasonic transducer and for generating an image with respect to an ultrasonic wave which is received by said observation ultrasonic transducer;

drive means for driving said therapeutic ultrasonic transducer to generate a drive signal for generating a therapeutic ultrasonic wave; and display means for displaying the image signal which is generated by said signal processing means.

55. An ultrasonic diagnosis and therapy system according to claim 54, wherein acoustic variation of the object part which is in the course of the fact that said therapeutic ultrasonic wave is irradiated in focusing is capable of being displayed.

56. An ultrasonic diagnosis and therapy system according to claim 54, wherein said display means includes a head mount display which is capable of being mounted on a head of an operator and which has respective display faces in front of eyes of said operator.

57. An ultrasonic diagnosis and therapy system according to claim 54, further comprising an X-ray CT device for displaying a tomographic image due to an X-ray.

58. An ultrasonic diagnosis and therapy system according to claim 54, further comprising an MRI device for displaying a tomographic image which utilizes nuclear magnetic resonance.

59. An ultrasonic diagnosis and therapy system comprising:

ultrasonic observation and therapy means provided, on the side of a distal end of an elongated insertion part insertable into a coelom, with an observation ultrasonic transducer for transmitting and receiving an observation ultrasonic wave to acquire an ultrasonic image and a therapeutic ultrasonic transducer for outputting a therapeutic ultrasonic wave for conducting therapy with respect to an object part so as to be focused;

signal processing means for conducting signal processing for generating a signal driving said observation ultrasonic transducer and for generating an image signal with respect to an ultrasonic signal which is received by said observation ultrasonic transducer;

drive means for driving said therapeutic ultrasonic transducer to generate a drive signal for generating the therapeutic ultrasonic wave;

display means for displaying said ultrasonic image corresponding to said image signal; and irradiation-state confirmation means for displaying a state of the object part in the vicinity of a focusing point to which said therapeutic ultrasonic wave is irradiated, onto said display means as said ultrasonic image.

60. An ultrasonic probe comprising:

an elongated insertion part insertable into a coelom;

a therapeutic ultrasonic transducer arranged on the side of a distal end of said insertion part, for outputting a therapeutic ultrasonic wave for conducting therapy with respect to an object part so as to be focused; and an observation ultrasonic transducer arranged on the side of the distal end of said insertion part, for transmitting and receiving an observation ultrasonic wave to acquire an ultrasonic image, over a set scanning range including a direction in which said therapeutic ultrasonic wave is outputted.

61. An ultrasonic probe comprising:

an elongated insertion part insertable into a coelom;

a therapeutic ultrasonic transducer arranged on the side of a distal end of said insertion part, for outputting a therapeutic ultrasonic wave for conducting therapy with respect to an object part so as to be focused; and an observation ultrasonic transducer arranged on the side of the distal end of said insertion part, for transmitting and receiving an observation ultrasonic wave to acquire an ultrasonic image so as to be overlapped with a direction in which said therapeutic ultrasonic wave is emanated.

62. An ultrasonic endoscope comprising:

an elongated insertion part insertable into a coelom;

an observation ultrasonic transducer arranged on the side of a distal end of said insertion part, for transmitting and receiving an observation ultrasonic wave to acquire an ultrasonic image;

a therapeutic ultrasonic transducer arranged on the side of the distal end of said insertion part, for outputting a therapeutic ultrasonic wave for conducting therapy with respect to an object part, so as to be focused; and optical observation means arranged on the side of the distal end of said insertion part, including an illumination window for outputting illumination light and an observation window for optically observing an object which is illuminated by said illumination light, said optical observation means including an optical observation range which is set so as to be overlapped with a direction in which said therapeutic ultrasonic wave is outputted.

63. An ultrasonic diagnosis and therapy system comprising:

ultrasonic observation and therapy means provided, on the side of a distal end of an elongated insertion part insertable into a coelom, with an observation ultrasonic transducer for transmitting and receiving an observation ultrasonic wave to acquire an ultrasonic image and a therapeutic ultrasonic transducer for outputting a therapeutic ultrasonic wave for conducting therapy with respect to an object part so as to be focused;

signal processing means for conducting signal processing for generating a signal driving said observation ultrasonic transducer and for generating an image signal from an ultrasonic signal which is received by said observation ultrasonic transducer;

drive means for driving said therapeutic ultrasonic transducer to generate a drive signal for generating the therapeutic ultrasonic wave;

display means to which said image signal is inputted for displaying said ultrasonic image corresponding to said image signal;

scanning means for scanning said observation ultrasonic wave; and lock means for locking a focusing point of said therapeutic ultrasonic wave to a predetermined position on said ultrasonic image, with respect to scanning of said observation ultrasonic wave.

64. An ultrasonic probe comprising:

an elongated insertion part insertable into a coelom;

a therapeutic ultrasonic transducer arranged on the side of a distal end of said insertion part, for outputting a therapeutic ultrasonic wave for conducting therapy With respect to an object part so as to be focused;

an observation ultrasonic transducer arranged on the side of the distal end of said insertion part, for transmitting and receiving an observation ultrasonic wave over a scanning range which is set to acquire an ultrasonic image; and a lock mechanism for locking a focusing point of said therapeutic ultrasonic wave in a predetermined direction of said scanning range.

65. An ultrasonic probe comprising:

an elongated insertion part capable of being inserted into a coelom;

a therapeutic ultrasonic transducer arranged on the side of a distal end of said insertion part, for outputting a therapeutic ultrasonic wave for conducting therapy with respect to an object part so as to be focused; and an observation ultrasonic transducer arranged on a plane substantially the same as said therapeutic ultrasonic transducer, on the side of the distal end of said insertion part, for transmitting and receiving an observation ultrasonic wave.

66. A therapy method comprising the steps of:

a first step of inserting, into a coelom, an ultrasonic probe which is provided, on the side of a distal end of an insertion part, with an observation ultrasonic transducer for transmitting and receiving an observation ultrasonic wave for acquiring an ultrasonic image and a therapeutic ultrasonic transducer for outputting a therapeutic ultrasonic wave;

a second step of bringing the side of the distal end of said ultrasonic probe into intimate contact with the vicinity of a diagnosis object part within the coelom, to set the ultrasonic wave to a state in which the ultrasonic wave is capable of being outputted toward the diagnosis object part;

a third step of displaying an ultrasonic image from the ultrasonic signal which is received by said observation ultrasonic transducer, by scanning of said observation ultrasonic wave;

a fourth step of modifying a scanning direction of the observation ultrasonic wave which is outputted toward said diagnosis object part, to set a lesion part to be conducted in therapy, to a state in which said lesion part is displayed on said ultrasonic image;

a fifth step of adjusting the side of said ultrasonic probe so that a position on said ultrasonic image which corresponds to a focusing point of said therapeutic ultrasonic wave and a display position of said lesion part are in agreement with each other;

a sixth step of conducting high-temperature therapy due to irradiation of said therapeutic ultrasonic wave with respect to said lesion part set to said focusing point;

a seventh step of observing a state of said lesion part to which said therapeutic ultrasonic wave is irradiated, on said ultrasonic image; and an eighth step of further conducting the irradiation of said therapeutic ultrasonic wave in case where said lesion part observed on said ultrasonic image does not reach a state suitable for therapy.

* * * * *